US012378589B2

(12) United States Patent
Beauprez et al.

(10) Patent No.: US 12,378,589 B2
(45) Date of Patent: Aug. 5, 2025

(54) IN VIVO SYNTHESIS OF SIALYLATED COMPOUNDS

(71) Applicant: Inbiose N.V., Ghent (BE)

(72) Inventors: Joeri Beauprez, Bredene (BE); Pieter Coussement, Gentebrugge (BE); Dries Van Herpe, Wondelgem (BE); Gert Peters, Ghent (BE); Annelies Vercauteren, Eke (BE)

(73) Assignee: INBIOSE N.V., Ghent (BE)

( * ) Notice: Subject to any disclaimer, the term of this patent is extended or adjusted under 35 U.S.C. 154(b) by 61 days.

(21) Appl. No.: 17/993,441

(22) Filed: Nov. 23, 2022

(65) Prior Publication Data

US 2023/0399670 A1 Dec. 14, 2023

Related U.S. Application Data

(62) Division of application No. 16/473,932, filed as application No. PCT/EP2017/084593 on Dec. 26, 2017, now Pat. No. 11,535,878.

(30) Foreign Application Priority Data

Dec. 27, 2016 (EP) .................................. 16206916

(51) Int. Cl.
C12N 9/80 (2006.01)
C12N 9/10 (2006.01)
C12N 9/12 (2006.01)
C12N 9/16 (2006.01)
C12N 9/88 (2006.01)
C12N 9/90 (2006.01)
C12N 15/52 (2006.01)
C12P 19/18 (2006.01)
C12P 19/26 (2006.01)

(52) U.S. Cl.
CPC ............ *C12P 19/18* (2013.01); *C12N 9/1029* (2013.01); *C12N 9/1085* (2013.01); *C12N 9/1205* (2013.01); *C12N 9/16* (2013.01); *C12N 9/80* (2013.01); *C12N 9/88* (2013.01); *C12N 9/90* (2013.01); *C12N 15/52* (2013.01); *C12P 19/26* (2013.01)

(58) Field of Classification Search
CPC ......... C12P 21/005; C12P 19/18; C12P 19/28; C12N 9/1081; C12N 15/70; C12N 9/1241; C12N 15/75; C07K 2317/41; C12Y 302/01018; C12Y 207/07043; C12Y 501/03014; C12Y 204/99001; C12Y 203/01004; C12Y 203/01003; C12Y 204/01022; C12Y 204/01143; C12Y 204/01101; C12Y 205/01056; C12Y 401/03003; C12Y 501/03008
USPC .......................................................... 435/84
See application file for complete search history.

(56) References Cited

U.S. PATENT DOCUMENTS

| 5,565,350 A | 10/1996 | Kmiec |
| 2005/0142643 A1 | 6/2005 | Shiba et al. |
| 2013/0266987 A1 | 10/2013 | Mach-Aigner et al. |
| 2015/0376610 A1 | 12/2015 | Oh et al. |

FOREIGN PATENT DOCUMENTS

| CN | 101273139 A | 9/2008 |
| CN | 103602627 B | 3/2015 |
| CN | 106190938 A | 12/2016 |
| EP | 1484406 A1 | 12/2004 |
| EP | 2927316 A1 | 10/2015 |
| KR | 10-2016-0002509 A | 1/2016 |
| WO | 93/22443 A1 | 11/1993 |
| WO | 00/15815 A1 | 3/2000 |
| WO | 2007/101862 A1 | 9/2007 |
| WO | 2008/097366 A2 | 8/2008 |
| WO | 2012/007481 A2 | 1/2012 |

(Continued)

OTHER PUBLICATIONS

Borisova et al., The N-Acetylmuramic Acid 6-Phosphate Phosphatase MupP Completes the Pseudomonas Peptidoglycan Recycling Pathway Leading to Intrinsic Fosfomycin Resistance, mBio., vol. 8, No. 2 (Mar. 28, 2017), pp. e00092-17.

(Continued)

*Primary Examiner* — Robert B Mondesi
*Assistant Examiner* — Mohammad Y Meah
(74) *Attorney, Agent, or Firm* — TraskBritt

(57) ABSTRACT

This disclosure is in the technical field of synthetic biology and metabolic engineering. More particularly, this disclosure is in the technical field of fermentation of metabolically engineered microorganisms. This disclosure describes engineered micro-organisms able to synthesize sialylated compounds via an intracellular biosynthesis route. These micro-organisms can dephosphorylate N-acetylglucosamine-6-phosphate to N-acetyl glucosamine and convert the N-acetylglucosamine to N-acetylmannosamine. These micro-organisms also have the ability to convert N-acetyl-mannosamine to N-acetyl-neuraminate. Furthermore, this disclosure provides a method for the large scale in vivo synthesis of sialylated compounds, by culturing a microorganism in a culture medium, optionally comprising an exogenous precursor such as, but not limited to lactose, lactoNbiose, N-acetyllactosamine and/or an aglycon, wherein the microorganism intracellularly dephosphorylates N-acetylglucosamine-6-phosphate to N-acetylglucosamine, converts N-acetyl-glucosamine to N-acetylmannosamine and convert the latter further to N-acetyl-neuraminate.

20 Claims, 7 Drawing Sheets

Specification includes a Sequence Listing.

(56) References Cited

FOREIGN PATENT DOCUMENTS

| WO | 2012/083329 A1 | 6/2012 |
|----|----------------|--------|
| WO | 2015/150328 A1 | 10/2015 |
| WO | 2016/075243 A1 | 5/2016 |

OTHER PUBLICATIONS

Chen et al., Advances in the Biology and Chemistry of Sialic Acids, ACS Chem. Biol., vol. 5, No. 2, (Dec. 18, 2009), pp. 163-176.
Chinese Search Report for Chinese Application No. 201780080949. 9, dated Nov. 16, 2022, 2 pages.
Database WPI, Week 201715, Thomson Scientific, AN 2016-78892G, XP002769734.
Database WPI, Week 201430, Thomson Scientific, AN 2014-H25887, XP002769733.
Devos et al., Practical Limits of Function Prediction, Proteins: Structure, Function and Genetics, vol. 41, Issue 1, (2000), pp. 98-107.
European Communication pursuant to Article 94(3) EPC for European Application No. 17832967.8, dated Apr. 23, 2021, 12 pages.
Fierfort et al., Genetic engineering of *Escherichia coli* for the economical production of sialylated oligosaccharides, J. Biotechnol., vol. 134, No. 3-4, (Apr. 30, 2018), pp. 261-265.
Hamamoto et al., Enzymatic synthesis of cytidine 5'-monophospho-N-acetylneuraminic acid, Biosci. Biotechnol. Biochem., vol. 69, No. 10 (Oct. 1, 2005), pp. 1944-1950.
International Search Report for International Application No. PCT/EP2017/084593, mailed Mar. 19, 2018, 9 pages.
International Written Opinion for International Application No. PCT/EP2017/084593, mailed Mar. 19, 2018, 10 pages.
Ishikawa et al., Microbial production of N-acetylneuraminic acid by genetically engineered *Escherichia coli*, Carbohydr. Res., vol. 345, No. 18, (Nov. 28, 2010), pp. 2605-2609.
Japanese Decision of Refusal for Japanese Application No. 2019-555065, dated Aug. 25, 2022, 6 pages with English translation.
Japanese Notice of Reasons for Refusal for Japanese Application No. 2019-555065, dated Jan. 25, 2022, 12 pages with English translation.
Kisselev, Polypeptide Release Factors in Prokaryotes and Eukaryotes: Same Function, Different Structure, Structure, vol. 10, No. 1, (Jan. 2002), pp. 8-9.
Koonin et al., Computer analysis of bacterial haloacid dehalogenases defines a large superfamily of hydrolases with diverse specificity—Application of an iterative approach to database search, J. Mol. Biol., vol. 244, No. 1 (Nov. 17, 1994), pp. 125-132.
Korean Notice of Final Rejection for Korean Application No. 10-2019-7022137, dated Jul. 10, 2023, 2 pages with English Translation.
Korean Request for the Submission of an Opinion for Korean Application No. 10-2019-7022137, dated Dec. 28, 2022, 23 pages with English translation.
Kuznetsova et al., Genome-wide Analysis of Substrate Specificities of the *Escherichia coli* Haloacid Dehalogenase-like Phosphatase Family, J. Biol. Chem., vol. 281, No. 47 (Nov. 24, 2006), pp. 36149-36161.
Lee et al., A synthetic suicide riboswitch for the high-throughput screening of metabolite production in *Saccharomyces cerevisiae*, Metab. Eng., vol. 28 (Jan. 14, 2015), pp. 143-150.
Li et al., Sialic acid metabolism and sialyltransferases: natural functions and applications, Appl. Microbiol. Biotechnol., vol. 94, No. 4, (Apr. 13, 2012), pp. 887-905.
Tao et al., Biotechnological production and applications of N-acetyl-d-neuraminic acid: current state and perspectives, Appl. Microbiol. Biotechnol., vol. 87, No. 4, (Jun. 8, 2010), pp. 1281-1289.
Wang et al., Sialic Acid Is an Essential Nutrient for Brain Development and Cognition, Annu. Rev. Nutr., vol. 29, No. 1, (Aug. 1, 2009), pp. 177-222.
Whisstock et al., Prediction of Poteinfunction Fromprotein Sequence and Structure, Quarterly Reviews of Biophysics, vol. 36, No. 3 (2003), pp. 307-340.
Witkowski et al., Conversion of a beta-ketoacyl synthase to a malonyl decarboxylase by replacement of the active-site cysteine with glutamine, Biochemistry, vol. 38, No. 36, (Sep. 7, 1999), pp. 11643-11650.
Zhu et al., Efficient whole-cell biocatalyst for Neu5Ac production by manipulating synthetic, degradation and transmembrane pathways, Biotech. Lett., vol. 39, No. 1, (Sep. 15, 2016), pp. 55-63.
May 20, 2021 Office Action from the Russian Patent Office.
English translation of the May 20, 2021 Russian Office Action.
Written Opinion from the Singapore Patent Office.
Second Written Opinion from the Singapore Patent Office.
Applicant's reply to the Russian Patent Office.
English language translation of the reply to the Russian Patent Office.
Applicant's reply to the second Written Opinion from Singapore.
Second Office Action from the Russian Patent Office.
English translation of the second Office Action from the Russian Patent Office.
Canadian Requisition by the Examiner and Search Report for Canadian Application No. 3048521, dated Feb. 12, 2024, 5 pages.
Chinese First Office Action for Chinese Application No. 201780080949. 9, dated Nov. 23, 2022, 26 pages with English translation.
Chinese First Office Action Response Amended Claims for Chinese Application No. 201780080949.9, dated May 24, 2023, 12 pages.
Chinese First Office Action Response for Chinese Application No. 201780080949.9, dated May 24, 2023, 31 pages with English translation.
Chinese request for reexamination for Chinese Application No. 201780080949.9, dated Apr. 25, 2024, 35 pages with English translation.
Chinese Second Office Action Response Amended Claims for Chinese Application No. 201780080949.9, dated Jan. 8, 2024, 6 pages.
Chinese Second Office Action Response for Chinese Application No. 201780080949.9, dated Aug. 22, 2023, 21 pages with English translation.
Chinese Second Office Action Response for Chinese Application No. 201780080949.9, dated Jan. 8, 2024, 50 pages with English translation.
Chinese Third Office Action Response for Chinese Application No. 201780080949.9, dated Jan. 25, 2024, 25 pages with English translation.
India Patent Examination Report for India Application No. 201917029091, dated May 26, 2023, 18 pages with English translation.
Korean Notice of Allowance for Korean Application No. 10-2023-7021715, dated Dec. 27, 2024, 21 pages with English translation.
Korean Notice of Reasons for Refusal Response Amended Claims for Korean Application No. 10-2023-7021715, dated May 21, 2024, 6 pages.
Korean Notice of Reasons for Refusal Response for Korean Application No. 10-2023-7021715, dated May 21, 2024, 72 pages with English translation.
Australian Patent Examination Report No. 1 for Australian Application No. 2017385601, dated Apr. 13, 2022, 4 pages.
Brazilian Search Report and Written Opinion for Brazilian Application No. BR112019013211-2, dated Dec. 26, 2017, 10 pages with English machine translation.
Fahs et al. "Approaches to Study Phosphatases" ACS Chem Biol. Nov. 18, 2016;11(11):2944-2961. doi: 10.1021/acschembio. 6b00570. Epub Oct. 4, 2016. PMID: 27700050.).
Indonesia Office Action for Indonesia Application No. P00202104271, dated Mar. 16, 2023, 8 pages with English translation.
Indonesia Office Action for Indonesia Application No. PID201906203, dated Mar. 9, 2021, 8 pages with English translation.
Korean Notice of Final Rejection for Korean Application No. 10-2023-7021715, dated Mar. 22, 2024, 8 pages with English translation.
Kuznetsova et al. "Functional Diversity of Haloacid Dehalogenase Superfamily Phosphatases from *Saccharomyces cerevisiae*: Bio-

(56) References Cited

OTHER PUBLICATIONS chemical, Structural, and Evolutionary Insights" J Biol Chem. Jul. 24, 2015;290 (30):18678-98. doi: 10.1074/jbc.M115.657916. Epub Jun. 12, 2015. PMID: 26071590; PMCID: PMC4513125.

New Zealand Patent Examination Report 1 for the New Zealand Patent Application No. 755558, dated May 12, 2023, 3 pages.

New Zealand Patent Examination Report 1 for the New Zealand Patent Application No. 755558, dated Oct. 14, 2022, 6 pages.

Singapore Examination Report for Singapore Application No. 11201905644S dated Sep. 19, 2023, 10 pages.

Singapore Written Opinion for Singapore Application No. 11201905644S dated Jan. 6, 2022, 10 pages.

Singapore Written Opinion for Singapore Application No. 11201905644S dated May 8, 2021, 12 pages.

Singapore Written Opinion for Singapore Application No. 11201905644S dated Oct. 3, 2020, 11 pages.

Fig. 6:

|  | 120 | 130 | 140 | 150 |
|---|---|---|---|---|
| EcAppA/1-432 | GCPQSGQ······VAII | ···ADVDERTRKTG | ······· | EAFAAGLAP· |
| EcYbR/1-199 | NRKFGGNVNAERIALL | ··AMYHDA····S | ········ | EVL········ |
| EcAphA/1-237 | TQAISAV·····CLLFALNSSAVALASSP | ············ | ······ | SPLNPG |
| EcYjgL/1-604 | EVLNTWR·····VGMNDFARIAGGQDNRR | ············ | ······ | NILSPG |
| EcYmL/1-168 | ················ | ············ | ········ | ········ |
| EcSerB/1-323 | AAWCVED·····YQVI | ···RLAGSLTARATRLAHEAQ | ······ | LDV· |
| EcybiV/1-271 | ···MSVK·····VIVT | ···DMDQTFLNDAKTYNQ | ······ | ···P· |
| EcYidA/1-270 | ···MAIK·····LIA|I···DMDGT|LLLPDHTIS | ············ | ····P· |
| EcCof/1-272 | ····MAR·····LAA|F···DMDGT|LLMPDHHLG | ············ | ····E· |
| EcYbhA/1-272 | ···MTTR·····VIA|L···DLDGT|LLTPKKTLL | ············ | ····P· |
| EcYaed/1-191 | ·MAKSVP·····AIF|L···DRDGT|INVDHGY···VHEIDNFEFID· |
| EcHisB/1-356 | ···MSQK·····YLF|I···DRDGT|LISEPPSDFQVDRFDKLAFEP· |
| EcNagD/1-250 | ···MTIK·····NVIC | ···DIDGVLMHDNVAVPGAAEFLHGIMDK· |
| BsArgL/1-272 | DTPVSPA·····GIL|I···DLDGT|VFRGNELIEGAREAIKTLRRM· |
| EcYedP/1-271 | ··MFSIQ·····QPLLVFSDLDGTLLDSHSYDWQPAAPWLTRLRE· |
| EcOtsB/1-266 | PELSAKY·····AWF|F···DLDGT|LAEIKPHPDQVV··VPDNILQ· |
| EcYihX/1-199 | ················ | ············ | ········ | ········ |
| EcYigL/1-561 | LCLGKLR·····LGSIQLGNSIGVLVVSLLLGQQHFSINTDALNL· |
| EcSurE/1-253 | ·····MR·····ILLS···NDDGVHAPGI | ········ | QTLAK· |
| EcYfG/1-225 | ···MKWD·····WIF|F···DADET|LFTFD | ········ | S··FT· |
| EcYfiG/1-222 | ··WQDVD·····TVL|L···DMDGT|LLDLA | ············ | FDNY·· |
| EcYigB/1-238 | ··LGRIS·····ALT|F···DLDDT|YDNR | ············ | PVILR· |
| EcYniC/1-222 | ··PRQIL·····AAI|F···DMDGL|LIDSE | ············ | PLWDR· |
| EcYigU/1-219 | ···MKLQ·····GVI|F···DLDGV|ITDTA | ············ | HLHFQ· |
| EcYqaB/1-188 | ··YERYA·····GLI|F···DMDGT|ILDTE | ············ | PTHRK· |
| EcYieH/1-221 | ··MSRIE·····AVF|F···DCDGT|LVDSE | ············ | VICSR· |
| PaNupP/1-223 | ···MRLR·····AVL|F···DMDGT|LLDTA | ············ | PDFIA· |
| EcGph/1-252 | ··FEDIR·····GVA|F···DLDGT|LVDSA | ············ | PGLAA· |
| EcYbiT/1-216 | ···MRCK·····GFL|F···DLDGT|LVDSL | ············ | PAVER· |
| ScDOG1/1-246 | ··EFSAD·····LCL|F···DLDGT|IVSTT | ············ | VAAEK· |

Motif 1

Fig. 6 cont.:

```
                            SEQUENCE LISTING

Sequence total quantity: 154
SEQ ID NO: 1            moltype = DNA   length = 69
FEATURE                 Location/Qualifiers
misc_feature            1..69
                        note = Synthetic DNA
source                  1..69
                        mol_type = other DNA
                        organism = synthetic construct
SEQUENCE: 1
gctgaacttg taggcctgat aagcgcagcg tatcaggcaa tttttataat cttcatttaa   60
atggcgcgc                                                           69

SEQ ID NO: 2            moltype = DNA   length = 69
FEATURE                 Location/Qualifiers
misc_feature            1..69
                        note = Synthetic DNA
source                  1..69
                        mol_type = other DNA
                        organism = synthetic construct
SEQUENCE: 2
gcgcaacgca attaatgtga gttagctcac tcattaggca ccccaggctt cgcctacctg   60
tgacggaag                                                           69

SEQ ID NO: 3            moltype = DNA   length = 75
FEATURE                 Location/Qualifiers
misc_feature            1..75
                        note = Synthetic DNA
source                  1..75
                        mol_type = other DNA
                        organism = synthetic construct
SEQUENCE: 3
cgcttaaaga tgcctaatcc gccaacggct tacattttac ttattgaggt gaatagtgta   60
ggctggagct gcttc                                                    75

SEQ ID NO: 4            moltype = DNA   length = 66
FEATURE                 Location/Qualifiers
misc_feature            1..66
                        note = synthetic DNA
source                  1..66
                        mol_type = other DNA
                        organism = synthetic construct
SEQUENCE: 4
ggcgtttgtc atcagagcca accacgtccg cagacgtggt tgctatcata tgaatatcct   60
ccttag                                                              66

SEQ ID NO: 5            moltype = DNA   length = 62
FEATURE                 Location/Qualifiers
misc_feature            1..62
                        note = synthetic DNA
source                  1..62
                        mol_type = other DNA
                        organism = synthetic construct
SEQUENCE: 5
taatgcgccg ccagtaaatc aacatgaaat gccgctggct ccgtgtaggc tggagctgct   60
tc                                                                  62

SEQ ID NO: 6            moltype = DNA   length = 70
FEATURE                 Location/Qualifiers
misc_feature            1..70
                        note = synthetic DNA
source                  1..70
                        mol_type = other DNA
                        organism = synthetic construct
```

```
SEQUENCE: 6
ccaacaacaa gcactggata aagcgagtct gcgtcgcctg gttcagttca catatgaata    60
tcctccttag                                                          70

SEQ ID NO: 7              moltype = DNA   length = 70
FEATURE                   Location/Qualifiers
misc_feature              1..70
                          note = synthetic DNA
source                    1..70
                          mol_type = other DNA
                          organism = synthetic construct
SEQUENCE: 7
aaaatacatc tggcacgttg aggtgttaac gataataaag gaggtagcaa gtgtaggctg    60
gagctgcttc                                                          70

SEQ ID NO: 8              moltype = DNA   length = 70
FEATURE                   Location/Qualifiers
misc_feature              1..70
                          note = synthetic DNA
source                    1..70
                          mol_type = other DNA
                          organism = synthetic construct
SEQUENCE: 8
cctccagata aaaaacggg gccaaaaggc cccggtagtg tacaacagtc catatgaata     60
tcctccttag                                                          70

SEQ ID NO: 9              moltype = DNA   length = 70
FEATURE                   Location/Qualifiers
misc_feature              1..70
                          note = synthetic DNA
source                    1..70
                          mol_type = other DNA
                          organism = synthetic construct
SEQUENCE: 9
gtttggcgtt tgtcatcaga gccaaccacg tccgcagacg tggttgctat gtgtaggctg    60
gagctgcttc                                                          70

SEQ ID NO: 10             moltype = DNA   length = 70
FEATURE                   Location/Qualifiers
misc_feature              1..70
                          note = Synthetic DNA
source                    1..70
                          mol_type = other DNA
                          organism = synthetic construct
SEQUENCE: 10
ttgtcattgt tggatgcgac gctcaagcgt cgcatcaggc ataaagcaga cttaagcgac    60
ttcattcacc                                                          70

SEQ ID NO: 11             moltype = DNA   length = 70
FEATURE                   Location/Qualifiers
misc_feature              1..70
                          note = Synthetic DNA
source                    1..70
                          mol_type = other DNA
                          organism = synthetic construct
SEQUENCE: 11
catggcggta atgcgccgcc agtaaatcaa catgaaatgc cgctggctcc gtgtaggctg    60
gagctgcttc                                                          70

SEQ ID NO: 12             moltype = DNA   length = 70
FEATURE                   Location/Qualifiers
misc_feature              1..70
                          note = synthetic DNA
source                    1..70
                          mol_type = other DNA
                          organism = synthetic construct
SEQUENCE: 12
ccaacaacaa gcactggata aagcgagtct gcgtcgcctg gttcagttca cttaagcgac    60
ttcattcacc                                                          70

SEQ ID NO: 13             moltype = DNA   length = 70
FEATURE                   Location/Qualifiers
misc_feature              1..70
                          note = synthetic DNA
source                    1..70
                          mol_type = other DNA
                          organism = synthetic construct
SEQUENCE: 13
aaaatacatc tggcacgttg aggtgttaac gataataaag gaggtagcaa gtgtaggctg    60
```

```
SEQ ID NO: 14          moltype = DNA  length = 70
FEATURE                Location/Qualifiers
misc_feature           1..70
                       note = synthetic DNA
source                 1..70
                       mol_type = other DNA
                       organism = synthetic construct
SEQUENCE: 14
cctccagata aaaaaacggg gccaaaaggc cccggtagtg tacaacagtc cttaagcgac    60
ttcattcacc                                                          70

SEQ ID NO: 15          moltype = DNA  length = 70
FEATURE                Location/Qualifiers
misc_feature           1..70
                       note = synthetic DNA
source                 1..70
                       mol_type = other DNA
                       organism = synthetic construct
SEQUENCE: 15
gcgcaacgca attaatgtga gttagctcac tcattaggca ccccaggctt gtgtaggctg    60
gagctgcttc                                                          70

SEQ ID NO: 16          moltype = DNA  length = 70
FEATURE                Location/Qualifiers
misc_feature           1..70
                       note = synthetic DNA
source                 1..70
                       mol_type = other DNA
                       organism = synthetic construct
SEQUENCE: 16
gctgaacttg taggcctgat aagcgcagcg tatcaggcaa ttttttataat cttaagcgac   60
ttcattcacc                                                          70

SEQ ID NO: 17          moltype = DNA  length = 70
FEATURE                Location/Qualifiers
misc_feature           1..70
                       note = synthetic DNA
source                 1..70
                       mol_type = other DNA
                       organism = synthetic construct
SEQUENCE: 17
caaaaagcgg tcaaattata cggtgcgccc ccgtgatttc aaacaataag gtgtaggctg    60
gagctgcttc                                                          70

SEQ ID NO: 18          moltype = DNA  length = 70
FEATURE                Location/Qualifiers
misc_feature           1..70
                       note = synthetic DNA
source                 1..70
                       mol_type = other DNA
                       organism = synthetic construct
SEQUENCE: 18
ataacgtggc ttttttggt aagcagaaaa taagtcatta gtgaaaatat cttaagcgac     60
ttcattcacc                                                          70

SEQ ID NO: 19          moltype = DNA  length = 20
FEATURE                Location/Qualifiers
misc_feature           1..20
                       note = synthetic DNA
source                 1..20
                       mol_type = other DNA
                       organism = synthetic construct
SEQUENCE: 19
caggtttccc gactggaaag                                                20

SEQ ID NO: 20          moltype = DNA  length = 20
FEATURE                Location/Qualifiers
misc_feature           1..20
                       note = synthetic DNA
source                 1..20
                       mol_type = other DNA
                       organism = synthetic construct
SEQUENCE: 20
tgtgcgtcgt tgggctgatg                                                20

SEQ ID NO: 21          moltype = DNA  length = 20
FEATURE                Location/Qualifiers
```

```
misc_feature            1..20
                        note = synthetic DNA
source                  1..20
                        mol_type = other DNA
                        organism = synthetic construct
SEQUENCE: 21
cgcttgtcat tgttggatgc                                                     20

SEQ ID NO: 22           moltype = DNA  length = 22
FEATURE                 Location/Qualifiers
misc_feature            1..22
                        note = synthetic DNA
source                  1..22
                        mol_type = other DNA
                        organism = synthetic construct
SEQUENCE: 22
gctgacaaag tgcgatttgt tc                                                  22

SEQ ID NO: 23           moltype = DNA  length = 20
FEATURE                 Location/Qualifiers
misc_feature            1..20
                        note = synthetic DNA
source                  1..20
                        mol_type = other DNA
                        organism = synthetic construct
SEQUENCE: 23
gtcgccctgt aattcgtaac                                                     20

SEQ ID NO: 24           moltype = DNA  length = 20
FEATURE                 Location/Qualifiers
misc_feature            1..20
                        note = synthetic DNA
source                  1..20
                        mol_type = other DNA
                        organism = synthetic construct
SEQUENCE: 24
ctttcggtca gaccaccaac                                                     20

SEQ ID NO: 25           moltype = DNA  length = 20
FEATURE                 Location/Qualifiers
misc_feature            1..20
                        note = synthetic DNA
source                  1..20
                        mol_type = other DNA
                        organism = synthetic construct
SEQUENCE: 25
acgcctctga tttggcaaag                                                     20

SEQ ID NO: 26           moltype = DNA  length = 20
FEATURE                 Location/Qualifiers
misc_feature            1..20
                        note = synthetic DNA
source                  1..20
                        mol_type = other DNA
                        organism = synthetic construct
SEQUENCE: 26
agccagtgcg cttaataacc                                                     20

SEQ ID NO: 27           moltype = DNA  length = 20
FEATURE                 Location/Qualifiers
misc_feature            1..20
                        note = synthetic DNA
source                  1..20
                        mol_type = other DNA
                        organism = synthetic construct
SEQUENCE: 27
gctgaacagc aatccacttg                                                     20

SEQ ID NO: 28           moltype = DNA  length = 20
FEATURE                 Location/Qualifiers
misc_feature            1..20
                        note = synthetic DNA
source                  1..20
                        mol_type = other DNA
                        organism = synthetic construct
SEQUENCE: 28
tgaacgatat ggtgagctgg                                                     20

SEQ ID NO: 29           moltype = DNA  length = 500
```

| FEATURE | Location/Qualifiers |
|---|---|
| misc_feature | 1..500 |
| | note = synthetic DNA |
| source | 1..500 |
| | mol_type = other DNA |
| | organism = synthetic construct |

SEQUENCE: 29
```
agatggaatg gcgattttca ctctaaattt taaaaattgc ctctttacaa tagcgaattt    60
cctaacccct ttttttttt gttgattgcc tattgctcgt tcacttccca tttatttct    120
ctcgaatttc accaaaagtt gatgtggata atcaatcatc gggcctattc ctgcgggtaa   180
aacgcagggc ccaactcagg atagggttta atattatttt agaggactta caagaaggaa   240
gttatatggt ttaaaaattg taacaaagtt agaacacatt tatttagcag gtctaattta   300
gggctgcaac tatcttttg gttattcata taaaatataa ttttttattt atatagaaa    360
tacaagtgga atcatcttta acgccagctt gtagtgcgca ttgcagaata atggaagttc   420
aaaaattaaa agcgaaggag aagtgatagt agaaagacg atgggaggct gggggacgaa   480
gagaaagtaa aagggttaat                                               500
```

| SEQ ID NO: 30 | moltype = DNA length = 500 |
|---|---|
| FEATURE | Location/Qualifiers |
| misc_feature | 1..500 |
| | note = synthetic DNA |
| source | 1..500 |
| | mol_type = other DNA |
| | organism = synthetic construct |

SEQUENCE: 30
```
tttttataa aagttgctgt tgatttgctc gagaacttat tgcttatttg gccctgataa    60
ctatataaga aaagaaatac agttattcct tgtttatgct ggcttttgt ccactttttc   120
tcaactatat aactatgatg ttggaaagga caccggttct gtaactttgc agtgaaaata   180
agtgtgatgg atgactgaga atgctttctt gtaagcgaaa agaagtacgt gttccaaaaa   240
taaagcagaa aggcgaaaag ggtcgaatgt aagcactaa ataaatattt taagaagagg   300
aaaagtcgcc tcagaaacgc taaaatgcat ccgatttccc aaagaggaag tctaatgttt   360
tcgatttgtg aaaaaaagat aaaaatcgaa gaaaatgtag ggagccgcgc gttacccgga   420
ttgatatttg agtgatcgac ggcgtcacaa agaaagaat gcttggctaa tcaagaaaag   480
tatgtggttt gtttcatcta                                               500
```

| SEQ ID NO: 31 | moltype = DNA length = 20 |
|---|---|
| FEATURE | Location/Qualifiers |
| misc_feature | 1..20 |
| | note = synthetic DNA |
| source | 1..20 |
| | mol_type = other DNA |
| | organism = synthetic construct |

SEQUENCE: 31
```
gcaggtctaa tttagggctg                                                20
```

| SEQ ID NO: 32 | moltype = DNA length = 20 |
|---|---|
| FEATURE | Location/Qualifiers |
| misc_feature | 1..20 |
| | note = synthetic DNA |
| source | 1..20 |
| | mol_type = other DNA |
| | organism = synthetic construct |

SEQUENCE: 32
```
agaaagcatt ctcagtcatc                                                20
```

| SEQ ID NO: 33 | moltype = DNA length = 1000 |
|---|---|
| FEATURE | Location/Qualifiers |
| misc_feature | 1..1000 |
| | note = synthetic DNA |
| source | 1..1000 |
| | mol_type = other DNA |
| | organism = synthetic construct |

SEQUENCE: 33
```
gactgcaaga tttcggcctg ggcggacggg aatcgtcagt tttgtaattt ctgtatcaat    60
gattttcatg gtctcttcct caagtccgag ccggtcgtat tgcttgccct gctcccagag   120
ttcaagattc atgacaatcg tgattcgttt attgcttctg accgcgccag cgccaaatag   180
cgtcatcaca ttgataatgc caaggcccct gatctcaaga aggtgctcaa ttaattccgg   240
agcgtttccc acaagagtat cctgatcctc ctgccgtatt tcaacgcaat catcggcaac   300
aaggcgatgc cctcttttca caagtctag cgctgtttcg cttttccga cgccgcttt    360
tcctgtgatc agcacgccga caccatatat atcgacaaga acgccatgaa ttgctgtggt   420
aggcgccagc ctgctctcaa ggaagttgg taaacggctt gacagtctg tcgttttcag   480
cggcgatctg aggacaggca ccccattttt ctcggaggcg tcaatcagct cctgcgggat   540
gggcatatct ctagaaagaa taatagctgg tgttacatca gtgcacagag aatccattcg   600
ctgcttttc tcctcttcag gaagctgttc aaagaaagaa agctcgtttt ttccgagaag   660
ctgcacgcgc tccctcgggt aatatgtaaa atatccggca atttcaatac ctggtcttga   720
taggtcactc attgtaatcg ggcggttaat tccttcttct ccgctgatta attccaaatt   780
gaactgttcc attacgtctt ttgtgcgaac ctttgccacg atatgttcct cctgttccgg   840
gctgccccga gcttgctcac aatacttca ttttatcact ttcgggctg aacctaaaac   900
agattttata aaggggggga aaacacctca gctggtctag atcactagtc tgaaaagag   960
```

```
taaaataaag gtattcaaat tccagaaagg cggatcatct                            1000

SEQ ID NO: 34            moltype = DNA   length = 1000
FEATURE                  Location/Qualifiers
misc_feature             1..1000
                         note = synthetic DNA
source                   1..1000
                         mol_type = other DNA
                         organism = synthetic construct
SEQUENCE: 34
aaggaacatg ctgacttatg aatatcaata acaatcgcc tattccgatt tactatcaga      60
ttatggagca attaaaaacc caaattaaga acgagagct gcagccggat atgcctcttc     120
cttctgagcg cgaatatgcc gaacaattcg ggatcagccg gatgacagtt cgccaggcgc    180
tttctaattt agttaatgaa ggcttgctct atcgcctgca agggcgggc acctttgtca     240
gcaagccaaa aatggaacaa gcacttcaag ggctgacaag cttaccgag gatatgaaaa     300
gccgcgggat gacaccgggc agcaggctca ttgattatca gcttattgat tcaactgagg    360
agctcgcggc tatattaggc tgcgggcacc cctcctctat ccataaaatc actcgggtgc    420
ggctggcaaa tgatattccg atggcggattg agtcctcaca tattccgttt gagcttgcgg   480
gtgaattgaa cgaatcgcat tttcagtcgt cgatcctatga tcatattgaa aggtacaaca   540
gcataccgat ttcccgtgca aaacaggagc ttgagccaag cgctgccacc acggaagaag    600
cgaatattct tggtattcaa aagggagcgc ctgtcctatt aattaaacga caacatatc    660
tgcagaacgg aactgctttt gagcatgcaa aatccgtata cagaggcgac cgttatacat    720
ttgtccacta tatggatcgt cttcataaa aaaagcctcc aacccttttt aaggattgga    780
gacatggcga aaatcaaact ggtcggtgc cggacgatat gtttcttttt tcgtcttgaa    840
cttccagatc ggtgatttcg ttttgccgtt aaaactgtct tccactataa tgtaccaata   900
ataaacagac tgccggttcaa gatgatccca gcggaattca gctgtgtccc cgctcttcac  960
ttgctcccgt tttccgagct cttcattggt atatacgtta                          1000

SEQ ID NO: 35            moltype = DNA   length = 1000
FEATURE                  Location/Qualifiers
misc_feature             1..1000
                         note = synthetic DNA
source                   1..1000
                         mol_type = other DNA
                         organism = synthetic construct
SEQUENCE: 35
tggcggacat ggaataaatc acaaacgaca aagatgacgc cggcaagaat agagttaatc      60
aaatagagca cgggcgcaac gaacaagaaa gaaaactcaa ccggttctgt aattccggtc    120
agcatagatg tgagcgccgc agaaatcatc acgccggaga tcatttttttt cttttccgga   180
cgcgcggtat ggataatggc aagagcaacg gccggcagac agaaaatcat gtaagggaaa    240
tccccccatca taaagcgccc ggctgtcggg tctcccgcga aaaaccttgt caggtcgccg    300
gttacggtgt tgcctgttga tgggtctgtg tattctccca tcataaaata gaaaggcgta    360
taaaaaatat gatgcaggcc aaaaggaatc agcaaacgat agatcgttgc ataaaagaac    420
aggccgactg ttgaatcggc aattaaactg ctggctgcgt taattccgtt ttggatcagc    480
ggccaaacga atgagaaaat gacgccgatc accaatgaac tgacgaagt aatgatcggg     540
acaaagcgtt ttccagagaa aaatccaagg accggatgca gctcgattga tgaaaatcgc    600
ttatataaat aggcgggag aagcccgata atgattcctc cgaaaaccccc catatcaatc    660
aggtgctcgg ctccttcata cggaggctga aggccgagta attttcccat attgtcgagg    720
gtgacggtta aaattaagta tccgatgaca gcggcaagtc cggctacacc ttctccgccg    780
gctaatccga tcgcgacccc cacggcgaaa atcagcggaa ggttatcgaa tacaacgccg    840
cccgcatcct ttataatagg gatgttcagt aaatcctttgt ctccgaaacg gagcaaaaga    900
cctgctgccg gcaggacggc aaccggagtc atcaacggc ggccaagctg ctgcagaatt    960
tgaaatgcct ttttaaacat gacagtctcc ttttattgtg                          1000

SEQ ID NO: 36            moltype = DNA   length = 1000
FEATURE                  Location/Qualifiers
misc_feature             1..1000
                         note = synthetic DNA
source                   1..1000
                         mol_type = other DNA
                         organism = synthetic construct
SEQUENCE: 36
gtgacacccc ctcaaagaga tagacaagca ccatatttgt tatgaccaat ttatgatact      60
tgtcattacg aatttagcac cgcccttatc aaactgtcaa tattaatttc tgaaaatttg    120
ttataaaaga aggatacaaa tcttttcatat tgggagggca aatggtatta tggtctcaat    180
gaaaagaac ggattgcata cagaatgggg agaatgaaat gacagcttta tattctgtta    240
tcaagtttaa aatcattgag ttaattaaat cgggcaaata tcaggcgaat gatcagctgc    300
cgacggagag tgagttttgc gaacaatatg atgtcagcag aacaactgtg agactggctc    360
tgcagcagct agagcttgag ggatatatta aagaattca aggaaaaggg acatttgtat     420
cggcggccaa aatacaaacg ccgattccgc ataagattac gagctttgca gaacaaaatga   480
gaggacttcg ttctgaatca aaagtgcttg agcttgtggt gattcctgcc gatcattcca    540
tcgccgagct tttgaaaatg aaagagaatg aacctgtcaa caagcttgtc agagtcagat    600
acgccgaggg ggaacctttg cagtatcata cctcatatat tccctggaag gcggcaccgg    660
ggctgcgga gaggaatgc accggctcgc tgtttgaatt gttaaggaca aaatacaata    720
ttgaaatcag caggggcacg gaatcgatcg aaccgatttt aacgatgaa acgatcagcg    780
gacacttatt aaccaatgtc ggagcgcctg cgttttatc agaatcccctt acctatgata   840
aaaatgaaga agtggtggaa tatgcgcaaa ttattcacg gggagaccga acgaaattca    900
ccgtagaaca gtcatatcat tcataaagca atgtgtttta agaaggggaat ggtggttcta   960
tgttttttatt tacgaatgga aaagtgctgt ggggagcagt                          1000
```

```
SEQ ID NO: 37            moltype = DNA  length = 20
FEATURE                  Location/Qualifiers
misc_feature             1..20
                         note = synthetic DNA
source                   1..20
                         mol_type = other DNA
                         organism = synthetic construct
SEQUENCE: 37
tgtaatcggg cggttaattc                                                  20

SEQ ID NO: 38            moltype = DNA  length = 19
FEATURE                  Location/Qualifiers
misc_feature             1..19
                         note = synthetic DNA
source                   1..19
                         mol_type = other DNA
                         organism = synthetic construct
SEQUENCE: 38
gccctttcag gcgatagag                                                   19

SEQ ID NO: 39            moltype = DNA  length = 20
FEATURE                  Location/Qualifiers
misc_feature             1..20
                         note = synthetic DNA
source                   1..20
                         mol_type = other DNA
                         organism = synthetic construct
SEQUENCE: 39
acggcgaaaa tcagcggaag                                                  20

SEQ ID NO: 40            moltype = DNA  length = 20
FEATURE                  Location/Qualifiers
misc_feature             1..20
                         note = synthetic DNA
source                   1..20
                         mol_type = other DNA
                         organism = synthetic construct
SEQUENCE: 40
tcactctccg tcggcagctg                                                  20

SEQ ID NO: 41            moltype = DNA  length = 72
FEATURE                  Location/Qualifiers
misc_feature             1..72
                         note = UTR1
source                   1..72
                         mol_type = other DNA
                         organism = synthetic construct
SEQUENCE: 41
aattcgccgg agggatatta aaatgaatgg aaaattgaaa catcttaatc atgctaagga      60
ggttttctaa tg                                                          72

SEQ ID NO: 42            moltype = AA  length = 237
FEATURE                  Location/Qualifiers
source                   1..237
                         mol_type = protein
                         organism = Escherichia coli
SEQUENCE: 42
MRKITQAISA VCLLFALNSS AVALASSPSP LNPGTNVARL AEQAPIHWVS VAQIENSLAG      60
RPPMAVGFDI DDTVLFSSPG FWRGKKTFSP ESEDYLKNPV FWEKMNNGWD EFSIPKEVAR     120
QLIDMHVRRG DAIFFVTGRS PTKTETVSKT LADNFHIPAT NMNPVIFAGD KPGQNTKSQW     180
LQDKNIRIFY GDSDNDITAA RDVGARGIRI LRASNSTYKP LPQAGAFGEE VIVNSEY       237

SEQ ID NO: 43            moltype = AA  length = 272
FEATURE                  Location/Qualifiers
source                   1..272
                         mol_type = protein
                         organism = Escherichia coli
SEQUENCE: 43
MARLAAFDMD GTLLMPDHHL GEKTLSTLAR LRERDITLTF ATGRHALEMQ HILGALSLDA      60
YLITGNGTRV HSLEGELLHR DDLPADVAEL VLYQQWDTRA SMHIFNDDGW FTGKEIPALL     120
QAFVYSGFRY QIIDVKKMPL GSVTKICFCG DHDDLTRLQI QLYEALGERA HLCFSATDCL    180
EVLPVGCNKG AALTVLTQHL GLSLRDCMAF GDAMNDREML VSVGSGFIMG NAMPQLRAEL    240
PHLPVIGHCR NQAVSHYLTH WLDYPHLPYS PE                                  272

SEQ ID NO: 44            moltype = AA  length = 355
FEATURE                  Location/Qualifiers
source                   1..355
                         mol_type = protein
```

```
                        organism = Escherichia coli
SEQUENCE: 44
MSQKYLFIDR DGTLISEPPS DFQVDRFDKL AFEPGVIPEL LKLQKAGYKL VMITNQDGLG    60
TQSFPQADFD GPHNLMMQIF TSQGVQFDEV LICPHLPADE CDCRKPKVKL VERYLAEQAM   120
DRANSYVIGD RATDIQLAEN MGITGLRYDR ETLNWPMIGE QLTRRDRYAH VVRNTKETQI   180
DVQVWLDREG GSKINTGVGF FDHMLDQIAT HGGFRMEINV KGDLYIDDHH TVEDTGLALG   240
EALKIALGDK RGICRFGFVL PMDECLARCA LDISGRPHLE YKAEFTYQRV GDLSTEMIEH   300
FFRSLSYTMG VTLHLKTKGK NDHHRVESLF KAFGRTLRQA IRVEGDTLPS SKGVL        355

SEQ ID NO: 45           moltype = AA   length = 266
FEATURE                 Location/Qualifiers
source                  1..266
                        mol_type = protein
                        organism = Escherichia coli
SEQUENCE: 45
MTEPLTETPE LSAKYAWFFD LDGTLAEIKP HPDQVVVPDN ILQGLQLLAT ASDGALALIS    60
GRSMVELDAL AKPYRFPLAG VHGAERRDIN GKTHIVHLPD AIARDISVQL HTVIAQYPGA   120
ELEAKGMAFA LHYRQAPQHE DALMTLAQRI TQIWPQMALQ QGKCVVEIKP RGTSKGEAIA   180
AFMQEAPFIG RTPVFLGDDL TDESGFAVVN RLGGMSVKIG TGATQASWRL AGVPDVWSWL   240
EMITTALQQK RENNRSDDYE SFSRSI                                       266

SEQ ID NO: 46           moltype = AA   length = 253
FEATURE                 Location/Qualifiers
source                  1..253
                        mol_type = protein
                        organism = Escherichia coli
SEQUENCE: 46
MRILLSNDDG VHAPGIQTLA KALREFADVQ VVAPDRNRSG ASNSLTLESS LRTFTFENGD    60
IAVQMGTPTD CVYLGVNALM RPRPDIVVSG INAGPNLGDD VIYSGTVAAA MEGRHLGFPA   120
LAVSLDGHKH YDTAAAVTCS ILRALCKEPL RTGRILNINV PDLPLDQIKG IRVTRCGTRH   180
PADQVIPQQD PRGNTLYWIG PPGGKCDAGP GTDFAAVDEG YVSITPLHVD LTAHSAQDVV   240
SDWLNSVGVG TQW                                                     253

SEQ ID NO: 47           moltype = AA   length = 191
FEATURE                 Location/Qualifiers
source                  1..191
                        mol_type = protein
                        organism = Escherichia coli
SEQUENCE: 47
MAKSVPAIFL DRDGTINVDH GYVHEIDNFE FIDGVIDAMR ELKKMGFALV VVTNQSGIAR    60
GKFTEAQFET LTEWMDWSLA DRDVDLDGIY YCPHHPQGSV EEFRQVCDCR KPHPGMLLSA   120
RDYLHIDMAA SYMVGDKLED MQAAVAANVG TKVLVRTGKP ITPEAENAAD WVLNSLADLP   180
QAIKKQQKPA Q                                                       191

SEQ ID NO: 48           moltype = AA   length = 219
FEATURE                 Location/Qualifiers
source                  1..219
                        mol_type = protein
                        organism = Escherichia coli
SEQUENCE: 48
MKLQGVIFDL DGVITDTAHL HFQAWQQIAA EIGISIDAQF NESLKGISRD ESLRRILQHG    60
GKEEGDFNSQE RAQLAYRKNL LYVHSLRELT VNAVLPGIRS LLADLRAQQI SVGLASVSLN   120
APTILAALEL REFFTFCADA SQLKNSKPDP EIFLAACAGL GVPPQACIGI EDAQAGIDAI   180
NASGMRSVGI GAGLTGAQLL LPSTESLTWP RLSAFWQNV                          219

SEQ ID NO: 49           moltype = AA   length = 271
FEATURE                 Location/Qualifiers
source                  1..271
                        mol_type = protein
                        organism = Escherichia coli
SEQUENCE: 49
MFSIQQPLLV FSDLDGTLLD SHSYDWQPAA PWLTRLREAN VPVILCSSKT SAEMLYLQKT    60
LGLQGLPLIA ENGAVIQLAE QWQEIDGFPR IISGISHGEI EHFKFTTFDD              120
VDDATIAEWT GLSRSQAALT QLHEASVTLI WRDSDERMAQ FTARLNELGL QFMQGARFWH   180
VLDASAGKDQ AANWIIATYQ QLSGKRPTTL GLGDGPNDAP LLEVMDYAVI VKGLNREGVH   240
LHDEDPARVW RTQREGPEGW REGLDHFFSA R                                  271

SEQ ID NO: 50           moltype = AA   length = 216
FEATURE                 Location/Qualifiers
source                  1..216
                        mol_type = protein
                        organism = Escherichia coli
SEQUENCE: 50
MRCKGFLFDL DGTLVDSLPA VERAWSNWAR RHGLAPEEVL AFIHGKQAIT SLRHFMAGKS    60
EADIAAEFTR LEHIEATETE GITALPGAIA LLSHLNKAGI PWAIVTSGSM PVARARHKIA   120
GLPAPEVFVT AERVKRGKPE PDAYLLGAQL LGLAPQECVV VEDAPAGVLS GLAAGCHVIA   180
VNAPADTPRL NEVDLVLHSL EQITVTKQPN GDVIIQ                             216

SEQ ID NO: 51           moltype = AA   length = 270
```

```
FEATURE                 Location/Qualifiers
source                  1..270
                        mol_type = protein
                        organism = Escherichia coli
SEQUENCE: 51
MAIKLIAIDM DGTLLLPDHT ISPAVKNAIA AARARGVNVV LTTGRPYAGV HNYLKELHME    60
QPGDYCITYN GALVQKAADG STVAQTALSY DDYRFLEKLS REVGSHFHAL DRTTLYTANR   120
DISYYTVHES FVATIPLVFC EAEKMDPNTQ FLKVMMIDEP AILDQAIARI PQEVKEKYTV   180
LKSAPYFLEI LDKRVNKGTG VKSLADVLGI KPEEIMAIGD QENDIAMIEY AGVGVAMDNA   240
IPSVKEVANF VTKSNLEDGV AFAIEKYVLN                                   270

SEQ ID NO: 52           moltype = AA  length = 238
FEATURE                 Location/Qualifiers
source                  1..238
                        mol_type = protein
                        organism = Escherichia coli
SEQUENCE: 52
MRFYRPLGRI SALTFDLDDT LYDNRPVILR TEREALTFVQ NYHPALRSFQ NEDLQRLRQA    60
VREAEPEIYH DVTRWRFRSI EQAMLDAGLS AEEEASAGAHA AMINFAKWRS RIDVPQQTHD  120
TLKQLAKKWP LVAITNGNAQ PELFGLGDYF EFVLRAGPHG RSKPFSDMYF LAAEKLNVPI   180
GEILHVGDDL TTDVGGAIRS GMQACWIRPE NGDLMQTWDS RLLPHLEISR LASLTSLI     238

SEQ ID NO: 53           moltype = AA  length = 199
FEATURE                 Location/Qualifiers
source                  1..199
                        mol_type = protein
                        organism = Escherichia coli
SEQUENCE: 53
MLYIFDLGNV IVDIDFNRVL GAWSDLTRIP LASLKKSFHM GEAFHQHERG EISDEAFAEA    60
LCHEMALPLS YEQFSHGWQA VFVALRPEVI AIMHKLREQG HRVVVLSNTN RLHTTFWPEE   120
YPEIRDAADH IYLSQDLGMR KPEARIYQHV LQAEGFSPSD TVFFDDNADN IEGANQLGIT   180
SILVKDKTTI PDYFAKVLC                                               199

SEQ ID NO: 54           moltype = AA  length = 222
FEATURE                 Location/Qualifiers
source                  1..222
                        mol_type = protein
                        organism = Escherichia coli
SEQUENCE: 54
MSTPRQILAA IFDMDGLLID SEPLWDRAEL DVMASLGVDI SRRNELPDTL GLRIDMVVDL    60
WYARQPWNGP SRQEVVERVI ARAISLVEET RPLLPGVREA VALCKEQGLL VGLASASPLH   120
MLEKVLTMFD LRDSFDALAS AEKLPYSKPH PQVYLDCAAK LGVDPLTCVA LEDSVNGMIA   180
SKAARMRSIV VPAPEAQNDP RFVLADVKLS SLTELTAKDL LG                      222

SEQ ID NO: 55           moltype = AA  length = 188
FEATURE                 Location/Qualifiers
source                  1..188
                        mol_type = protein
                        organism = Escherichia coli
SEQUENCE: 55
MYERYAGLIF DMDGTILDTE PTHRKAWREV LGHYGLQYDI QAMIALNGSP TWRIAQAIIE    60
LNQADLDPHA LAREKTEAVR SMLLDSVEPL PLVDVVKSWH GRRPMAVGTG SESAIAEALL   120
AHLGLRHYFD AVVAADHVKH HKPAPDTFLL CAQRMGVQPT QCVVFEDADF GIQAARAAGM   180
DAVDVRLL                                                           188

SEQ ID NO: 56           moltype = AA  length = 188
FEATURE                 Location/Qualifiers
source                  1..188
                        mol_type = protein
                        organism = Escherichia coli
SEQUENCE: 56
MSKAGASLAT CYGPVSADVI AKAENIRLLI LDVDGVLSDG LIYMGNNGEE LKAFNVRDGY    60
GIRCALTSDI EVAIITGRKA KLVEDRCATL GITHLYQGQS NKLIAFSDLL EKLAIAPENV   120
AYVGDDLIDW PVMEKVGLSV AVADAHPLLI PRADYVTRIA GGRGAVREVC DLLLLAQGKL   180
DEAKGQSI                                                           188

SEQ ID NO: 57           moltype = AA  length = 223
FEATURE                 Location/Qualifiers
source                  1..223
                        mol_type = protein
                        organism = Pseudomonas putida
SEQUENCE: 57
MRLRAVLFDM DGTLLDTAPD FIAICQAMLA ERGLPAVDDN LIRGVISGGA RAMVATAFAM    60
DPEADGFEAL RLEFLERYQR DCAVHSKLFE GMAELLADIE KGNLLWGVVT NKPVRFAEPI   120
MQQLGLAERS ALLICPDHVK NSKPDPEPLI LACKTLNLDP ASVLFVGDDL RDIESGRDAG   180
TRTAAVRYGY IHPEDNPNNW GADVVVDHPL ELRKVIDSAL CGC                    223

SEQ ID NO: 58           moltype = AA  length = 432
FEATURE                 Location/Qualifiers
```

```
source                  1..432
                        mol_type = protein
                        organism = Escherichia coli
SEQUENCE: 58
MKAILIPFLS LLIPLTPQSA FAQSEPELKL ESVVIVSRHG VRAPTKATQL MQDVTPDAWP    60
TWPVKLGWLT PRGGELIAYL GHYQRQRLVA DGLLAKKGCP QSGQVAIIAD VDERTRKTGE   120
AFAAGLAPDC AITVHTQADT SSPDPLFNPL KTGVCQLDNA NVTDAILSRA GGSIADFTGH   180
RQTAFRELER VLNFPQSNLC LKREKQDESC SLTQALPSEL KVSADNVSLT GAVSLASMLT   240
EIFLLQQAQG MPEPGWGRIT DSHQWNTLLS LHNAQFYLLQ RTPEVARSRA TPLLDLIKTA   300
LTPHPPQKQA YGVTLPTSVL FIAGHDTNLA NLGGALELNW TLPGQPDNTP PGGELVFERW   360
RRLSDNSQWI QVSLVFQTLQ QMRDKTPLSL NTPPGEVKLT LAGCEERNAQ GMCSLAGFTQ   420
IVNEARIPAC SL                                                      432

SEQ ID NO: 59           moltype = AA   length = 252
FEATURE                 Location/Qualifiers
source                  1..252
                        mol_type = protein
                        organism = Escherichia coli
SEQUENCE: 59
MNKFEDIRGV AFDLDGTLVD SAPGLAAAVD MALYALELPV AGEERVITWI GNGADVLMER    60
ALTWARQERA TQRKTMGKPP VDDDIPAEEQ VRILRKLFDR YYGEVAEEGT FLFPHVADTL   120
GALQAKGLPL GLVTNKPTPF VAPLLEALDI AKYFSVVIGG DDVQNKKPHP DPLLLVAERM   180
GIAPQQMLFV GDSRNDIQAA KAAGCPSVGL TYGYNYGEAI DLSQPDVIYQ SINDLLPALG   240
LPHSENQESK ND                                                      252

SEQ ID NO: 60           moltype = AA   length = 322
FEATURE                 Location/Qualifiers
source                  1..322
                        mol_type = protein
                        organism = Escherichia coli
SEQUENCE: 60
MPNITWCDLP EDVSLWPGLP LSLSGDEVMP LDYHAGRSGW LLYGRGLDKQ RLTQYQSKLG    60
AAMVIVAAWC VEDYQVIRLA GSLTARATRL AHEAQLDVAP LGKIPHLRTP GLLVMDMDST   120
AIQIECIDEI AKLAGTGEMV AEVTERAMRG ELDFTASLRS RVATLKGADA NILQQVRENL   180
PLMPGLTQLV LKLETLGWKV AIASGGFTFF AEYLRDKLRL TAVVANELEI MDGKFTGNVI   240
GDIVDAQYKA KTLTRLAQEY EIPLAQTVAI GDGANDLPMI KAAGLGIAYH AKPKVNEKAE   300
VTIRHADLMG VFCILSGSLN QK                                           322

SEQ ID NO: 61           moltype = AA   length = 250
FEATURE                 Location/Qualifiers
source                  1..250
                        mol_type = protein
                        organism = Escherichia coli
SEQUENCE: 61
MTIKNVICDI DGVLMHDNVA VPGAAEFLHG IMDKGLPLVL LTNYPSQTGQ DLANRFATAG    60
VDVPDSVFYT SAMATADFLR RQEGKKAYVV GEGALIHELY KAGFTITDVN PDFVIVGETR   120
SYNWDMMHKA AYFVANGARF IATNPDTHGR GFYPACGALC AGIEKISGRK PFYVGKPSPW   180
IIRAALNKMQ AHSEETVIVG DNLRTDILAG FQAGLETILV LSGVSSLDDI DSMPFRPSWI   240
YPSVAEIDVI                                                         250

SEQ ID NO: 62           moltype = AA   length = 272
FEATURE                 Location/Qualifiers
source                  1..272
                        mol_type = protein
                        organism = Escherichia coli
SEQUENCE: 62
MTTRVIALDL DGTLLTPKKT LLPSSIEALA RAREAGYQLI IVTGRHHVAI HPFYQALALD    60
TPAICCNGTY LYDYHAKTVL EADPMPVIKA LQLIEMLNEH HIHGLMYVDD AMVYEHPTGH   120
VIRTSNWAQT LPPEQRPTFT QVASLAETAQ QVNAVWKFAL THDDLPQLQH FGKHVEHELG   180
LECEWSWHDQ VDIARGGNSK GKRLTKWVEA QGWSMENVVA FGDNFNDISM LEAAGTGVAM   240
GNADDAVKAR ANIVIGDNTT DSIAQFIYSH LI                                272

SEQ ID NO: 63           moltype = AA   length = 271
FEATURE                 Location/Qualifiers
source                  1..271
                        mol_type = protein
                        organism = Escherichia coli
SEQUENCE: 63
MSVKVIVTDM DGTFLNDAKT YNQPRFMAQY QELKKRGIKF VVASGNQYYQ LISFFPELKD    60
EISFVAENGA LVYEHGKQLF HGELTRHESR IVIGELLKDK QLNFVACGLQ SAYVSENAPE   120
AFVALMAKHY HRLKPVKDYQ EIDDVLFKFS LNLPDEQIPL VIDKLHVALD GIMKPVTSGF   180
GFIDLIIPGL HKANGISRLL KRWDLSPQNV VAIGDSGNDA EMLKMARYSF AMGNAAENIK   240
QIARYATDDN NHEGALNVIQ AVLDNTSPFN S                                 271

SEQ ID NO: 64           moltype = AA   length = 561
FEATURE                 Location/Qualifiers
source                  1..561
                        mol_type = protein
                        organism = Escherichia coli
```

```
SEQUENCE: 64
MNINVAELLN GNYILLLFVV LALGLCLGKL RLGSIQLGNS IGVLVVSLLL GQQHFSINTD    60
ALNLGFMLFI FCVGVEAGPN FFSIFFRDGK NYLMLALVMV GSALVIALGL GKLFGWDIGL   120
TAGMLAGSMT STPVLVGAGD TLRHSGMESR QLSLALDNLS LGYALTYLIG LVSLIVGARY   180
LPKLQHQDLQ TSAQQIARER GLDTDANRKV YLPVIRAYRV GPELVAWTDG KNLRELGIYR   240
QTGCYIERIR RNGILANPDG DAVLQMGDEI ALVGYPDAHA RLDPSFRNGK EVFDRDLLDM   300
RIVTEEVVVK NHNAVGKRLA QLKLTDHGCF LNRVIRSQIE MPIDDNVVLN KGDVLQVSGD   360
ARRVKTIADR IGFISIHSQV TDLLAFCAFF VIGLMIGMIT FQFSTFSFGM GNAAGLLFAG   420
IMLGFMRANH PTFGYIPQGA LSMVKEFGLM VFMAGVGLSA GSGINNGLGA IGGQMLIAGL   480
IVSLVPVVIC FLFGAYVLRM NRALLFGAMM GARTCAPAME IISDTARSNI PALGYAGTYA   540
IANVLLTLAG TIIVMVWPGL G                                            561

SEQ ID NO: 65           moltype = AA   length = 199
FEATURE                 Location/Qualifiers
source                  1..199
                        mol_type = protein
                        organism = Escherichia coli
SEQUENCE: 65
MKQSHFFAHL SRLKLINRWP LMRNVRTENV SEHSLQVAMV AHALAAIKNR KFGGNVNAER    60
IALLAMYHDA SEVLTGDLPT PVKYFNSQIA QEYKAIEKIA QQKLVDMVPE ELRDIFAPLI   120
DEHAYSDEEK SLVKQADALC AYLKCLEELA AGNNEFLLAK TRLEATLEAR RSQEMDYFME   180
IFVPSFHLSL DEISQDSPL                                                199

SEQ ID NO: 66           moltype = AA   length = 221
FEATURE                 Location/Qualifiers
source                  1..221
                        mol_type = protein
                        organism = Escherichia coli
SEQUENCE: 66
MSRIEAVFFD CDGTLVDSEV ICSRAYVTMF QEFGITLDPE EVFKRFPKGVK LYEIIDIVSL    60
EHGVTLAKTE AEHVYRAEVA RLFDSELEAI EGAGALLSAI TAPMCVVSNG PNNKMQHSMG   120
KLNMLHYFPD KLFSGYDIQR WKPDPALMPH AAKAMNVNVE NCILVDDSVA GAQSGIDAGM   180
EVFYFCADPH NKPIVHPKVT TFTHLSQLPE LWKARGWDIT A                      221

SEQ ID NO: 67           moltype = AA   length = 604
FEATURE                 Location/Qualifiers
source                  1..604
                        mol_type = protein
                        organism = Escherichia coli
SEQUENCE: 67
MSKISDLNYS QHITLADNFK QKSEVLNTWR VGMNDFARIA GGQDNRRNIL SPGAFLEFLA    60
KIFTLYVDF SKRSNEAGRN MMAHIKSSSY SKDTNGNEKM KFYMNNPVGE RADSPKVIIE   120
ISLSTITTMG TRQGHTAIIF PQPDGSTNRY EGKSFERKDE SSLHLITNKV LACYQSEANK   180
KIARLLNNNQ ELNNLQKLNN LQKLNNLLKL NNIQGLNNPQ ELNNPQNLND SQELNNSQEL   240
NSPQELNDPQ ELNNSQDLNN SKVSCTVSVD STITGLLKEP LNNALLAIRN EHLLLMPHVC   300
DESISYLLGE KGILEEIDKL YALNDHGIDN DKVGNNEIND IKVNLSHILI DSLDDAKVNL   360
TPVIDSILET FSKSPYINDV RILDWCFNKS MQYFDDTKKI KHACSVINHI NLRSDQSKIA   420
ETLFFNLDKE PYKNSPELQG LIWNKLVVYV NEFNLSNREK TNLIQRLFDN VESIFNEVPV   480
SILVNDIFMN DFFMKNPEMI NWYFPQLLKS YEGEKIYFDN LKYDLNDNDK ESNKEILKNQ   540
PDNVIKEKLN NEYKLRFRMM QTILQSRVNV LPYINEQRLN KLNPPENLRI AIEHFGWKNR   600
PITA                                                               604

SEQ ID NO: 68           moltype = AA   length = 225
FEATURE                 Location/Qualifiers
source                  1..225
                        mol_type = protein
                        organism = Escherichia coli
SEQUENCE: 68
MKWDWIFFDA DETLFTFDSF TGLQRMFLDY SVTFTAEDFQ DYQAVNKPLW VDYQNGAITS    60
LQLQHGRFES WAERLNVEPG KLNEAFINAM AEICTPLPGA VSLLNAIRGN AKIGIITNGF   120
SALQQVRLER TGLRDYFDLL VISEEVGVAK PNKKIFDYAL EQAGNPDRSR VLMVGDTAES   180
DILGGINAGL ATCWLNAHHR EQPEGIAPTW TVSSLHELEQ LLCKH                  225

SEQ ID NO: 69           moltype = AA   length = 222
FEATURE                 Location/Qualifiers
source                  1..222
                        mol_type = protein
                        organism = Escherichia coli
SEQUENCE: 69
MHINIAWQDV DTVLLDMDGT LLDLAFDNYF WQKLVPETWG AKNGVTPQEA MEYMRQQYHD    60
VQHTLNWYCL DYWSEQLGLD ICAMTTEMGP RAVLREDTIP FLEALKASGK QRILLTNAHP   120
HNLAVKLEHT GLDAHLDLLL STHTFGYPKE DQRLWHAVAE ATGLKAERTL FIDDSEAILD   180
AAAQFGIRYC LGVTNPDSGI AEKQYQRHPS LNDYRRLIPS LM                     222

SEQ ID NO: 70           moltype = AA   length = 421
FEATURE                 Location/Qualifiers
source                  1..421
                        mol_type = protein
                        organism = Escherichia coli
```

```
SEQUENCE: 70
MASTFTSDTL PADHKAAIRQ MKHALRAQLG DVQQIFNQLS DDIATRVAEI NALKAQGDAV    60
WPVLSYADIK AGHVTAEQRE QIKRRGCAVI KGHFPREQAL GWDQSMLDYL DRNRFDEVYK   120
GPGDNFFGTL SASRPEIYPI YWSQAQMQAR QSEEMANAQS FLNRLWTFES DGKQWFNPDV   180
SVIYPDRIRR RPPGTTSKGL GAHTDSGALE RWLLPAYQRV FANVFNGNLA QYDPWHAAHR   240
TEVEEYTVDN TTKCSVFRTF QGWTALSDML PGQGLLHVVP IPEAMAYVLL RPLLDDVPED   300
ELCGVAPGRV LPVSEQWHPL LIEALTSIPK LEAGDSVWWH CDVIHSVAPV ENQQGWGNVM   360
YIPAAPMCEK NLAYAHKVKA ALEKGASPGD FPREDYETNW EGRFTLADLN IHGKRALGMD   420
V                                                                  421

SEQ ID NO: 71           moltype = AA  length = 246
FEATURE                 Location/Qualifiers
source                  1..246
                        mol_type = protein
                        organism = Saccharomyces cerevisiae
SEQUENCE: 71
MAEFSADLCL FDLDGTIVST TVAAEKAWTK LCYEYGVDPS ELFKHSHGAR TQEVLRRFFP    60
KLDDTDNKGV LALEKDIAHS YLDTVSLIPG AENLLLSLDV DTETQKKLPE RKWAIVTSGS   120
PYLAFSWFET ILKNVGKPKV FITGFDVKNG KPDPEGYSRA RDLLRQDLQL TGKQDLKYVV   180
FEDAPVGIKA GKAMGAITVG ITSSYDKSVL FDAGADYVVC DLTQVSVVKN NENGIVIQVN   240
NPLTRA                                                             246

SEQ ID NO: 72           moltype = AA  length = 272
FEATURE                 Location/Qualifiers
source                  1..272
                        mol_type = protein
                        organism = Bacillus subtilis
SEQUENCE: 72
MRIMASHDTP VSPAGILIDL DGTVFRGNEL IEGAREAIKT LRRMGKKIVF LSNRGNISRA    60
MCRKKLLGAG IETDVNDIVL SSSVTAAFLK KHYRFSKVWV LGEQGLVDEL RLAGVQNASE   120
PKEADWLVIS LHETLTYDDL NQAFQAAAGG ARIIATNKDR SFPNEDGNAI DVAGMIGAIE   180
TSAQAKTELV VGKPSWLMAE AACTAMGLSA HECMIIGDSI ESDIAMGKLY GMKSALVLTG   240
SAKQGEQRLY TPDYVLDSIK DVTKLAEEGI LI                                 272

SEQ ID NO: 73           moltype =    length =
SEQUENCE: 73
000

SEQ ID NO: 74           moltype =    length =
SEQUENCE: 74
000

SEQ ID NO: 75           moltype =    length =
SEQUENCE: 75
000

SEQ ID NO: 76           moltype =    length =
SEQUENCE: 76
000

SEQ ID NO: 77           moltype =    length =
SEQUENCE: 77
000

SEQ ID NO: 78           moltype = AA  length = 272
FEATURE                 Location/Qualifiers
source                  1..272
                        mol_type = protein
                        organism = Shigella flexneri
SEQUENCE: 78
MARLAAFDMD GTLLMPDHHL GEKTLSTLAR LRERDITLTF ATGRHALEMQ HILGALSLDA    60
YLITGNGTRV HSLEGELLHR DDLPADVAEL VLYQQWDTRA SMHIFNDDGW FTGKEIPALL   120
QAFVYSGFRY QIIDVKKMPL GSVTKICFCG DHDDLTRLQI QLYEALGERA HLCFSATDCL   180
EVLPVGCNKG AALTVLTQHL DLSLRDCMAF GDAMNDREML VSVGSGFIMG NAMPQLRAEL   240
PHLPVIGHCR NQAVSHYLTH WLDYPHLPYS PE                                 272

SEQ ID NO: 79           moltype = AA  length = 272
FEATURE                 Location/Qualifiers
source                  1..272
                        mol_type = protein
                        organism = Shigella boydii
SEQUENCE: 79
MARLAAFDMD GTLLMPDHHL GEKTLSTLAR LRERDITLTF ATGRHALEMQ HILGALSLDA    60
YLITGNGTRV HSLEGELLHR DDLPADVAEL VLYQQWDTRA SMHIFNDDGW FTGKEIPALL   120
QAFVYNGFRY QIIDVKKMPL GSVTKICFCG DHDDLTRLQI QLYEALGERA HLCFSATDCL   180
EVLPVGCNKG AALTVLTQHL GLSLRDCMAF GDAMNDREML GSVGSGFIMG NAMPQLRAEL   240
PHLPVIGHCR NQAVSHYLTH WLDYPHLPYS PE                                 272

SEQ ID NO: 80           moltype = AA  length = 272
```

| FEATURE | Location/Qualifiers |
| --- | --- |
| source | 1..272 |
| | mol_type = protein |
| | organism = Escherichia fergusonii |

SEQUENCE: 80
```
MARLAAFDMD GTLLMPDHHL GEKTLSTLAR LRERDITLTF ATGRHALEMQ HILGALSLDA  60
YLITGNGTRV HSLEGELLHR DDLPADVAEL VLYQQWDTRA SMHIFNDDGW FTGKEIPALL 120
QAFVYSGFRY QIIDVKKMPL DRVTKICFCG DHDDLTRLQI QLHEALGERA HLCFSATDCL 180
EVLPVGCNKG AALTVLTQHL GLSLRECMAF GDAMNDREML GSVGSGFIMG NAMPQLRAEL 240
PHLPVIGHCR NQAVSHYLTH WLDYPHLPYS PE                             272
```

| SEQ ID NO: 81 | moltype = AA length = 245 |
| --- | --- |
| FEATURE | Location/Qualifiers |
| source | 1..245 |
| | mol_type = protein |
| | organism = Staphylococcus aureus |

SEQUENCE: 81
```
MARLAAFDMD GTLLVPDHHL GEKTLSTLAR LRERDITLTF ATGRHALEMQ HILGALSLDA  60
YLITGNGTRV HSLEGELLHR DDLPADVAEL VLYQQWDTRA SMHIFNDDGW FTGKEIPALL 120
QAFVYSGFRY QIIDVKKMPL GSVTKICFCG DHDDLTRLQI QLYEALGERA HLCFSATDCL 180
EVLPVGCNKG AALTVLTQHL GLSLRDCTAF GDAMNDREML VSVGSGFIMG NAMPQLRAEL 240
PHLPV                                                          245
```

| SEQ ID NO: 82 | moltype = AA length = 272 |
| --- | --- |
| FEATURE | Location/Qualifiers |
| REGION | 1..272 |
| | note = Escherichia albertii |
| source | 1..272 |
| | mol_type = protein |
| | organism = unidentified |

SEQUENCE: 82
```
MARLAAFDMD GTLLMPDHHL GEKTLSTLAR LRDRDITLTF ATGRHALEMR HILGTFALDA  60
YLITGNGTRV HSQEGDLLYR DDLPADVAER VLHQKWDTQA SMHIFNDDGW FTGQEMPSLL 120
QAFVYSGFRY QIIDVKKMPL DRVTKICFCG DHDDLTRLQI QLNEALGDRA HLCFSAINCL 180
EVLPVGCNKG AALAVLADYL GFSLRDCMAF GDAMNDREML GSVGNGFIMG NAMPQLLAEL 240
PHLPVIGHCR NQAVSHYLTH WLDNPHLPYS PE                             272
```

| SEQ ID NO: 83 | moltype = AA length = 272 |
| --- | --- |
| FEATURE | Location/Qualifiers |
| source | 1..272 |
| | mol_type = protein |
| | organism = Citrobacter amalonaticus |

SEQUENCE: 83
```
MARLAAFDMD GTLLMPNHLL GDETLSTLAR LRERDITLTF ATGRHVLEMR HILGTFSLDA  60
FLITGNGTRI HSLEGEVLHR QDLEPAVAEI VLHQRWDTQA SMHIFNDNGW FTGQEIPEML 120
HAHVYSGFRY QIVDVARIPA DRVTKVCFCG DHDDLTRLKI QLEEVLGARA HLCFSAVDCL 180
EVLPVGCNKG SALEVLSGHL GLSLAECMAF GDAMNDREML GSVGRGLIMG NAMPQLIAEL 240
PHLPVIGHCR NQAVSHFLTH WLDYPNLPYS PE                             272
```

| SEQ ID NO: 84 | moltype = AA length = 272 |
| --- | --- |
| FEATURE | Location/Qualifiers |
| source | 1..272 |
| | mol_type = protein |
| | organism = Salmonella enterica |

SEQUENCE: 84
```
MARLAAFDMD GTLLMPDHHL GKETLATLAR LRERDITLTF ATGRHVLEMR HILGTLSLDA  60
YLITGNGTRI HSLEGDVLHR QDLDPQVADT VMHHAWDTRA SMHVFNDNGW FTGQEIPALL 120
QAHVYSGFRY QVIDIKSIPA HQVTKICFCG DHDDLIRLRI QLNEALEERA HLCFSAVDCL 180
EVLPLGCNKG SALAVLSNHL GLSLADCMAF GDAMNDREML GSVGRGLIMG NAMPQLIAAL 240
PHLSVIGHCG NQAVSHFLTH WLDNPHLPYS PE                             272
```

| SEQ ID NO: 85 | moltype = AA length = 220 |
| --- | --- |
| FEATURE | Location/Qualifiers |
| source | 1..220 |
| | mol_type = protein |
| | organism = Escherichia coli |

SEQUENCE: 85
```
LGALSLDAYL ITGNGTRVHS LEGELLHRDD LPADVAELVL YQQWDTRASM HIFNDDGWFT  60
GKEIPALLQA FVYSGFRYQI IDVKKMPLGS VTKICFCGDH DDLTRLQIQL YEALGERAHL 120
CFSATDCLEV LPVGCNKGAA LTVLTQHLGL SLRDCMAFGD AMNDREMLGS VGSGFIMGNA 180
MPQLRAELPH LPVIGHCRNQ AVSHYLTHWL DYPHLPYSPE                     220
```

| SEQ ID NO: 86 | moltype = AA length = 355 |
| --- | --- |
| FEATURE | Location/Qualifiers |
| source | 1..355 |
| | mol_type = protein |
| | organism = Shigella flexneri |

SEQUENCE: 86
```
MSQKYLFIDR DGTLISEPPS DFQVDRFDKL AFEPGVIPEL LKLQKAGYKL VMITNQDGLG  60
```

```
TQSFPQADFD GPHNLMMQIF TSQGVQFDEV LICPHLPADE CDCRKPKVKL VERYLAEQAM    120
DRANSYVIGD RATDIQLAEN MGITGLRYDR ETLNWPMIGE QLTKRDRYAH VVRNTKETQI    180
DVQVWLDREG GSKINTGVGF FDHMLDQIAT HGGFRMEINV KGDLYIDDHH TVEDTGLALG    240
EALKIALGDK RGICRFGFVL PMDECLARCA LDISGRPHLE YKAEFTYQRV GDLSTEMIEH    300
FFRSLSYTMG VTLHLKTKGK NDHHRVESLF KAFGRTLRQA MRVEGDTLPS SKGVL         355

SEQ ID NO: 87            moltype = AA   length = 355
FEATURE                  Location/Qualifiers
source                   1..355
                         mol_type = protein
                         organism = Escherichia albertii
SEQUENCE: 87
MSQKYLFIDR DGTLISEPPS DFQVDRFDKL AFEPGVIPEL LKLQKAGYKL VMITNQDGLG    60
TQSFPQADFD GPHNLMMQIF TSQGVQFDEV LICPHLPADE CDCRKPKVKL VERYLAEQAM    120
DRANSYVIGD RATDIQLAEN MGITGLRYDR ETLNWPMIGE QLTKRDRYAH VVRNTKETQI    180
DVQVWLDREG DSKINTGVGF FDHMLDQIAT HGGFRMEINV KGDLYIDDHH TVEDTGLALG    240
EALKIALGDK RGICRFGFVL PMDECLARCA MDISGRPHLE YKAEFTYQRV GDLSTEMIEH    300
FFRSLSYTMG VTLHLKTKGK NDHHRVESLF KAFGRTLRQA IRVEGDTLPS SKGVL         355

SEQ ID NO: 88            moltype = AA   length = 355
FEATURE                  Location/Qualifiers
source                   1..355
                         mol_type = protein
                         organism = Shigella flexneri
SEQUENCE: 88
MSQKYLFIDR DGTLISEPPS DFQVDRFDKL AFEPGVIPEL LKLQKAGYKL VMITNQDGLG    60
TQSFPQADFD GPHNLMMQIF TSQGVQFDEV LICPHLPADE CDCRKPKVKL VEGYLAEQAM    120
DRANSYVIGD RATDIQLAEN MGINGLRYDR ETLNWPMIGE QLTKRDRYAH VVRNTKETQI    180
DVQVWLDREG GSKINTGVGF FDHMLDQIAT HGGFRMEINV KGDLYIDDHH TVEDTGLALG    240
EALKIALGDK RGICRFGFVL PMDECLARCA LDISGRPHLE YKAEFTYQRV GDLSTEMIEH    300
FFRSLSYTMG VTLHLKTKGK NDHHRVESLF KAFGRTLRQA LRVEGDTLPS SKGVL         355

SEQ ID NO: 89            moltype = AA   length = 355
FEATURE                  Location/Qualifiers
source                   1..355
                         mol_type = protein
                         organism = Shigella sonnei
SEQUENCE: 89
MSQKYLFIDR DGTLISEPPS DFQVDRFDKL AFEPGVIPEL LKLQKAGYKL VMITNQDGLG    60
TQSFPQADFD GPHNLMMQIF TSQGVQFDEV LICPPLPADE CDCRKPKVKL VERYLAEQAM    120
DRANSYVIGD RATDIQLAEN MGINGLRYDR EILNWPMIGE QLTKRDRYAH VVRNTKETQI    180
DVQVWLDREG GSKINTGVGF FDHMLDQIAT HGGFRMEINV KGDLYIDDHH TVEDTGLALG    240
EALKMALGDK RGICRFGFVL PMDECLARCA LDISGRPHLE YKAEFTYQRV GDLSTEMIEH    300
FFRSLSYTMG VTLHLKTKGK NDHHRVESLF KAFGRTLRQA IRVEGDTLPS SKGVL         355

SEQ ID NO: 90            moltype = AA   length = 355
FEATURE                  Location/Qualifiers
source                   1..355
                         mol_type = protein
                         organism = Escherichia coli
SEQUENCE: 90
MSQKYLFIDR DGTLISEPPS DFQVDRFDKL AFEPGVIPQL LKLQKAGYKL VMITNQDGLG    60
TQSFPQADFD GPHNLMMQIF TSQGVQFDEV LICPHLPSDE CDCRKPKVKL VERYLAEQAM    120
DRANSYVIGD RATDIQLAEN MGINGLRYDR ETLNWPMIGE QLIKRDRYAH VVRNTKETQI    180
DVQVWLDREG GSKINTGVGF FDHMLDQIAT HGGFRMEINV KGDLYIDDHH TVEDTGLALG    240
EALKIALGDK RGICRFGFVL PMDECLARCA LDISGRPHLE YKAEFTYQRV GDLSTEMIEH    300
FFRSLSYTMG VTLHLKTKGK NDHHRVESLF KAFGRTLRQA IRVEGDTLPS SKGVL         355

SEQ ID NO: 91            moltype = AA   length = 355
FEATURE                  Location/Qualifiers
source                   1..355
                         mol_type = protein
                         organism = Shigella dysenteriae
SEQUENCE: 91
MSQKYLFIDR DGTLISEPPS DFQVDRFDKL AFEPGVIPEL LKLQKAGYKL VMITNQDGLG    60
TQSFPQADFD GPHNLMMQIF TSQGVQFDEV LICPHLPADE CDCRKPKVKL VERYLAEQAM    120
DRANSYVIGD RATDIQLAEN MGINGLRYDC EILSWPMIGE QLTKRDRYAH VVRNTKETQI    180
DVRVWLDREG GSKINTGVGF FDHMLDQIAT HGGFRMEINV KGDLYIDDHH TVEDTGLALG    240
EALKMALGDK RGICRFGFVL PMDECLARCA LDISGRPHLE YKAEFTYQRV GDLSTEMIEH    300
FFRSLSYTMG VTLHLKTKGK NDHHRVESLF KAFGRTLRQA IRVEGDTLPS SKGVL         355

SEQ ID NO: 92            moltype = AA   length = 355
FEATURE                  Location/Qualifiers
source                   1..355
                         mol_type = protein
                         organism = Escherichia marmotae
SEQUENCE: 92
MSQKYLFIDR DGTLISEPPS DFQVDRFDKL AFEPGVIPEL LKLQKAGYKL VMITNQDGLG    60
TQRFPQADFD GPHNLMMQIF TSQGVQFDEV LICPHLPDDE CDCRKPKVKL VERYLAEQAM    120
```

```
DRASSYVIGD RATDIQLAEN MGINGLRYNR ETLNWPMIGE QLTKRNRYAH VVRNTKETQI   180
DVQVWLDREG GSKINTGVGF FDHMLDQIAT HGGFRMEINV KGDLYIDDHH TVEDTGLALG   240
EALKIALGDK RGICRFGFVL PMDECLARCA LDISGRPHLE YKAEFTYQRV GDLSTEMIEH   300
FFRSLSYTMG VTLHLKTKGK NDHHRVESLF KAFGRTLRQA IRVEGDTLPS SKGVL        355

SEQ ID NO: 93              moltype = AA   length = 355
FEATURE                    Location/Qualifiers
source                     1..355
                           mol_type = protein
                           organism = Salmonella bongori
SEQUENCE: 93
MSQKYLFIDR DGTLISEPPS DFQVDRFDKL AFEPEVIPVL LKLQKAGFKL VMITNQDGLG   60
TQSFPQADFD GPHNLMMQVF TSQGVHFDEV LICPHLPADE CDCRKPKIKL VERYLAEQAM   120
DSANSYVIGD RATDVQLADN MGITGLRYHR ETLNWSMIGE QLTKRDRYAH VIRNTKETQI   180
DVRVWLDREG NSKINTGVGF FDHMLDQIAT HGGFRMDVTV KGDLYIDDHH TVEDTGLALG   240
EALKLALGDK RGICRFGFVL PMDECLARCA LDISGRPHLE YKAEFTYQRV GDLSTEMIEH   300
FFRSLSYTMG VTLHLKTKGK NDHHRVESLF KAFGRTLRQA IRVEGDTLPS SKGVL        355

SEQ ID NO: 94              moltype = AA   length = 266
FEATURE                    Location/Qualifiers
source                     1..266
                           mol_type = protein
                           organism = Shigella sonnei
SEQUENCE: 94
MTEPLTETPE LSAKYAWFFD LDGTLAEIKP HPDQVVVPDN ILQGLQLLAT ASDGALALIS   60
GRSMVELDAL AKPYRFPPLAG VHGAERRDIN GKTHIVHLPD AIARDISVQL HTVIAQYPGA   120
ELEAKGMAFA LHYRQAPQHE DALMTLAQRI TQIWPQMALQ QGKCVVEIKP RGTSKGEAIA   180
AFMQEAPFIG RTPVFLGDDL TDESGFAVVN RLGGMSVKIG TGATQASWRL AGVPDVWSWL   240
EMISTALQQK RENNRSDDYE SFSRSI                                       266

SEQ ID NO: 95              moltype = AA   length = 266
FEATURE                    Location/Qualifiers
source                     1..266
                           mol_type = protein
                           organism = Escherichia coli
SEQUENCE: 95
MTEPLTETPE LSAKYAWFFD LDGTLAEIKP HPDQVVVPDN ILQGLQLLAT ASDGALALIS   60
GRSMVELDAL AKPYRFPLAG VHGAERRDIN GKTHIVHLPD AIARDISVQL HTVIAQYPGA   120
ELEAKGMAFA LHYRQAPQHE DALMTLAQRI TQIWPQMALQ QGKCVVEIKP RGTSKGEAIA   180
AFMQEAPFIG RTPVFLGDDL TDESGFAVVN RLGGMSIKIG TGATQASWRL AGVPDVWSWL   240
EMITTALQQK RENNRSDDYE SFSRSI                                       266

SEQ ID NO: 96              moltype = AA   length = 266
FEATURE                    Location/Qualifiers
source                     1..266
                           mol_type = protein
                           organism = Shigella flexneri
SEQUENCE: 96
MTEPLTETPE LSAKYAWFFD LDGTLAEIKP HPDQVVVPDN ILQGLQLLAT ASDGALALIS   60
GRSMVELDAL AKPYRFPLAG VHGAERRDIN GKTHIVHLPD AIARDISVQL HTVIAQYPGA   120
ELEAKGMAFA LHYRQAPQHE DALMTLAQRI TQIWPQMALQ QGKCVVEIKP RGTSKGEAIA   180
AFMQEAPFIG RTPVFLGDDL TDESGFAVVN RLGGMSVKIG TGATQASWRL AGVPDVWSWL   240
KMITAALQQK RENNRSDDYE SFSRSI                                       266

SEQ ID NO: 97              moltype = AA   length = 265
FEATURE                    Location/Qualifiers
source                     1..265
                           mol_type = protein
                           organism = Escherichia albertii
SEQUENCE: 97
MTEPLTALPE LSAKYAWFFD LDGTLAEIKP HPDQVAVPDK ILQGLQRLAT ISHGALALIS   60
GRSMVELDAL VNPYRFPLAG VHGAERRDIN GKTHIVHLPK AMARDICVQL HMAIARFPGA   120
ELEEKGMAFA LHYRQVPQYE DALLTLARHI TQTWPQMVLQ QGKCVVEIKP GGTSKGEAIV   180
AFMQETPFIG RKPVFLGDDL TDESGFAVVN RLGGISVKIG TGATQASWRM AGVPDVWRWL   240
EMITHALQKR ANDRSDNDEP FSRSI                                        265

SEQ ID NO: 98              moltype = AA   length = 267
FEATURE                    Location/Qualifiers
source                     1..267
                           mol_type = protein
                           organism = Escherichia fergusonii
SEQUENCE: 98
MTKPLTEAPE LSAKYAWFFD LDGTLAEIKP HPDQVAIPDA ILQGLQQLAV HSDGALALIS   60
GRSMVELDTL AKPYRFPLAG VHGAERRDIN GKTHIVRLPD AMVRDISVQL HTTLAGLTGV   120
EIEEKGMAFA LHYRQAPQHE ALLFTLAQRI TQIWPQMALQ QGKCVVEIKP RGTCKGDAIA   180
EFMQETPFVG RIPIFWGDDL TDESGFAVVN QAGGISVKIG AGETQAKWRL AGVPDVWRWL   240
AVITNSLQEQ KLEENRSDDY ESFSRSI                                      267

SEQ ID NO: 99              moltype = AA   length = 191
```

```
FEATURE              Location/Qualifiers
source               1..191
                     mol_type = protein
                     organism = Escherichia fergusonii
SEQUENCE: 99
MAKSVPAIFL DRDGTINVDH GYVHEIDNFE FIDGVIDAMR ELKKMGFALV VVTNQSGIAR    60
GKFTEAQFET LTEWMDWSLA DRDVDLDGIY YCPHHPQGSV EEFRQVCDCR KPHPGMLLSA   120
RDYLHIDMAA SYMVGDKLED MQAATAANVG TKVLVRTGKP ITPEAENAAD WVLNSLADLP   180
QAIKKQQKPA Q                                                        191

SEQ ID NO: 100       moltype = AA  length = 191
FEATURE              Location/Qualifiers
source               1..191
                     mol_type = protein
                     organism = Shigella sonnei
SEQUENCE: 100
MAKSVPAIFL DRDGTINVDH GYVHEIDNFE FIDGVIDAMR ELKKMGFALV VVTNQSGIAR    60
GKFTEAQFET LTEWMDWSLA DRDVDLDGIY YCPHHPQGSV EEFRQVCDCR KPHPGMLLSA   120
RDYLHIDMAA SYMVGDKLED MQAAVAANVG TKVLVRTGKP ITPEAENAAD WMLNSLADLP   180
QAIKKQQKPA Q                                                        191

SEQ ID NO: 101       moltype = AA  length = 191
FEATURE              Location/Qualifiers
source               1..191
                     mol_type = protein
                     organism = Escherichia coli
SEQUENCE: 101
MAKSVPAIFL DRDGTINVDH GYVHEIDNFE FIDGVIDAMR ELKKMGFALV VVTNQSGIAR    60
GKFTEAQFET LTEWMDWSLA DRDVDLDGIY YCPHHPQGSV EEFRQLCDCR KPHPGMLLSA   120
RDYLHIDMAA SYMVGDKLED MQAAVAANVG TKVLVRTGKP ITPEAENAAD WVLNSLADLP   180
QAIKKQQKPA R                                                        191

SEQ ID NO: 102       moltype = AA  length = 188
FEATURE              Location/Qualifiers
source               1..188
                     mol_type = protein
                     organism = Escherichia albertii
SEQUENCE: 102
MAKSVPAIFL DRDGTINVDH GYVHEIDNFE FIDGVIDAMR ELKKMGFALV VVTNQSGIAR    60
GKFTEAQFET LTEWMDWSLA DRDVDLDGIY YCPHHPQGSV EEFRQVCDCR KPHPGMLISA   120
RDYLHIDMTA SYMVGDKLED MQAASAANVG TKVLVRTGKP VTPEAEDAAD WVLNSLADLP   180
QAIKKQQK                                                            188

SEQ ID NO: 103       moltype = AA  length = 188
FEATURE              Location/Qualifiers
source               1..188
                     mol_type = protein
                     organism = Kluyvera intermedia
SEQUENCE: 103
MAKSVPAIFL DRDGTINVDH GYVHEIDNFE FIEGVIDAMR ELKAMGFALV VVTNQSGIAR    60
GKFTEAQFET LTEWMDWSLA DRDVDLDGIY YCPHHPQGTV EEFRQVCDCR KPHPGMLISA   120
RDYLHIDMSA SYMVGDKLED MQAAAADVG TKVLVRTGKP VTPEAENAAD WVINSLADLP    180
AAIKKQQK                                                            188

SEQ ID NO: 104       moltype = AA  length = 188
FEATURE              Location/Qualifiers
source               1..188
                     mol_type = protein
                     organism = Citrobacter koseri
SEQUENCE: 104
MAKSVPAIFL DRDGTINVDH GYVHEIDEFE FIEGVIDAMR ELKKMGFALV VVTNQSGIAR    60
GKFTEAQFET LTEWMDWSLA DRDVDLDGIY YCPHHPQGSV EEFRQACDCR KPHPGMLISA   120
RDFLHIDMAA SYMVGDKIED MQAAAAANVG TKVLVRTGKP VTPEAENAAD WVLNSLADLP   180
SAIRKQQK                                                            188

SEQ ID NO: 105       moltype = AA  length = 188
FEATURE              Location/Qualifiers
source               1..188
                     mol_type = protein
                     organism = Kosakonia arachidis
SEQUENCE: 105
MTKSVPAIFL DRDGTINVDH GYVHEIDNFE FIDGVIDAMR ELKEMGYALV LVTNQSGIAR    60
GKFTEAQFET LTEWMDWSLA DRGVDLDGIY YCPHHPQGTV EEFRQVCDCR KPHPGMLISA   120
RDFLHIDMSA SYMVGDKIED MQAAQAAQVG TKVLVRTGKP ITPEAEKSAD WVINSLAELP   180
LAIKKHQK                                                            188

SEQ ID NO: 106       moltype = AA  length = 187
FEATURE              Location/Qualifiers
source               1..187
```

```
                              mol_type = protein
                              organism = Kluyvera cryocrescens
SEQUENCE: 106
MAKSVPAIFL DRDGTINVDH GYVHEIDDFE FIDGVIDAMR ELKEMGYALV LVTNQSGIAR    60
GKFTEAQFET LTEWMDWSLA DRGVDLDGIY FCPHHPQGTV EEYRQVCDCR KPHPGMLKSA   120
QEYLHIDMSS SYMVGDKIED MQAAAAANVG TKVLVRTGKP VTEDAEKAAD WVINSLADLP   180
AMIKKQK                                                             187

SEQ ID NO: 107                moltype = AA   length = 188
FEATURE                       Location/Qualifiers
source                        1..188
                              mol_type = protein
                              organism = Leclercia adecarboxylata
SEQUENCE: 107
MAKSVPAIFL DRDGTINVDH GYVHEIDEFE FIEGVIEAMR ELKEMGFALV VVTNQSGIAR    60
GKFTEAQFET LTEWMDWSLA DRGVDLDGIY YCPHHPQGTV EEYRQTCDCR KPHPGMFISA   120
QEFLHIDMSA SYMVGDKLED MQAAAAAGVG HKILVRTGKP VTPEAENAAD CVINSLAALP   180
ETIKKQQK                                                            188

SEQ ID NO: 108                moltype = AA   length = 219
FEATURE                       Location/Qualifiers
source                        1..219
                              mol_type = protein
                              organism = Shigella sonnei
SEQUENCE: 108
MKLQGVIFDL DGVITDTAHL HFQAWQQIAA EIGISIDAQF NESLKGISRD ESLRRILQHG    60
GKEGDFNSQE RAQLAYRKNL LYVHSLRELT VNAVLPGIRS LLADLRAQQI SVGLASVSLN   120
APTILAALEL RKFFTFCADA SQLKNSKPDP EIFLAACAGL GVPPQACIGI EDAQAGIDAI   180
NASGMRSVGI GAGLTGAQLL LPSTESLTWP RLSAFWQNV                          219

SEQ ID NO: 109                moltype = AA   length = 219
FEATURE                       Location/Qualifiers
source                        1..219
                              mol_type = protein
                              organism = Escherichia coli
SEQUENCE: 109
MKLQGVIFDL DGVITDTAHL HFKAWQQIAA EIGISIDAQF NESLKGISRD ESLRRILQHG    60
GKEGDFNPQE RAQLAYRKNL LYVHSLRELT VNAVLPGIRN LLADLRAQQI PVGLASVSLN   120
APTILAALEL REFFTFCADA SQLKNSKPDP EIFLAACAGL GVPPQACIGI EDAQAGIDAI   180
NASGMRSVGI GAGLTGAQLL LPSTDSLTWP RLSAFWQNV                          219

SEQ ID NO: 110                moltype = AA   length = 219
FEATURE                       Location/Qualifiers
source                        1..219
                              mol_type = protein
                              organism = Escherichia coli
SEQUENCE: 110
MKLQGVIFDL DGVITDTAHL HFQAWQQIAA EIGIGIDVQF NETLKGISRD ESLRRILQHG    60
GKEGDFNVQE RAQLAYRKNL LYVHSLRELT VNAVLPGIRP LLADLRAQGI PVGLASVSLN   120
APTILAALEL REFFTFCADA SQLKHSKPDP EIFLAACAGL GVPPQACIGI EDAQAGIDAI   180
NASGMRSVGI GTSLTGAQLL LPSTESLTWP RLSAFWQNV                          219

SEQ ID NO: 111                moltype = AA   length = 208
FEATURE                       Location/Qualifiers
source                        1..208
                              mol_type = protein
                              organism = Shigella flexneri
SEQUENCE: 111
MKLQGVIFDL DGVITDTAHL HFQAWQQIAA EIGISIDAQF NESLKGISRD ESLRRILQHG    60
GKEGDFNPQE RAQLAYRKNL LYVHSLRELT VNAVLPGIRN LLAELRAQQI PVGLASVSLN   120
APTILAALEL REFFTFCADA SQLKNSKPDP EIFLAACAGL GVPPQACIGI EDAQAGIDAI   180
NASGMRSVGI GAGLTGAQLL LPSTDSLT                                      208

SEQ ID NO: 112                moltype = AA   length = 216
FEATURE                       Location/Qualifiers
source                        1..216
                              mol_type = protein
                              organism = Shigella sonnei
SEQUENCE: 112
MRCKGFLFDL DGTLVDSLPA VERAWSNWSR RHGLAPEEVL AFIHGKQAIT SLRHFMAGKS    60
EADIAAEFTR LEHIEATETE GITALPGAIA LLSHLNKAGI PWAIVTSGSM PVARARHKIA   120
GLPAPEVFVT AERVKRGKPE PDAYLLGAQL LGLAPQECVV VEDAPAGVLS GLAAGCHVIA   180
VNAPADTPGL NEVDLVLHSL EQITVTKQPN GDVIIQ                             216

SEQ ID NO: 113                moltype = AA   length = 215
FEATURE                       Location/Qualifiers
source                        1..215
                              mol_type = protein
                              note = NBRC 105721
```

```
                              organism = Citrobacter werkmanii
SEQUENCE: 113
MQCKGFLFDL DGTLVDSLPA VERAWCNWAD RFGLDHAEVL GFIHGKQAIT SLRHFMVGKS    60
EAEIAAEFTR LEQIEATETA GITALPGAVD LLNHLNKAGI PWAIVTSGSM PVARARHRVA   120
GLPAPEVFVT AERVKRGKPE PDAYLLGAQL LGLAPQECAV VEDAPAGVLS GLAAGCHVIA   180
VNAPADTPRL DEVDFSLTSL EQISVTKQPN GNVVV                              215

SEQ ID NO: 114            moltype = AA  length = 215
FEATURE                   Location/Qualifiers
source                    1..215
                          mol_type = protein
                          organism = Citrobacter freundii
SEQUENCE: 114
MQCKGFLFDL DGTLVDSLPA VERAWCNWAD RFGLDHAEVL GFIHGKQAIT SLRHFMVGKS    60
EAEIAAEFTR LEQIEATETA GITALPGAVD LLNHLNKAGI PWAIVTSGSM PVARARHRVA   120
GLPAPEVFVT AERVKRGKPE PDAYLLGAQL LGVAPQECAV VEDAPAGVLS GLAAGCHVIA   180
VNAPADTPRL DEVDFSLTSL EHISVTKQPN GNVVV                              215

SEQ ID NO: 115            moltype = AA  length = 215
FEATURE                   Location/Qualifiers
source                    1..215
                          mol_type = protein
                          organism = Citrobacter amalonaticus
SEQUENCE: 115
MQCKGFLFDL DGTLVDSLPA VERAWCNWAD RFGLAHDDVL SFVHGKQAIT SLRHFMAGKP    60
EAEIVAEFTR LEKIEATETA GITALPGAVA LLNHLNKAGI PWAIVTSGSM PVARARHQVA   120
NLPAPEVFVT AERVKRGKPE PDAYLLGAQL LGLSPHECVV VEDAPAGVLS GLAAGCHVIA   180
VNAPADTPRL DEVDFVLTSL EQLSVTKQPN GDVVV                              215

SEQ ID NO: 116            moltype = AA  length = 215
FEATURE                   Location/Qualifiers
source                    1..215
                          mol_type = protein
                          organism = Salmonella enterica
SEQUENCE: 116
VQCKGFLFDL DGTLVDSLPA VERAWCSWAD RFNLAHDEVL GFIHGKQAIT SLRHFMAGKS    60
EAEIAAEFTR LEQIEATETA GITALPGAVD LLNHLNKAGI PWAIVTSGSM PVARARHQVA   120
GLPAPEVFVT AERVKRGKPE PDAYLLGAQL LGLVPQECVV VEDAPAGVLS GLAAGCHVIA   180
VNAPADTPRL ADVDFALNSL TQLSVAKQPN GDVVV                              215

SEQ ID NO: 117            moltype = AA  length = 216
FEATURE                   Location/Qualifiers
source                    1..216
                          mol_type = protein
                          organism = Escherichia fergusonii
SEQUENCE: 117
MRCKGFLFDL DGTLVDSLPA VERAWCNWAD RFGIDHHELL SFIHGKQAIT SLRHFMPGRP    60
EEEILAEFTR LEQIEATQTE GITALPGAIE LLTHLNKSGI PWAIVTSGSM PVARARHQVA   120
GLPFPEVFVT AERVKRGKPE PDAYLLGAQL LGLEPKECVV VEDAPAGVLS GLAAGCHVIA   180
VNTPADTPRL SEVDFVLTSL QQITVTKQPN GEVIIQ                             216

SEQ ID NO: 118            moltype = AA  length = 215
FEATURE                   Location/Qualifiers
source                    1..215
                          mol_type = protein
                          note = subsp. enterica serovar Hadar
                          organism = Salmonella enterica
SEQUENCE: 118
VQCKGFLFDL DGTLVDSLPA VERAWCSWAD RFNLAHDEVL GFIHGKQAIT SLRHFMAGKS    60
EAEIAAEFTR LEQIEATETA GITALPGAVD LLNHLNKAGI PWAIVTSGSM PVARARHQVA   120
GLPAPEVFVT AERVKRGKPE PDAYLLGAQL LGLSPQECVV VEDAPAGVLS GLAAGCHVIA   180
VNAPADTPRL ADVDFALDSL TQLSVAKQPN GDVVV                              215

SEQ ID NO: 119            moltype = AA  length = 270
FEATURE                   Location/Qualifiers
source                    1..270
                          mol_type = protein
                          organism = Escherichia coli
SEQUENCE: 119
MAIKLIAIDM DGTLLLPDHT ISPAVKNAIA AARARGVNVV LTTGRPYAGV HNYLKELHME    60
QPGDYCITYN GALVQKAADG STVAQTALSY DDYRFLEKLS REVGSHFHAL DRTTLYTANR   120
DISYYTVHES FVATIPLVFC EAEKMDPNTQ FLKVMMIDEP AILDQAIARI PQEVKEKYTV   180
LKSAPYFLEI LDKRVNKGTG VKSLADVLGI KPEEIMAIGD QENDIAMIEY AGIGVAMDNA   240
IPSVKEVANF VTKSNLEDGV AFAIEKYVLN                                    270

SEQ ID NO: 120            moltype = AA  length = 270
FEATURE                   Location/Qualifiers
source                    1..270
                          mol_type = protein
```

```
                        organism = Escherichia fergusonii
SEQUENCE: 120
MAIKLIAIDM DGTLLLPDHT ISPAVKNAIA AARARGVNVV LTTGRPYAGV HNYLKELHME   60
QPGDYCITYN GALVQKAADG STVAQTALSY EDYRFLEKLS REVGSHFHAL DRTTLYTANR   120
DISYYTVHES FVATIPLVFC EAEKMDPNTQ FLKVMMIDEP TILDQAIARI PQEVKEKYTV   180
LKSAPYFLEI LDKRVNKGTG VKSLADVLGI KPEEIMAIGD QENDIAMIEY AGVGVAMDNA   240
IPSVKEVANF VTKSNLEDGV AFAIEKYVLN                                   270

SEQ ID NO: 121          moltype = AA  length = 270
FEATURE                 Location/Qualifiers
source                  1..270
                        mol_type = protein
                        organism = Shigella sonnei
SEQUENCE: 121
MAIKLIAIDM DGTLLLPDHT ISPAVKNAIA AARARGVNVV LTTGRPYAGV HNYLKELHME   60
LPGDYCITYN GALVQKAADG STVAQTALSY DDYRFLEKLS REVGSHFHAL DRTTLYTANR   120
DISYYTVHES FVATIPLVFC EAEKMDPNTQ FLKVMMIDEP AILDQAIARI PQEVKEKYTV   180
LKSAPYFLEI LDKRVNKSTG VKSLADVLGI KPEEIMAIGD QENDIAMIEY AGVGVAMDNA   240
IPSVKEVANF VTKSNLEDGV AFAIEKYVLN                                   270

SEQ ID NO: 122          moltype = AA  length = 269
FEATURE                 Location/Qualifiers
source                  1..269
                        mol_type = protein
                        organism = Trabulsiella guamensis
SEQUENCE: 122
MAIKLIAIDM DGTLLLPDHT ISPAVKNAIA AARMRGVNVV LTTGRPYAGV HHYLKELHME   60
QPGDYCITYN GALVQKASDG STVAQTALSY DDYRFLEKLS REVGSHFHAL DRNTLYTANR   120
DISYYTVHES YVATIPLVFC EAEKMDPATQ FLKVMMIDEP VVLDKAIARI PAEVKEKYTV   180
LKSAPYFLEI LDKRVNKGTG VKSLADVLGI QPDEIMAIGD QENDIAMIEY AGVGVAMDNA   240
IPSVKEVANF ITKSNLEDGV AYAIEKYVL                                    269

SEQ ID NO: 123          moltype = AA  length = 270
FEATURE                 Location/Qualifiers
source                  1..270
                        mol_type = protein
                        organism = Citrobacter amalonaticus
SEQUENCE: 123
MAIKLIAIDM DGTLLLPDHT ISPAVKRAIA AAREKGVNVV LTTGRPYAGV HSYLKELHME   60
QPGDYCITYN GALVQKAGDG STVAQTALSY DDYRYLEKLS REVGSHFHAL DRTTLYTANR   120
DISYYTVHES YVATIPLVFC EAEKMDPKTQ FLKVMMIDEP AILDQAIARI PAEVKEKYTV   180
LKSAPYFLEI LDKRVNKGTG VKSLADALGI KPEEIMAIGD QENDIAMIEY AGLGVAMDNA   240
IPSVKEIANF VTKSNLEDGV AYAIEQHVLK                                   270

SEQ ID NO: 124          moltype = AA  length = 269
FEATURE                 Location/Qualifiers
source                  1..269
                        mol_type = protein
                        organism = Klebsiella pneumoniae
SEQUENCE: 124
MAIKLIAIDM DGTLLLPDHT ISPAVKTAIA AARERGVNVV LTTGRPYAGV HSYLKELHME   60
QPGDYCITYN GALVQKAGDG STVAQTALSY DDYRFLEQLS REVGSHFHAL DRNTLYTANR   120
DISYYTVHES YVATIPLVFC EAEKMDPEIQ LLKVMMIDEP AILDQAIARI PAEVKEKYTV   180
LKSAPYFLEI LDKRVNKGTG VKSLADALGI KPEEIMAIGD QENDIAMIEF AGVGVAMDNA   240
IPAVKEAANF ITKSNLEDGV AFAIEKYVL                                    269

SEQ ID NO: 125          moltype = AA  length = 269
FEATURE                 Location/Qualifiers
source                  1..269
                        mol_type = protein
                        organism = Trabulsiella odontotermitis
SEQUENCE: 125
MAIKLIAIDM DGTLLLPDHT ISPAVKNAIA AARMRGVNVV LTTGRPYAGV HHYLKELHME   60
QPGDYCITYN GALVQKASDG STVAQTALSY DDYRYLEKLS REVGSHFHAL DRNTLYTANR   120
DISYYTVHES YVATIPLVFC EAEKMDPATQ FLKVMMIDEP VVLDKAIARI PAEVKEKYTV   180
LKSAPYFLEI LDKRVNKGTG VKSLAEALGI QPDEIMAIGD QENDIAMIEY AGVGVAMDNA   240
IPSVKEVANF ITKSNLEDGV AYAIEKYVL                                    269

SEQ ID NO: 126          moltype = AA  length = 270
FEATURE                 Location/Qualifiers
source                  1..270
                        mol_type = protein
                        organism = Enterobacter kobei
SEQUENCE: 126
MAIKLIAIDM DGTLLLPDHT ISPAVKKAIA AAREKGVNVV LTTGRPYAGV HNYLRELHMD   60
KPGDYCITYN GALVQKASDG STVAQTTLSY DDYRYLEQLS REVGSHFHAL DRNTLYTANR   120
DISYYTVHES YVATIPLVFC EAEKMDPAIQ LLKVMMIDEP AILDKAIARI PAEVKEKYTV   180
LKSAPYFLEI LDKRVNKGTG VKSLADTLGI TPDEIMTLGD QENDIAMIEY AGLGVAMDNA   240
IDSVKEVADF VTKSNLEDGV AYAIEKFVLN                                   270
```

```
SEQ ID NO: 127          moltype = AA   length = 238
FEATURE                 Location/Qualifiers
source                  1..238
                        mol_type = protein
                        organism = Shigella sonnei
SEQUENCE: 127
MRFYRPLGRI SALTFDLDDT LYDNRPVILR TEREALTFVQ NYHPALRSFQ NEDLQRLRQA    60
VREAEPEIYH DVTRWRFRSI EQAMLDAGLS AEEASAGAHA AMINFAKWRS RIDVPQQTHD   120
TLKQLAKKWP LVAITNGNAQ PELFGLGDYF EFVLRAGPHG RSKPFSDMYF LAAEKLNVPI   180
GEILHVGDDL TTDVGGAIRS GMQACWIKPE NGDLMQTWDS RLLPHLEISR LASLTSLI     238

SEQ ID NO: 128          moltype = AA   length = 223
FEATURE                 Location/Qualifiers
source                  1..223
                        mol_type = protein
                        organism = Shigella sonnei
SEQUENCE: 128
MRFYRPLGRI SALTFDLDDT LYDNRPVILR TEREALTFVQ NYHPALRSFQ NEDLQRLRQA    60
VREAEPEIYH DVTRWRFRSI EQAMLDAGLS AEEASAGAHA AMINFAKWRS RIDVPQQTHD   120
TLKQLAKKWP LVAITNGNAQ PELFGLGDYF EFVLRAGPHG RSKPFSDMYF LAAEKLNVPI   180
GEILHVGDDL TTDVGGAIRS GMQACWIRPE NGDLMQTWDS RLL                     223

SEQ ID NO: 129          moltype = AA   length = 238
FEATURE                 Location/Qualifiers
source                  1..238
                        mol_type = protein
                        organism = Salmonella enterica
SEQUENCE: 129
MRFYRPLGRI AALTFDLDDT LYDNRPVILR TEQEALAFMQ NYHPSLRSFQ NVDLQRIRQA    60
VREAEPEIYH DVTRWRHRAI EQAMRDAGLS AQEAIAGANA AMMHFAKWRS QIEVPQATHE   120
TLQQLAKKWP LVAITNGNAQ PELFGLGDYF KFVLRAGPDG RSKPFSDMYF LVAEKLHVPI   180
GEILHVGDDL TTDVAGAIRC GMQACWIKPE NADLMRTQDS RLLPHIEISR LASLTSLI     238

SEQ ID NO: 130          moltype = AA   length = 238
FEATURE                 Location/Qualifiers
source                  1..238
                        mol_type = protein
                        organism = Citrobacter braakii
SEQUENCE: 130
MRFYRPLGRI SALTFDLDDT LYDNRPVITR TEQEALAFVQ NYHPALNSLQ NSDLQRLRQA    60
VRDAEPEIYH DVTQWRHRAV ERAMLEAGLS EAEAKMGANA AMMNFAKWRS RIDVPQSTHD   120
TLKTLARKWP LVAITNGNAQ PELFGLGDYF EFVLRAGPDG RSKPFSDMYA LAAEKLKMPV   180
GEILHVGDDL TTDVAGAIRC GMQACWIKPE NADLMQTADS RLLPHIEISQ LASLTSLI     238

SEQ ID NO: 131          moltype = AA   length = 238
FEATURE                 Location/Qualifiers
source                  1..238
                        mol_type = protein
                        organism = Enterobacter hormaechei
SEQUENCE: 131
MRFYRPLGQI SALTFDLDDT LYDNRPVILR TEQESLAFVQ NYHPALKTMQ NKDFQKLRQS    60
LRETEPDIYH DVTEWRRRAV EQAMLNVGLS SQDAAIGAEA AMENFAKWRS RVDVPQETHD   120
TLAKLAEKWP LVAITNGNAQ PELFGLGDYF EFVLRAGPHG RSKPFSDMYH LAAEKLNLPL   180
GEILHVGDDL TTDVAGAIRC GMQACWIKPE NASLMTTPDS RLLPHLEISR LASLTTLI     238

SEQ ID NO: 132          moltype = AA   length = 238
FEATURE                 Location/Qualifiers
source                  1..238
                        mol_type = protein
                        organism = Lelliottia amnigena
SEQUENCE: 132
MRFYRPLGQI SALTFDLDDT LYDNRQVILR TEQEALAFVQ NYHPSLKTLQ NTDFQRLRQA    60
LRETEPDIYH DVTEWRRRAV EQAMINAGLT AAEAALGAEA SMANFAKWRS RIDVPQETHD   120
TLAKLAEKWP LVAITNGNAQ PELFGLGDYF TFVFRAGPHG RSKPFSDMYH LAAEKLDLPL   180
GEILHVGGDL TTDVAGAIRC GMQACWIKPE NADLMHTIDS RLLPHVEISR LASLTTLI     238

SEQ ID NO: 133          moltype = AA   length = 238
FEATURE                 Location/Qualifiers
source                  1..238
                        mol_type = protein
                        organism = Leclercia adecarboxylata
SEQUENCE: 133
MRFYRPLGQI SALTFDLDDT LYDNRQVILR TEQEALTFVQ NYHPALKTLE NKEFHRLRQA    60
LRQTEPEIYH DVTEWRRRAV ELAMLNAGLT AAEAALGAEA SMAHFAQWRS RIDVPQETHD   120
TLAALAEKWP LVAITNGNAQ PELFGLGDYF QFVLRAGPHG RSKPFNDMYH LAAEKLSLPL   180
GQILHVGDDL TTDVAGAIRC GMQACWIKPE NADLMQTADS RLLPHIEISR LASLTTLI     238

SEQ ID NO: 134          moltype = AA   length = 190
```

```
FEATURE                 Location/Qualifiers
source                  1..190
                        mol_type = protein
                        organism = Shigella flexneri
SEQUENCE: 134
MSTPRQILAA IFDMDGLLID SEPLWDRAEL DVMASLGVDI SRRNELPDTL GLRIDMVVDL   60
WYARQPWNGP SRQEVVERVI ARAISLVEET RPLLPGVREA VALCKEQGLL VGLASASPLH  120
MLEKVLTMFD LRDSFDALAS AEKLPYSKPH PQVYLDCAAK LGVDPLTCVA LEDSVNGMIA  180
SKAARMRSIV                                                         190

SEQ ID NO: 135          moltype = AA  length = 222
FEATURE                 Location/Qualifiers
source                  1..222
                        mol_type = protein
                        organism = Kosakonia sacchari
SEQUENCE: 135
MTTPRQILAA IFDMDGLLID SEPLWDRAEL EVVASLGVDI TRRHELPDTL GLRIDMVVEL   60
WYAQQPWNGP DRQEVTECII QRAISLVEEK RPLLPGVREA IALCKANGLL VGLASASPLH  120
MLEKVLAMFE LRDSFDALAS AEKLPYSKPH PQVYLDCAAK LGVDPLTCVA LEDSVNGMIA  180
SKAARMRSIV VPDEEHRADP RYVLANVKLT SLEQLTLAHP IG                     222

SEQ ID NO: 136          moltype = AA  length = 222
FEATURE                 Location/Qualifiers
source                  1..222
                        mol_type = protein
                        organism = Enterobacter mori
SEQUENCE: 136
MSTPRQILAA IFDMDGLLID SEPLWDRAEL DVMASLGVDI SRRNELPDTL GLRIDMVVDL   60
WYAHQPWVGP GRDEVIARII NRAITLVEEQ KPLLPGVRDA IALCKAQGLK VGLASASPLH  120
MLEKVLSLFE LRDSFDALAS AEKLPYSKPH PQVYMDCAAK LGLDPLTCVA LEDSVNGMVA  180
SKAARMRSIV VPAEEGRHDP RFALADVKLA SLEDLTVAHL RG                     222

SEQ ID NO: 137          moltype = AA  length = 222
FEATURE                 Location/Qualifiers
source                  1..222
                        mol_type = protein
                        organism = Lelliottia amnigena
SEQUENCE: 137
MSTSRQIVAA IFDMDGLLID SEPLWDRAEL DVMESLGVDI RRRNELPDTL GLRIDMVVEL   60
WYAHQPWNGP SRQEVTDRII SRALTLVEAS RPLLPGVREA VALCKAQGLK VGLASASPLH  120
MLEKVLAMFD LRESFDALAS AEKLPYSKPH PQVYMDCAAK LGVDTLACVA LEDSVNGMIA  180
SKAARMRSVV VPAEEGQHDP RFALADVKLA TLADLTPAHL RG                     222

SEQ ID NO: 138          moltype = AA  length = 222
FEATURE                 Location/Qualifiers
source                  1..222
                        mol_type = protein
                        note = 638
                        organism = Enterobacter sp.
SEQUENCE: 138
MSTPHQIVAA IFDMDGLLID SEPLWDRAEL DVMASLGVDI SRRGELPDTL GLRIDMVVEL   60
WFAHQPWSGP SREEVTARVI SRAIALVEEK RPLLPGAREA IALCKAQGLK VGLASASPLH  120
MLEKVLEMFD LRDSFDALAS AEKLPYSKPH PQVYMDCAAK LGVDPLACVA LEDSVNGMVA  180
SKAARMRSIV VPAEEGQHDP RFALANAKLT SLVDLTPAHL FG                     222

SEQ ID NO: 139          moltype = AA  length = 222
FEATURE                 Location/Qualifiers
source                  1..222
                        mol_type = protein
                        organism = Kosakonia radicincitans
SEQUENCE: 139
MTAPRQILAA IFDMDGLLID SEPLWDRAEL EVVASLGVDI NRRHELPDTL GLRIDMVVEL   60
WYAQQPWNGP DRKEVTERII QRAISLVEEK RPLLPGVREA IALCKANGLL VGLASASPLH  120
MLEKVLAMFE LRDSFDALAS AENLPYSKPH PQVYLDCAAK LGIDPLTCVA LEDSVNGMIA  180
SKAARMRSIV VPDEEHRTDP RYVLANVKLT SLEQLTLAHL IG                     222

SEQ ID NO: 140          moltype = AA  length = 209
FEATURE                 Location/Qualifiers
source                  1..209
                        mol_type = protein
                        note = subsp. enterica serovar Newport str.
                        organism = Salmonella enterica
SEQUENCE: 140
MDGLLIDSEP LWDRAELDVM ASLGVDITRR HELPDTLGLR IDMVVDLWFA QQPWNGPDRQ   60
EVTNRVIARA ITLIEETRPL LPGVREAVAL CKAQGLLVGL ASASPLHMLE KVLTMFELRD  120
SFDALASAEK LPYSKPHPQV YLDCAAKLGV DPLTCVALED SVNGLIAAKA ARMRAIVVPA  180
EENQHDPRFA LANVKLNSLT ELTAAHLLG                                    209

SEQ ID NO: 141          moltype = AA  length = 188
```

```
FEATURE              Location/Qualifiers
source               1..188
                     mol_type = protein
                     organism = Shigella flexneri
SEQUENCE: 141
MYERYAGLIF DMDGTILDTE PTHRKAWREV LGHYGLQYDV QAMIALNGSP TWRIAQAIIE    60
LNQADLDPHA LAREKTEAVR SMLLDSVEPL PLVEVVKSWH GRRPMAVGTG SESAIAEALL   120
AHLGLRRYFD AVVAADHVKH HKPAPDTFLL CAQRMGVQPT QCVVFEDADF GIQAARAAGM   180
DAVDIRLL                                                            188

SEQ ID NO: 142       moltype = AA  length = 188
FEATURE              Location/Qualifiers
source               1..188
                     mol_type = protein
                     organism = Escherichia albertii
SEQUENCE: 142
MYERYAGLIF DMDGTILDTE PTHRKAWREV LGRYGLRYNV QAMIALNGSP TWRIAQAIIE    60
LNQADLDPYA LAREKTEAVR SMLLDSVEPL PLVEVVKSWY GRRPMAVGTG SESAIAEALL   120
THLGLRRYFD TVVAADHVKH HKPAPDTFLL CAQHMGVQPA QCVVFEDADF GIQAARAAGM   180
DAVDVRLL                                                            188

SEQ ID NO: 143       moltype = AA  length = 188
FEATURE              Location/Qualifiers
source               1..188
                     mol_type = protein
                     organism = Salmonella enterica
SEQUENCE: 143
MYARYAGLIF DMDGTLLDTE PTHRKAWREV LGHYGLRFDE QAMVALNGSP TWLIAQSIIE    60
LNHADLDPLS LAREKTDAVK SILLDCVEPL PLVEVVKAWH GRRPMSVGTG SESAIAEALL   120
AHLGLRRYFD AVVAADHVQH HKPAPDTFLL CAQRMGVMPT QCVVFEDADF GLQAARAAGM   180
DAVDVRLL                                                            188

SEQ ID NO: 144       moltype = AA  length = 188
FEATURE              Location/Qualifiers
source               1..188
                     mol_type = protein
                     organism = Kluyvera intermedia
SEQUENCE: 144
MYERYDGLIF DMDGTILDTE PTHRKAWHDV LGHYGLRYDI QAMIALNGSP TWRIAQSVIE    60
LNQADLDPYA LAREKTEAVK AMLLDTVRPL PLIDVVKAWY GRRPLSVGTG SESAIAEALL   120
SHLGLRHYFA AVVAAEHVKN HKPAPDTFLL CAEKMGVAPQ KCVVFEDADF GLQAARSAGM   180
DAVDVRLL                                                            188

SEQ ID NO: 145       moltype = AA  length = 188
FEATURE              Location/Qualifiers
source               1..188
                     mol_type = protein
                     organism = Trabulsiella odontotermitis
SEQUENCE: 145
MYERYAGLIF DMDGTILDTE PTHRKAWHEV LGRYGIRFDE QSIIALNGSP TWRIAQEIIT    60
LNQADLDPHA LAREKTDAVK IMLLDSVQPL PLIDVVKAWH GRRPMSVGTG SESAIAEALL   120
AHLGLRHYFS AVVAADHVRH HKPAPDTFLL CAERMGVEPA KCIVFEDADF GLQAAASAGM   180
DVVDVRLL                                                            188

SEQ ID NO: 146       moltype = AA  length = 188
FEATURE              Location/Qualifiers
source               1..188
                     mol_type = protein
                     organism = Yokenella regensburgei
SEQUENCE: 146
MYERYAGLIF DMDGTILDTE PTHCKAWHDV LGRYGMHFDE QAMTALNGSP TWRIAQSIIE    60
LNQATLDPHQ LAREKTDAVK AMLLDTVRPL PLIDVVKAWH GRRPMAVGTG SESAIAEALL   120
AHLGLREYFT AVVAADHVKH HKPAPDTFLL CAELMGVAAN QCVVFEDADF GLQAARSAGM   180
DVVDVRLL                                                            188

SEQ ID NO: 147       moltype = AA  length = 188
FEATURE              Location/Qualifiers
source               1..188
                     mol_type = protein
                     organism = Raoultella terrigena
SEQUENCE: 147
MYERYAGLIF DMDGTILDTE PTHRKAWHEV LGRYGMRFDE QAMVALNGSP TWRIAQVIIE    60
LNQADLDPHR LALEKTNAVK AMLLDSVRPL PLIEVVKEWH GRRPMSVGTG SESAVAEALL   120
AHLGLRHYFS AVIAADHVTN HKPAPDTFLL CAERMGVAPE KCVVFEDADF GLQAARRAGM   180
DAVDVRLL                                                            188

SEQ ID NO: 148       moltype = AA  length = 188
FEATURE              Location/Qualifiers
source               1..188
```

```
                        mol_type = protein
                        organism = Klebsiella pneumoniae
SEQUENCE: 148
MYEGYAGLIF DMDGTILDTE PTHRQAWNEV LGRYGMRFDE QAMVALNGSP TWRIAQAIIE    60
LNQADLDPHR LAQEKTQAVK AMLLDSVRPL PLIEVVKAWH GCRPMSVGTG SESAVAEALL   120
AHLGLRHYFS AVVAADHVVN HKPAPDTFLL CAERMGVAPE KCVVFEDADF GLQAAKRAGM   180
DAVDVRLL                                                           188

SEQ ID NO: 149          moltype = AA  length = 223
FEATURE                 Location/Qualifiers
source                  1..223
                        mol_type = protein
                        organism = Pseudomonas putida
SEQUENCE: 149
MRLRAVLFDM DGTLLDTAPD FIAICQAMLA DRGLPAIDDA RIREVISGGA RAMVAATFAM    60
NPEADGFEAL RLEFLERYQR DCAVHSKLFD GMPELLADIE KGNLLWGVVT NKPVRFAEPI   120
MQRLGLAERS ALLICPDHVK NSKPDPEPLI LACKTLGLDP ASVLFVGDDL RDIESGRDAG   180
TRTAAVRYGY IHPEDNPNNW GADVVVDHPL ELRKVIDSAL CGC                    223

SEQ ID NO: 150          moltype = AA  length = 223
FEATURE                 Location/Qualifiers
source                  1..223
                        mol_type = protein
                        note = GM84
                        organism = Pseudomonas sp.
SEQUENCE: 150
MRLRAVLFDM DGTLLDTAPD FIAICQAMLA ERGLPAIDDK LIRDVISGGA RAMVAATFAM    60
NPDDDGFEPL RLEFLERYQR DCAVHSKLFD GMGELLADIE KGNLLWGVVT NKPVRFAEPI   120
MQRLGLAERS ALLICPDHVK NSKPDPEPLI LACKTLNLDP ASVLFVGDDL RDIESGRDAG   180
TRTAAVRYGY IHPEDNPNNW GADVVVDHPL ELRKVIDSAL CGC                    223

SEQ ID NO: 151          moltype = AA  length = 223
FEATURE                 Location/Qualifiers
source                  1..223
                        mol_type = protein
                        organism = Pseudomonas entomophila
SEQUENCE: 151
MRLRAVLFDM DGTLLDTAPD FIAICQAMLT DRGLPTIDDA RIRDVISGGA RAMVAATFAM    60
DPDAEGFEAL RLEFLERYQR DCAVHSKLFD GMPELLADIE KGNLLWGVVT NKPVRFAEPI   120
MQRLGLAERS ALLICPDHVK NSKPDPEPLI LACKTLDLDP ASVLFVGDDL RDIESGRDAG   180
TRTAAVRYGY IHPEDNPNNW GADVVVDHPL ELRKVIDSAL CGC                    223

SEQ ID NO: 152          moltype = AA  length = 223
FEATURE                 Location/Qualifiers
source                  1..223
                        mol_type = protein
                        organism = Pseudomonas vranovensis
SEQUENCE: 152
MRLRAVLFDM DGTLLDTAPD FIAICQAMLA DRGLPAIDDQ RIRDVISGGA RAMVEVTFGI    60
TPEVAEFEAL RLEFLERYQR DCAVHSKLFD GMAELLADIE KGNLLWGVVT NKPVRFAEPI   120
MQRLGLAERS ALLICPDHVK NSKPDPEPLI LACKTLNLDP ASVLFVGDDL RDIESGRDAG   180
TRTAAVRYGY IHPEDNPNNW GADVVVDHPL ELRKVLDSAL CGC                    223

SEQ ID NO: 153          moltype = AA  length = 223
FEATURE                 Location/Qualifiers
source                  1..223
                        mol_type = protein
                        organism = Pseudomonas cannabina
SEQUENCE: 153
MRLRAVLFDM DGTLLDTAPD FIAIAQAMLA DRGLPAVADK LIRDEISGGA KAMVAAAFAL    60
SPEAPEFEAL RLEFLERYQR DCATHSRLFN GMPELLADIE KAGLIWGVVT NKPVRFAQPI   120
MEQLKLAERS AVLICPDHVT HSKPHPEPMI LACKLLDLDP ASVLFVGDDL RDIESGRDAG   180
TKTAAVRYGY IHPDDNPDHW GADVVVDHPL ELRKVLDNAL CSC                    223

SEQ ID NO: 154          moltype = AA  length = 223
FEATURE                 Location/Qualifiers
source                  1..223
                        mol_type = protein
                        organism = Pseudomonas monteilii
SEQUENCE: 154
MRLRAVLFDM DGTLLDTAPD FIAICQAMLA ERGLPAIDDQ AIRDVISGGA RAMVAATFAM    60
NPEDEGFEAL RLEFLERYQR DCAVHSKLFD GMGELLADLE KGKLLWGVVT NKPVRFAEPI   120
MQQLGLAERS ALLICPDHVK NSKPDPEPLI LACKTLNLDP ASVLFVGDDL RDIESGRDAG   180
TRTAAVRYGY IHPDDNPNHW GADVVVDHPL ELRKVIDSAL CGC                    223
```

IN VIVO SYNTHESIS OF SIALYLATED COMPOUNDS

CROSS REFERENCE TO RELATED APPLICATIONS

This application is a continuation of U.S. Ser. No. 16/473,932, filed Jun. 26, 2019, now U.S. Pat. No. 11,535,878, which is a 371 of PCT/EP2017/084593 Dec. 26, 2017, which claims the benefit of European Patent Office (EPO) application 16206916.5 filed Dec. 27, 2016.

STATEMENT REGARDING ELECTRONIC FILING OF A SEQUENCE LISTING

Pursuant to 37 C.F.R. § 1.821, a Sequence Listing ASCII text file entitled "004-PCT Sequence Listing_ST26.txt (updated)," 176 KB in size, generated Aug. 23, 2023, has been submitted via EFS-Web is provided in lieu of a paper copy. This Sequence Listing is hereby incorporated by reference into the specification for its disclosures.

TECHNICAL FIELD

This disclosure is in the technical field of synthetic biology and metabolic engineering. More particularly, this disclosure is in the technical field of fermentation of metabolically engineered microorganisms. This disclosure describes engineered micro-organisms able to synthesize sialylated compounds via an intracellular biosynthesis route. These micro-organisms can dephosphorylate N-acetylglucosamine-6-phosphate to N-acetyl glucosamine and convert the N-acetylglucosamine to N-acetylmannosamine. These micro-organisms also have the ability to convert N-acetylmannosamine to N-acetyl-neuraminate. Furthermore, this disclosure provides a method for the large scale in vivo synthesis of sialylated compounds, by culturing a microorganism in a culture medium, optionally comprising an exogenous precursor such as, but not limited to lactose, lacto-N-biose, N-acetyllactosamine and/or an aglycon, wherein the microorganism intracellularly dephosphorylates N-acetylglucosamine-6-phosphate to N-acetyl-glucosamine, converts N-acetylglucosamine to N-acetylmannosamine and convert the latter further to N-acetyl-neuraminate.

BACKGROUND

Sialylated compounds such as sialic acid and sialylated oligosaccharides have gained attention the last years, because of their broad application range. For example, sialic acid is considered as an anti-viral precursor. Sialylated oligosaccharides form an essential part of human milk and are ascribed anti-adhesive and immunomodulatory properties; others described them to be involved in brain development. Sialylation, in general, of proteins, lipids or aglycons are used in anti-cancer medicine and in the treatment of neurological diseases.

Sialic acid is a general term used to describe a large family of acidic sugars that are predominantly found on the cell surface of eukaryotic cells. The most common sialic acid is N-acetylneuraminic acid or Neu5Ac, an acidic nine-carbon sugar that undergoes several modifications to generate the members of the sialic acid family. As seen in e.g., FIG. 1 of WO2008097366, the diversity of the sialic acid family is represented with over 50 known members. Sialic acid represents a large family of cell-surface carbohydrates that are derived from an acidic, nine-carbon parent compound called N-acetylneuraminic acid or Neu5Ac. Neu5Ac is often decorated with acetyl, phosphate, methyl, sulfate and lactyl groups, which are described to be required for desirable cell signaling and cell adhesion events mediated by sialic acid.

Sialic acids and sialylated compounds are common in higher eukaryotic organisms that produce them in a conserved biosynthetic route. This route starts from endogenic UDP-N-acetylglucosamine that is converted to sialic acid through the action of a UDP-N-acetyl-glucosamine 2-epimerase (hydrolyzing) (EC 3.2.1.183), a N-acylmannosamine kinase (EC 2.7.1.60), a N-acylneuraminate-9-phosphate synthase (EC 2.5.1.57) and a Neu5Ac-9-P phosphatase (EC 3.1.3.29). This sialic acid can subsequently be activated and transferred to the desired acceptor via a CMP-sialic acid synthase (EC 2.7.7.43) and e.g., a sialyltransferase.

Efforts have been made to express this biosynthetic route in other eukaryotic organisms, whereas prokaryotic systems were not reported. The pathway was functionally expressed in yeast (*Pichia pastoris*) and plant (*Arabidopsis thaliana*) to produce sialylated N-glycans. However, large scale production of sialylated oligosaccharides was never reported. The functional overexpression of eukaryotic genes in prokaryotic systems remains a daunting task without certain outcome due to the lack of specific chaperones, faulty enzyme folding and missing cell organelles. On top of that remains the huge energy requirement of the pathway and the depletion of intercellulair UDP-GlcNAc (UDP-N-acetylglucosamine), necessary for cell growth.

Processes based on enzymatic, chemical as well as fermentative production of sialylated compounds exist. However, all of them have significant disadvantages. For instance, chemical synthesis requires many sequential chemical steps and enzymatic synthesis requires expensive precursors, whereas the fermentative process is still under heavy development. Nonetheless, the latter has the highest industrial production potential.

One type of described fermentative production process uses a biosynthesis route that originates from prokaryotes like *Campylobacter jejuni* that naturally produces sialic acid or sialylated compounds. This biosynthesis route starts from endogenous UDP-N-acetyl-glucosamine that cells use for their cell wall. This is converted to N-acetyl-mannosamine and N-acetylneuraminate by the action of an UDP-N-acetyl-glucosamine epimerase (generally named neuC) and a sialic acid synthase (generally named neuB).

Using only part of this prokaryotic biosynthesis route, Priem et al. (*Glycobiology* 12, 2002, 235-240) describe the use of living bacterial cells to produce sialyloligosaccharides. In this method, sialyllactose was directly produced by growing cells of metabolically engineered *Escherichia coli* strains that overexpressed the *Neisseria meningitidis* genes for alpha-2,3-sialyltransferase and for CMP-Neu5Ac synthase, these strains were further devoid of beta-galactosidase and N-acetylneuraminic acid (Neu5Ac) aldolase activities. These microorganisms were grown at high cell density with glycerol as the carbon and energy source, while exogenous lactose and Neu5Ac were supplied as precursors for sialyllactose synthesis. During the growth, lactose and Neu5Ac were internalized by the induction of the expression of an *E. coli* galactoside and an exogenous Neu5Ac permease. Lactose and Neu5Ac accumulate in the cytoplasm where Neu5Ac was then converted into CMP-Neu5Ac to be further transferred on lactose to form sialyllactose. Large scale production of sialyloligosaccharides by this microbiological method requires important amounts of Neu5Ac as a precursor.

Another microbial system was developed for production of sialyloligosaccharides without the need of an exogenous supply of sialic acid. WO2007101862 describes such method for producing sialylated oligosaccharides with micro-organisms comprising heterologous genes encoding a CMP-Neu5Ac synthetase, a sialic acid synthase, an UDP-GlcNAc-6-phosphate 2-epimerase and a sialyltransferase, and wherein the endogenous genes coding for sialic acid aldolase (NanA) and for ManNAc kinase (NanK) have been deleted or inactivated. The use of this prokaryotic biosynthesis route is very energy intensive for the cell. Furthermore, the described route for producing the sialylated oligosaccharides competes for the UDP-GlcNAc, which is essential for the cells own peptidoglycan synthesis. Building on this concept, Kang et al. have created a production host that does not use a sialic acid synthase, but the endogenous sialic acid aldolase, which has a less favorable chemical equilibrium (*Metabolic engineering* 14, 2012, 623-629).

EP1484406 describes the production of Neu5Ac using *E. coli* overexpressing N-acetylglucosamine 2-epimerase and Neu5Ac synthase, but needs N-acetylglucosamine (GlcNAc) as external precursor. In the described method, GlcNAc needs to be used as such. Therefore, the cells in EP1484406 need to be disrupted such that the GlcNAc can be used directly by the GlcNAc-2-epimerase. As described by Lundgren et al. (Org. Biomol. Chem., 2007, 5, 1903-1909) intact cells will convert the incoming GlcNAc to N-acetylglucosamine-6-phosphate (GlcNAc-6-P), which will be used by the cell for cell growth. This GlcNAc-6-P is not available intercellularly and can therefore not be used for the GlcNAc-2-epimerase, which needs a non-phosphorylated GlcNAc for epimerization to ManNAc. This explains why permeabilization of the cells of EP1484406 is necessary. As explained by Lundgren et al., the GlcNAc-6-P can be used for making Neu5Ac but this requires another synthesis pathway comprising UDP-GlcNAc as an intermediate, which is described above in WO2007101862. The resulting pathway further increases energy demand compared to the one described in the latter patent because uridylation of GlcNAc requires an extra ATP.

Deng et al. (Metabolic Engineering 7 (2005), 201-214) describes the production of GlcNAc via intracellular production of GlcNAc-6-P, which is then efficiently dephosphorylated and secreted into the medium as GlcNAc. According to Deng et al., this dephosphorylation happens upon export, more specifically in the periplasm of *Escherichia coli*. The extracellular produced GlcNAc described in this method, is not available for intracellular conversion. This method to produce GlcNAc requires a two-phase fed batch process, i.e., a cell growth phase followed by a GlcNAc production phase, which is only induced after the culture had reached a high cell density, to minimize inhibitory effects of phosphorylated amino sugars.

Others have attempted the same by heterologously expressing phosphatases and encountered the problem of reduced growth and strong metabolic burden (Lee and Oh, Metabolic engineering, 2015, 143-150). The main reason for the reduction in growth/biomass formation is the non-specificity of the phosphatase that is introduced, which dephosphorylates other essential phosphorylated compounds. Such modifications hence lead to reduced fitness and lower specific productivity. It furthermore leads to selective pressure to mutate the production pathway during production, which reduces the overall process stability.

The production pathways of sialic acid and sialylated oligosaccharides require the formation of high level of phosphorylated (e.g., GlcNAc-6-P) and nucleotide pathway intermediates. It is commonly understood that such formation leads to aspecific degradation of these intermediates by activation of aspecific phosphatases, which in turn leads to reduced fitness. In order to circumvent the effect of the expression of metabolic pathways on the growth of the production hosts, it is standard to use inducible expression systems. In this method first biomass is formed and later in the production process the production pathway is activated by for instance IPTG. This was applied by others for the production of sialic acid and sialylated oligosaccharides (WO2007101862; Priem et al. *Glycobiology* 12, 2002, 235-240; Kang et al., *Metabolic engineering* 14, 2012, 623-629; Yang et al., *Metabolic engineering* 43, 2017, 21-28). Apart from losing productivity and titer, another downside in the use of inducible systems is the excretion of intermediate pathway metabolites such as GlcNAc and ManNAc. This leads to the requirement of extra downstream processing steps for the purification, hence a higher production cost in the production of sialic acid, sialyllactose or other sialylated compounds.

The methods for producing sialylated compounds, discussed hereabove, are still insufficient in meeting the large demand of the biotechnological, pharmaceutical and medical industries. A metabolic engineering approach that successfully overcomes the problems referred to above, would represent a significant and long awaited advance in the field.

BRIEF SUMMARY

Surprisingly, a production pathway that does not require induction has been created, and does not require a UDP-GlcNAc epimerase, but allows constitutive expression that also allows better tuning of the metabolic pathway improving production and reducing byproduct formation during the production process.

According to one embodiment of this disclosure, there is provided a method for sialylated compound production with microorganisms that does not require induction.

According to a further embodiment of this disclosure, there is provided a production pathway that does not require a UDP-GlcNAc epimerase, and comprising modulating expression of phosphatase that does not pose a metabolic burden to the cell as was shown previously in the art. The further embodiment of this disclosure provides also an increased sialylated compound production by modulating the expression of phosphatase.

In another further embodiment, the above method, when combined with the constitutive expression of the genes of the metabolic pathway, also allows better tuning of the metabolic pathway reducing byproduct formation during the production process.

BRIEF DESCRIPTION OF THE DRAWINGS

FIG. 1 shows an exemplary pathway as used in example 2 for the production of sialic acid according to this disclosure.

FIG. 6 shows the parts of an alignment of the phosphatases of, from top to bottom, SEQ ID NOs: 58, 65, 42, 67, 56, 60, 63, 51, 43, 62, 47, 44, 61, 72, 49, 45, 53, 64, 46, 68, 69, 52, 54, 48, 55, 66, 57, 59, 50, and 71.

DETAILED DESCRIPTION

Figure 1A:
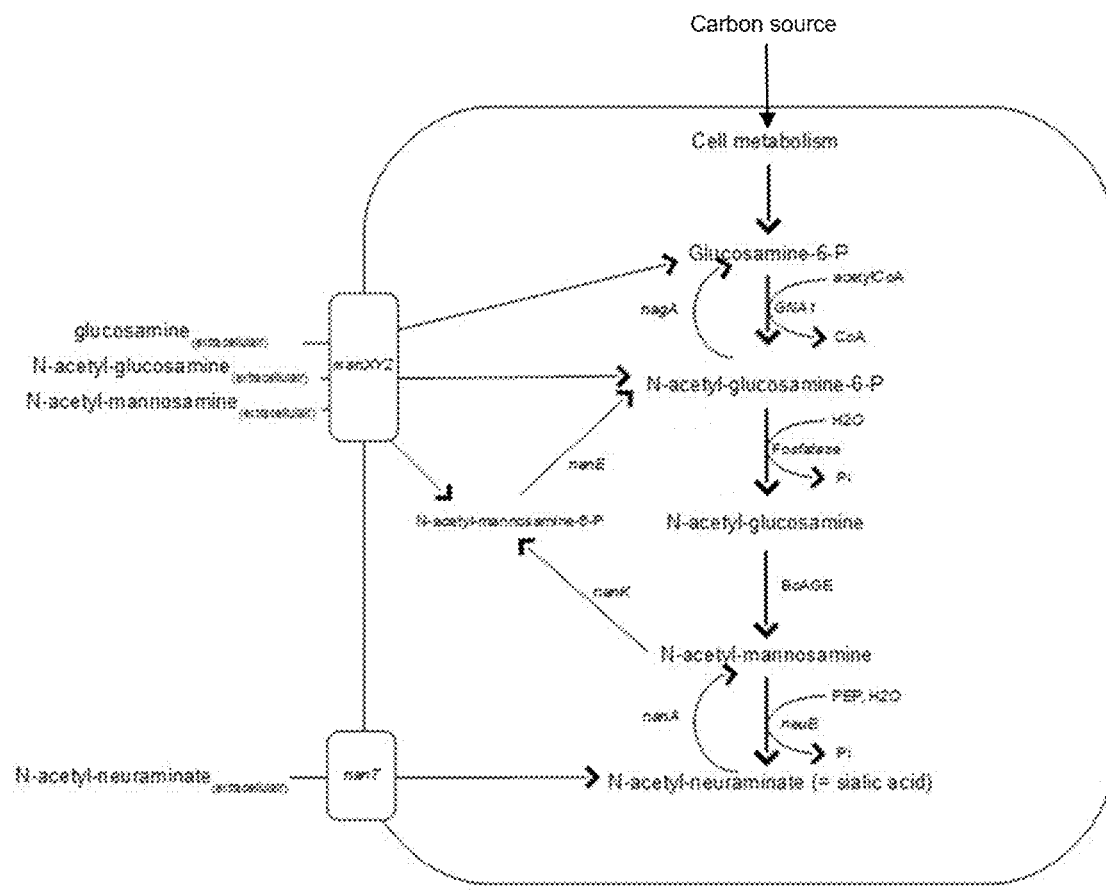
FIG. 1A shows the pathway without all KO and overexpression signs.

This disclosure describes an economical, more efficient and alternative biosynthesis route for the production of sialylated compounds using micro-organisms.

This disclosure provides a method of producing sialylated compounds by fermentative growth of micro-organisms.

In particular, this disclosure relates to a method for the production of sialylated compounds, wherein the method comprises culturing a microorganism in a culture medium. The microorganism intracellularly converts following reactions: N-acetylglucosamine-6-phosphate to N-acetylglucosamine, N-acetylglucosamine to N-acetylmannosamine, and N-acetyl-mannosamine to N-acetyl-neuraminate. Furthermore, this microorganism is unable to: i) convert N-acetylglucosamine-6-P to glucosamine-6-P, convert N-acetylglucosamine to N-acetylglucosamine-6-P, and iii) convert N-acetyl-neuraminate to N-acetyl-mannosamine.

Preferably, the conversion of N-acetylglucosamine-6-phosphate to N-acetylglucosamine is obtained by the action of an intracellularly expressed phosphatase. In another preferred embodiment the N-acetylglucosamine is converted to N-acetylmannosamine by an intracellularly expressed N-acetylmannosamine epimerase. In an alternative preferred embodiment the N-acetylmannosamine is converted by an intracellular expressed sialic acid synthase to N-acetyl-neuraminate. Even more preferably, the microorganism comprises all three enzymes such that the microorganism converts i) N-acetylglucosamine-6-phosphate to N-acetyl-glucosamine by action of an intracellularly expressed phosphatase, the N-acetylglucosamine to N-acetylmannosamine by an intracellularly expressed N-acetyl-mannosamine epimerase; and iii) the N-acetylmannosamine to N-acetyl-neuraminate by an intracellular expressed sialic acid synthase.

Preferably, the microorganism used in the method of this disclosure is unable to produce following enzymes i) a N-acetylglycosamine-6-phosphate deacetylase, a N-acetyl-glucosamine kinase, and iii) a N-acetylneuraminate aldolase.

This disclosure also provides a microorganism that expresses i) a phosphatase to dephosphorylate N-acetylglucosamine-6-phosphate to N-acetylglucosamine (EC 3.1.3), a GlcNAc 2-epimerase to convert N-acetylglucosamine (GlcNAc) to N-acetyl-mannosamine (manNac) (EC 5.1.3.8), and iii) a sialic acid synthetase to synthesize N-acetyl-neuraminate (Neu5Ac) from N-acetylmannosamine (ManNAc) (EC 2.5.1.56). Furthermore, this microorganism is unable to: i) convert N-acetylglucosamine-6-P to glucosamine-6-P, convert N-acetyl-glucosamine to N-acetyl-glucosamine-6-P, and iii) convert N-acetyl-neuraminate to N-acetyl-mannosamine.

In one aspect, this disclosure provides a micro-organism that is enabled to catalyze the following reactions: the intracellular conversion of N-acetylglucosamine-6-phosphate to N-acetylglucosamine, the intracellular conversion of N-acetylglucosamine to N-acetyl-mannosamine and, the intracellular conversion of N-acetylmannosamine to sialic acid.

It is generally accepted that N-acetylglucosamine-6-phosphate is naturally efficiently excreted out of the cell and meanwhile dephosphorylated by phosphatases in the periplasm (see p. 212, second column, Deng et al., Metabolic Engineering 7 (2005), 201-214). Therefore, without this disclosure, this excreted product would be unavailable for conversion to sialic acid. Furthermore, re-internalization occurs through transport proteins that phosphorylate the N-acetylglucosamine.

The use of an intracellular N-acetylglucosamine-2-epimerase ensures lower energy (ATP) consumption than the classical prokaryotic route (via UDP-N-acetylglucosamine). This enables a more efficient production of sialic acid, sialylated oligosaccharides and/or sialylated products with a healthier and more efficient strain. By optimizing expression levels, the unfavorable chemical equilibrium is overcome and no need of large amounts of free N-acetylglucosamine are necessary, as is in literature. Indeed, in the art, this enzyme is solely used in enzymatic reactions that use high concentrations of N-acetylglucosamine to produce N-acetyl-mannosamine. It would be hence logical that the use of an epimerase would require large amounts of intracellular formed GlcNAc, which is shown to be released in the medium (see Deng as described supra), however, this disclosure has proven this can be avoided. Another advantage of this disclosure over enzymatic methods, is that inexpensive substrates can be used in this disclosure, as for example a monosaccharide such as for example glucose, galactose or fructose, a disaccharide such as for example sucrose or maltose or a polyol, such as, but not limited to, glycerol. This enables an economic production method by fermentation.

Different phosphatases (EC 3.1.3.) that convert N-acetyl-glucosamine-6-phosphate into N-acetylglucosamine are described in the art and can be used in this disclosure. Phosphatases from the haloacid dehalogenase ("HAD") superfamily and the HAD-like family are described in the art. Examples from these families can be found in the enzymes expressed from genes yqaB, inhX, yniC, ybiV, yidA, ybjl, yigL or cof from *Escherichia coli*. One phosphatase that catalyzes this reaction is identified in *Blastocladiella emersonii*. Phosphatases are generally non-specific and the activity is generally not related to the family or structure. Other examples can thus be found in all phosphatase families. Specific phosphatases are easily identified and screened by well-known methods as described by Fahs et al. (ACS Chem. Biol., 2016, 11 (11), 2944-2961).

Preferably, the phosphatase of this disclosure is a HAD-like phosphatase. A HAD-like phosphatase as defined herein refers to any phosphatase polypeptide that comprises:
  any one or more of the following motifs as defined below:
    Motif 1: hDxDx[TV] (SEQ ID NO: 73), or
    Motif 2: [GSTDE][DSEN]x(1-2)[hP] x(1-2) [DGTS] (SEQ ID NOs: 74, 75, 76, 77),
      wherein h means a hydrophobic amino acid (A, I, L, M, F, V, P, G) and x can be any distinct amino acid.

In another preferred embodiment, HAD-like polypeptides typically have in increasing order of preference at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to any one of the polypeptides represented by SEQ ID NOs: 43, 44, 45, 47, 48, 50, 51, 52, 54, 55 or 57. Preferably, those polypeptides also comprise at least one of the above identified Motifs. More preferably, they comprise both motifs.

The overall sequence identity is determined using a global alignment algorithm, such as the Needleman Wunsch algorithm in the program GAP (GCG Wisconsin Package, Accelrys), preferably with default parameters and preferably with sequences of mature proteins (i.e., without taking into account secretion signals or transit peptides). Compared to overall sequence identity, the sequence identity will generally be higher when only conserved domains or motifs are considered.

In a preferred embodiment, the HAD-like polypeptide comprises any one of SEQ ID NOs: 43, 44, 45, 47, 48, 50, 51, 52, 54, 55 or 57.

In another preferred embodiment, the phosphatase is chosen from the HAD superfamily or the HAD-like phosphatase family. More preferably, the phosphatase is chosen from the group comprising: i) enzymes expressed by the genes yqaB, inhX, yniC, ybiV, yidA, ybjI, yigL or cof from *Escherichia coli*, ii) the phosphatase of *Blastocladiella emersonii* and iii) other phosphatase families.

Examples of N-acetyl-D-glucosmine-2-epimerase (EC 5.1.3.8) can be found in prokaryotes and eukaryotes. Examples for prokaryotes are found in cyanobacteria like for example *Acaryochloris marina, Anabaena variabilis, Anabaena marina, Nostoc punctiforme, Acaryochloris species, Anabaena species, Nostoc* species and *Synechocystis* species. They are also found in *Bacteroides* species like for example *Bacteroides ovatus* and *Bacteroides thetaiotaomicron* and in *Capnocytophaga canimorsus* and *Mobiluncus mulieris*. In eukaryotics, N-acetyl-D-glucosmine-2-epimerase is found in Glycin max, *Mus musculus, Homo sapiens, Rattus norvegicus, Bos Taurus, Sus scrofa, Canis lupus*. Preferably, in the method and microorganism of this disclosure, N-acetylmannosamine-2-epimerase is chosen from the group comprising i) N-acetylmannosamine-2-epimerase from cyanobacteria, more in particular from *Acaryochloris marina, Anabaena variabilis, Anabaena marina, Nostoc punctiforme, Acaryochloris species, Anabaena species, Nostoc* species and *Synechocystis* species; ii) N-acetylmannosamine-2-epimerase from *Bacteroides* species, more in particular from *Bacteroides ovatus, Bacteroides thetaiotaomicron, Capnocytophaga canimorsus* and *Mobiluncus mulieris*; iii) N-acetyl-D-glucosmine-2-epimerase from Glycin max, *Mus musculus, Homo sapiens, Rattus norvegicus, Bos Taurus, Sus scrofa* or *Canis lupus*.

N-acetyl neuraminate synthase (also called sialic acid synthase in the art) (EC 2.5.1.56) activity is found in several prokaryotic organisms like for example *Streptococcus agalatiae, Bacillus subtilis, Legionella pneumophilla, Campylobacter jejuni, Idiomarina loihiensis, Moritella viscosa, Aliivibrio salmonicida, Escherichia coli, Methanocaldococcus jannaschi, Clostridium sordellii, Butyrivibrio proteoclasticus, Micromonas commoda* or *Neisseria* meningitis. Preferably, in the method and microorganism of this disclosure, the sialic acid (or N-acetyl neuraminate) synthase is chosen from the group comprising: sialic acid synthase from *Streptococcus agalatiae, Bacillus subtilis, Legionella pneumophilla, Campylobacter jejuni, Idiomarina loihiensis, Moritella viscosa, Aliivibrio salmonicida, Escherichia coli, Methanocaldococcus jannaschi, Clostridium sordellii, Butyrivibrio proteoclasticus, Micromonas commoda* or *Neisseria* meningitis.

In one preferred aspect, any one or more of the phosphatase, N-acetyl-mannosamine epimerase and sialic acid synthase is overexpressed in the microorganism. In an alternative preferred aspect, any one or more of the phosphatase, N-acetyl-mannosamine epimerase and sialic acid synthase is introduced and expressed in the microorganism.

In another aspect, the microorganism lacks the genes encoding for following enzymes i) a N-acetylglycosamine-6-phosphate deacetylase, ii) a N-acetylglucosamine kinase, and iii) a N-acetylneuraminate aldolase. In another preferred aspect, the genes encoding for following enzymes i) a N-acetylglycosamine-6-phosphate deacetylase, ii) a N-acetylglucosamine kinase, and iii) a N-acetylneuraminate aldolase are reduced in activity, preferably the genes are deleted or knocked-out, in the microorganism.

In another preferred aspect, the microorganism further encodes a protein that facilitates uptake of lactose and lacks enzymes that metabolize lactose. Methods to produce microorganisms that resist lactose killing and the resulting microorganisms are described in WO2016/075243, which is herein incorporated by reference.

In a preferred aspect the microorganisms of, and used in the method of, this disclosure also express a CMP-sialic acid synthase (EC 2.7.7.43) and a sialyltransferase (EC 2.4.99.1) in order to activate the sialic acid and transfer it to a desired compound.

In a preferred aspect, the N-acetylglucosamine-6-phosphate is obtained by introducing a glucosamine-phosphate N-acetyltransferase (EC 2.3.1.4), which uses intracellular glucosamine-6-phosphate as a substrate. In most microorganisms, glucosamine-6-phosphate is naturally present in the cell, but the intracellular production can be elevated by expressing a L-glutamine:D-fructose-6-phosphate aminotransferase without inhibition, obtained either through protein engineering or by screening natural enzymes, such as present in gram positive bacteria (Deng et al., Metabolic Engineering 7 (2005), 201-214).

In this disclosure, the expression of the genes to convert N-acetylglucosamine-6-phosphate to N-acetyl-neuraminate or sialic acid are optimized in a way that enables intracellular dephosphorylation of N-acetylglucosamine-6-phosphate, prevents toxic accumulation of N-acetylglucosamine-6-phosphate and prevents excretion of N-acetylglucosamine and/or N-acetylmannosamine. The optimization is the result of the use of constitutive expression of the genes of the production pathway. In a preferred embodiment, this disclosure prevents the excretion of at least 10%, 20%, 30%, 35%, 40%, 45%, 50%, or 60% of the formed N-acetylglucosamine and/or N-acetylmannosamine. In a further preferred embodiment, the microorganism produces less extracellular N-acetylglucosamine and/or N-acetyl-mannosamine than sialylated compound. More preferably, the microorganism produces less than 50%, 40%, 30%, 20%, 10%, 5%, 2% extracellular N-acetylglucosamine and/or N-acetyl-mannosamine than sialylated compound. In another preferred embodiment of this disclosure the microorganism produces equal or more than 50%, 60%, 70%, 80%, 90%, 95%, 98% extracellular sialylated compound on total extracellular carbohydrate.

In a particular aspect, this disclosure relates to a method for synthesis of sialylated compounds, without any exogenous sialic acid addition to the culture medium.

The sialylated compound can be N-acetylneuramic acid, a sialylated oligosaccharide, a sialylated lipid, sialylated glycolipids (such as, but not limited to gangliosides, ceramides), a sialylated protein or a sialylated aglycon.

A sialylated oligosaccharide is a charged sialic acid containing oligosaccharide, i.e., an oligosaccharide having a sialic acid residue. It has an acidic nature. Some examples are 3-SL (3-sialyllactose), 3-sialyllactosamine, 6-SL (6-sialyllactose or n-acetylneuraminate alfa 2,6 galactosyl beta 1,4 Glucose), 6-sialyllactosamine, oligosaccharides comprising 6-sialyllactose, SGG hexasaccharide (Neu5Ac alfa-2,3Gal beta-1,3GalNac beta-1,3Gala-1,4Gal beta-1,4Gal), sialylated tetrasaccharide (Neu5Ac-alfa-2,3Gal beta-1,4GlcNAc beta-14GlcNAc), pentasaccharide LSTD (Neu5Ac alfa-2,3Gal beta-1,4GlcNAc beta-1,3Gal beta-1,4Glc), sialylated lacto-N-triose, sialylated lacto-N-tetraose, sialyllacto-N-neotetraose, monosialyllacto-N-hexaose, disialyllacto-N-hexaose I, monosialyllacto-N-neohexaose I, monosialyllacto-N-neohexaose II, disialyllacto-N-neohexaose, disialyllacto-N-tetraose, disialyllacto-N-hexaose II, sialyllacto-N-tetraose a, disialyllacto-N-hexaose I, sialyllacto-N-tetraose b, 3-sialyl-3-fucosyllactose, di sialomonofucosyllacto-N-neohexaose, monofucosylmonosialyllacto-N-octaose (sialyl Lea), sialyllacto-N-fucohexaose II, disialyllacto-N-fucopentaose II, monofucosyldisialyllacto-N-tetraose and oligosaccharides bearing one or several sialic acid residue(s), including but not limited to: oligosaccharide moieties of the gangliosides selected from GM3 (3sialyllactose, Neu5Aca-2,3Gal beta-4Glc) and oligosaccharides comprising the GM3 motif, GD3 Neu5Aca-2,8Neu5Aca-2,3Gal beta-1,4Glc GT3 (Neu5Aca-2,8Neu5Aca-2,8Neu5Aca-2,3Gal beta-1,4Glc); GM2 GalNAc beta-1,4 (Neu5Aca-2,3)Gal beta-1,4Glc, GM1 Gal beta-1,3GalNAc beta-1,4(Neu5Aca-2,3)Gal beta-1,4Glc, GD1a Neu5Aca-2,3Gal beta-1,3GalNAc beta-1,4(Neu5Aca-2,3)Gal beta-1,4Glc GT1a Neu5Aca-2,8Neu5Aca-2,3Gal beta-1,3GalNAc beta-1,4(Neu5Aca-2,3)Gal beta-1,4Glc GD2 GalNAc beta-1,4(Neu5Aca-2,8Neu5Aca2,3)Gal beta-1,4Glc GT2 GspalNAc beta-1,4(Neu5Aca-2,8Neu5Aca-2,8Neu5Aca2,3)Gal beta-1,4Glc GD1b, Gal beta-1,3GalNAc beta-1,4(Neu5Aca-2,8Neu5Aca2,3)Gal beta-1,4Glc GT1b Neu5Aca-2,3Gal beta-1,3GalNAc beta-1,4(Neu5Aca-2,8Neu5Aca2,3)Gal beta-1,4Glc GQ1b Neu5Aca-2,8Neu5Aca-2,3Gal beta-1,3GalNAc beta-1,4(Neu5Aca-2,8Neu5Aca2,3)Gal beta-1,4Glc GT1c Gal beta-1,3GalNAc beta-1,4(Neu5Aca-2,8Neu5Aca-2,8Neu5Aca2,3)Gal beta-1,4Glc GQ1c, Neu5Aca-2,3Gal beta-1,3GalNAc beta-1,4(Neu5Aca-2,8Neu5Aca-2,8Neu5Aca2,3)Gal beta-1,4Glc GP1c Neu5Aca-2,8Neu5Aca-2,3Gal beta-1,3GalNAc beta-1,4 (Neu5Aca-2,8Neu5Aca-2,8Neu5Aca2,3)Gal beta-1,4Glc GD1a Neu5Aca-2,3Gal beta-1,3(Neu5Aca-2,6)GalNAc beta-1,4Gal beta-1,4Glc Fucosyl-GM1 Fuca-1,2Gal beta-1,3GalNAc beta-1,4(Neu5Aca-2,3)Gal beta-1,4Glc; all of which may be extended to the production of the corresponding gangliosides by reacting the above oligosaccharide moieties with ceramide or synthetizing the above oligosaccharides on a ceramide.

The term micro-organism or organism or cell as indicated above refers to a microorganism chosen from the list comprising a bacterium, a yeast, or a fungus, or, refers to a plant or animal cell. The latter bacterium preferably belongs to the phylum of the Proteobacteria or the phylum of the Firmicutes or the phylum of the Cyanobacteria or the phylum Deinococcus-Thermus. The latter bacterium belonging to the phylum Proteobacteria belongs preferably to the family Enterobacteriaceae, preferably to the species *Escherichia coli*. The latter bacterium preferably relates to any strain belonging to the species *Escherichia coli* such as but not limited to *Escherichia coli* B, *Escherichia coli* C, *Escherichia coli* W, *Escherichia coli* K12, *Escherichia coli* Nissle. More specifically, the latter term relates to cultivated *Escherichia coli* strains—designated as *E. coli* K12 strains—which are well-adapted to the laboratory environment, and, unlike wild type strains, have lost their ability to thrive in the intestine. Well-known examples of the *E. coli* K12 strains are K12 Wild type, W3110, MG1655, M182, MC1000, MC1060, MC1061, MC4100, JM101, NZN111 and AA200. Hence, this disclosure specifically relates to a mutated and/or transformed *Escherichia coli* strain as indicated above wherein the *E. coli* strain is a K12 strain. More specifically, this disclosure relates to a mutated and/or transformed *Escherichia coli* strain as indicated above wherein the K12 strain is *E. coli* MG1655. The latter bacterium belonging to the phylum Firmicutes belongs preferably to the Bacilli, preferably Lactobacilliales, with members such as *Lactobacillus lactis, Leuconostoc mesenteroides*, or Bacillales with members such as from the species *Bacillus, Bacillus subtilis* or, *B. amyloliquefaciens*. The latter Bacterium belonging to the phylum Actinobacteria, preferably belonging to the family of the Corynebacteriaceae, with members *Corynebacterium glutamicum* or *C. afermentans*, or belonging to the family of the of the Streptomycetaceae with members *Streptomyces griseus* or *S. fradiae*. The latter yeast preferably belongs to the phylum of the Ascomycota or the phylum of the Basidiomycota or the phylum of the Deuteromycota or the phylum of the Zygomycetes. The latter yeast belongs preferably to the genus *Saccharomyces, Pichia, Hansenula, Kluyveromyces, Yarrowia* or Starmerella. The latter fungus belongs preferably to the genus *Rhizopus, Dictyostelium, Penicillium, Mucor* or *Aspergillus*.

The culture medium for the production host can optionally comprise an exogenous precursor or this precursor can be produced by the strain itself, such as a glycan like for example lactose, lactosamine, lacto-N-triose, lacto-N-tetraose, lacto-N-neotetraose; an oligosaccharide; a peptide; a lipid or an aglycon. In one particular aspect, the process of this disclosure is based on the active uptake of an exogenous precursor, such as for example a mono, di or tri-saccharide, more particularly an exogenous precursor selected from lactose, N-acetyllactosamine, lacto-N-biose, galactose, beta-galactoside, and alpha-galactoside such as but not limited to globotriose (Gal-alpha-1,4Gal-beta-1,4Glc), while the microorganisms are growing on an inexpensive carbon substrate, such as a disaccharide such as sucrose or maltose. Moreover, these microorganisms are also able to grow on glucose, fructose or glycerol. The expression exogenous precursor is intended to denote a compound involved in the biosynthetic pathway of the product according to this disclosure that is internalized by the microorganism.

In one aspect, this disclosure provides for method for production of sialylated forms of lacto-N-triose, lacto-N-tetraose or lacto-N-neotetraose. Any one of these three molecules are synthetized by the micro-organism via the activity of a galactosyltransferase (EC 2.4.1.38), preferably originating from the group comprising *Homo sapiens, Bos taurus*, Mus mulatta, *Gallus gallus, Danio rerio, Helicobacter pylori* and *Haemophilus* ducrey and/or a N-acetylglucosaminyltransferase (EC 2.4.1.90) preferably originating from the group comprising *Bos Taurus, Homo Sapiens* and *Mus Musculus*. To enhance the formation of these oligosaccharides the genes coding for UDP sugar hydrolase and galactose-1-phosphate uridylyltransferase are lacking, reducing in activity or knocked out in the microorganism.

In another aspect a method for producing a sialylated oligosaccharide is provided in which the method comprises culturing a microorganism as described above and wherein the microorganism produces internally, activated N-acetylneuraminate as donor substrate for a sialyltransferase; and wherein the method further comprises culturing the microorganism in a culture medium that comprises an exogenous precursor selected from the group consisting of lactose, N-acetyllactosamine, lacto-N-biose, galactose, beta-galactoside, and alpha-galactoside such as but not limited to globotriose (Gal-alpha-1,4Gal-beta-1,4Glc)galactose. The exogenous precursor is actively taken up into the microorganism and the exogenous precursor is the acceptor substrate for the sialytransferase for producing the sialylated oligosaccharide.

In a further aspect, the method according to this disclosure provides for the production of 3sialyllactose or 6sialyllactose. In this method the microorganism is cultivated at high cell density on a carbon substrate, such as glucose or glycerol, and fed with lactose. The lactose is internalized by the lactose permease and sialylated by the recombinant sialyltransferase using the CMP-N-acetyl-neuraminate endogenously generated from N-acetylglucosamine.

The microorganism or cell of this disclosure is capable to grow on a monosaccharide, disaccharide, oligosaccharide, polysaccharide, polyol, a complex medium or a mixture thereof as the main carbon source. With the term main is meant the most important carbon source for biomass formation, carbon dioxide and/or by-products formation (such as acids and/or alcohols, such as acetate, lactate, and/or ethanol), i.e., 20, 30, 40, 50, 60, 70, 75, 80, 90, 95, 98, 99% of all the required carbon is derived from the above-indicated carbon source. In one embodiment of this disclosure, the carbon source is the sole carbon source for the organism, i.e., 100% of all the required carbon is derived from the above-indicated carbon source.

In a further preferred embodiment, the microorganism or cell of this disclosure is using a split metabolism having a production pathway and a biomass pathway as described in WO2012/007481, which is herein incorporated by reference. The organism can, for example, be genetically modified to accumulate fructose-6-phosphate by altering the genes selected from the phosphoglucoisomerase gene, phosphofructokinase gene, fructose-6-phosphate aldolase gene, fructose isomerase gene, and/or fructose:PEP phosphotransferase gene.

With the term monosaccharide is meant a sugar that is not decomposable into simpler sugars by hydrolysis, is classed as either an aldose or ketose, and contains one or more hydroxyl groups per molecule. Examples are glucose, fructose, galactose, mannose, ribose and/or arabinose.

With the term disaccharide is meant a sugar that is composed of two monosaccharides that are chemically bound. Examples are maltose, sucrose, lactose, trehalose, cellobiose and/or chitobiose.

With the term oligosaccharide is meant a sugar that is composed of three to ten monosaccharides that are chemically bound. Examples are maltotriose, fructo-oligosaccharides, galacto-oligosaccharides, mannan oligosaccharides, isomaltooligosaccharide, human milk oligosaccharides and/or glucooligosaccharides.

With the term polyol is meant an alcohol containing multiple hydroxyl groups. For example, glycerol, sorbitol, or mannitol.

With the term complex medium is meant a medium for which the exact constitution is not determined. Examples are molasses, corn steep liquor, peptone, tryptone or yeast extract.

Production of sialylated compounds can be increased by adding precursors to the medium, such as N-acetylglusosamine, N-acetylmannosamine, glutamine, glutamate, phosphoenolpyruvate and/or pyruvate.

The sialylated compounds produced in the method of this disclosure as described above may be recovered using various methods, or a combination thereof, known in the art.

Depending on the produced sialylated compound, the compound is available in the extracellular fraction or retained in the cells. When the produced sialylated compound is retained in the cells, the sialylated compound will first be released from the cells by cell disruption. Again depending on the produced sialylated compound, the cells may be separated from the extracellular fraction. In the other case, cells are disrupted without first separation from the extracellular fraction, wherein cells are disrupted by techniques such as, but not limited to, heating, freeze thawing and/or shear stress through sonication, mixing and/or French press. The extracellular and/or intracellular fraction may be separated from the cells and/or cell debris by centrifugation, filtration, microfiltration, and nanofiltration. Flocculating agents may be used to aid in product separation. The sialylated compounds in the extracellular or intracellular fraction may be extracted by ion exchange, ultra- or nanofiltration or electrodialysis, chromatography such as size exclusion, ion chromatography and simulated moving bed. Another example of filtering the sialylated compounds from liquid phase is by filtration using a deep bed filter with cotton and activated carbon or carbon filter, where after the permeate is passed through a carbon polisher followed by e.g., a 0.2 micron microfiltration membrane system to remove color, micro-organisms and suspended carbon particles. Thereafter the sialylated compound may be concentrated in a vacuum evaporator to obtain a concentrate. The concentrate can be precipitated and/or dried through heat drying, spray drying and/or lyophilization to obtain high purity sialylated compound. An amorphous form powder can then be obtained. This amorphous powder may further be crystallized to obtain crystalline sialylated compound.

In exemplary embodiment, sialylated compounds may be isolated from the culture medium using methods known in the art for fermentations. For example, cells may be removed from the culture medium by centrifugation, filtration, flocculation, decantation, or the like. Then, the sialylated compounds may be isolated from the extracellular fraction using methods such as ion-exchange. A further purification of the sialylated compounds may be accomplished, for example, by nanofiltration or ultrafiltration or ion exchange to remove any remaining DNA, protein, LPS (endotoxins), or other impurity.

In another exemplary embodiment, sialyllactose may be isolated from the culture medium using methods known in the art for fermentations. For example, cells may be removed from the culture medium by centrifugation, filtration, flocculation, decantation, or the like. Then, the sialyllactose may be isolated from the extracellular fraction using methods such as ion-exchange. A further purification of the sialyllactose may be accomplished, for example, by nanofiltration or ultrafiltration or ion exchange to remove any remaining DNA, protein, LPS (endotoxins), or other impurity. Another purification and formulation step is accomplished by crystallization or precipitation of the product. Another formulation step is to spray dry or lyophilize sialyllactose.

The sialylated compound may contain a counter ion, such as, a monovalent ion, such as a proton, sodium ion, potassium, a divalent ion, such as calcium magnesium, iron, or, a trivalent ion such as iron, or a combination of ions.

Throughout the disclosure of the present disclosure the term sialic acid, N-acetyl neuraminate and N-acetyl neuraminic acid are used interchangeably.

As used herein, the term intracellular or intracellularly in e.g., intracellularly converting, intracellularly production, intracellularly expressed, intracellular formed must be understood to mean within the cell of the microorganism. The term extracellular must be understood to mean outside of the cell.

Further definitions used throughout the present specification:

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag»100 epitope, c-myc epitope, FLAG(R)-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break a-helical structures or beta-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W. H. Freeman and Company (Eds) and Table 1 below).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | As, |
| Cys | Ser |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, 17-Gen in vitro mutagenesis (USB, Cleveland, OH), Quick-Change Site Directed mutagenesis (Stratagene, San Diego, CA), PCR-mediated site-directed mutagenesis or other site-directed mutagenesis protocols.

Derivatives

"Derivatives" include peptides, oligopeptides, polypeptides that may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides, which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule that is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain, Motif/Consensus Sequence/Signature

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc.

Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e., spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimize alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

Reciprocal BLAST

Typically, this involves a first BLAST involving BLASTing a query sequence (for example using any of the sequences listed in Table A of the Examples section) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived. The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbor joining tree, to help visualize clustering of related genes and to identify orthologues and paralogues.

Construct

Additional regulatory elements may include transcriptional as well as translational enhancers. Those skilled in the art will be aware of terminator and enhancer sequences that may be suitable for use in performing this disclosure. An intron sequence may also be added to the 5 untranslated region (UTR) or in the coding sequence to increase the amount of the mature message that accumulates in the cytosol, as described in the definitions section. Other control sequences (besides promoter, enhancer, silencer, intron sequences, 3UTR and/or 5UTR regions) may be protein and/or RNA stabilizing elements. Such sequences would be known or may readily be obtained by a person skilled in the art.

The genetic constructs of this disclosure may further include an origin of replication sequence that is required for maintenance and/or replication in a specific cell type. One example is when a genetic construct is required to be maintained in a bacterial cell as an episomal genetic element (e.g., plasmid or cosmid molecule).

For the detection of the successful transfer of the nucleic acid sequences as used in the methods of this disclosure and/or selection of transgenic microorganisms comprising these nucleic acids, it is advantageous to use marker genes (or reporter genes). Therefore, the genetic construct may optionally comprise a selectable marker gene. The marker genes may be removed or excised from the transgenic cell once they are no longer needed. Techniques for marker removal are known in the art, useful techniques are described above in the definitions section.

Regulatory Element/Control Sequence/Promoter

The terms "regulatory element," "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and that is involved in recognizing and binding of RNA polymerase and other proteins, thereby directing transcription of an operably linked nucleic acid. Encompassed by the aforementioned terms are transcriptional regulatory sequences derived from a classical eukaryotic genomic gene (including the TATA box, which is required for accurate transcription initiation, with or without a CCAAT box sequence) and additional regulatory elements (i.e., upstream activating sequences, enhancers and silencers) that alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

Constitutive Promoter

A "constitutive promoter" refers to a promoter that is transcriptionally active during most, but not necessarily all, phases of growth and development and under most environmental conditions, in at least one cell, tissue or organ.

Transgenic/Transgene/Recombinant

For the purposes of this disclosure, "transgenic," "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to this disclosure, all those constructions brought about by recombinant methods in which either:

(a) the nucleic acid sequences encoding proteins useful in the methods of this disclosure, or
(b) genetic control sequence(s), which is operably linked with the nucleic acid sequence according to this disclosure, for example a promoter, or
(c) a) and b) are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original microorganism or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example, the naturally occurring combination of the natural promoter of the nucleic acid sequences with the corresponding nucleic acid sequence encoding a polypeptide useful in the methods of this disclosure, as defined above— becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic microorganism for the purposes of this disclosure is thus understood as meaning, as above, that the nucleic acids used in the method of this disclosure are not present in, or originating from, the genome of the microorganism, or are present in the genome of the microorganism but not at their natural locus in the genome of the microorganism, it being possible for the nucleic acids to be expressed homologously or heterologously. However, as mentioned, transgenic also means that, while the nucleic acids according to this disclosure or used in the inventive method are at their natural position in the genome of a microorganism, the sequence has been modified with regard to the natural sequence, and/or that the regulatory sequences of the natural sequences have been modified. Transgenic is preferably understood as meaning the expression of the nucleic acids according to this disclosure at an unnatural locus in the genome, i.e., homologous or, preferably, heterologous expression of the nucleic acids takes place. Preferred transgenic microorganism are mentioned herein.

It shall further be noted that in the context of this disclosure, the term "isolated nucleic acid" or "isolated polypeptide" may in some instances be considered as a synonym for a "recombinant nucleic acid" or a "recombinant polypeptide," respectively, and refers to a nucleic acid or polypeptide that is not located in its natural genetic environment and/or that has been modified by recombinant methods.

Modulation

The term "modulation" means in relation to expression or gene expression, a process in which the expression level is changed by the gene expression in comparison to the control microorganism, the expression level may be increased or decreased. The original, unmodulated expression may be of any kind of expression of a structural RNA (rRNA, tRNA) or mRNA with subsequent translation. For the purposes of this disclosure, the original unmodulated expression may also be absence of any expression. The term "modulating the activity" shall mean any change of the expression of the inventive nucleic acid sequences or encoded proteins, which leads to increased production yield and/or increased growth of the microorganisms. The expression can increase from zero (absence of, or immeasurable expression) to a certain amount, or can decrease from a certain amount to immeasurable small amounts or zero.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level. For the purposes of this disclosure, the original wild-type expression level might also be zero, i.e., absence of expression or immeasurable expression.

Methods for increasing expression of genes or gene products are well documented in the art and include, for example, overexpression driven by appropriate promoters, the use of transcription enhancers or translation enhancers. Isolated nucleic acids that serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a microorganism cell in the proper orientation and distance from a gene of this disclosure so as to control the expression of the gene.

If polypeptide expression is desired, it is generally desirable to include a polyadenylation region at the 3-end of a polynucleotide coding region. The polyadenylation region can be derived from the natural gene, from a variety of other microorganism genes, or from T-DNA.

Moreover, this disclosure relates to the following specific embodiments:

1. Method for the production of sialylated compounds, the method comprising:
   culturing a microorganism in a culture medium, the culture medium optionally comprising an exogenous precursor,
   wherein the microorganism intracellularly converts N-acetylglucosamine-6-phosphate to N-acetylglucosamine, the N-acetylglucosamine to N-acetylmannosamine and the N-acetylmannosamine to N-acetyl-neuraminate; and
   wherein the microorganism is unable to i) convert N-acetylglucosamine-6-P to glucosamine-6-P, convert N-acetyl-glucosamine to N-acetyl-glucosamine-6-P, and iii) convert N-acetyl-neuraminate to N-acetyl-mannosamine.
2. The method according to embodiment 1 wherein:
   i) the conversion of N-acetylglucosamine-6-phosphate to N-acetylglucosamine is obtained by the action of an intracellularly expressed phosphatase,
   ii) the N-acetylglucosamine to N-acetylmannosamine conversion is performed by an intracellularly expressed N-acetylmannosamine epimerase; and
   iii) intracellular expressed sialic acid synthase converts the N-acetyl-mannosamine to N-acetyl-neuraminate.
3. The method according to any one of embodiment 1 or 2 wherein the organism is unable to produce following enzymes i) a N-acetylglycosamine-6-phosphate deacetylase, a N-acetylglucosamine kinase, and iii) a N-acetylneuraminate aldolase.
4. The method according to any one of embodiment 1 to 3, wherein all the conversions are catalyzed by enzymes encoded by constitutively expressed genes.
5. The method according to embodiment 2 wherein the phosphatase is chosen from the HAD superfamily or the HAD-like phosphatase family, preferably the phosphatase is chosen from the group comprising: i) enzymes expressed by the genes yqaB, inhX, yniC, ybiV, yidA, ybjI, yigL or cof from *Escherichia coli*, ii) the phosphatase of *Blastocladiella emersonii* and iii) other phosphatase families, more preferably the phosphatase is a HAD-like phosphatase polypeptide as defined in the claims.
6. The method according to any one of the embodiments 2, 3, 4 or 5, wherein the N-acetylmannosamine-2-epimerase is chosen from the group comprising i) N-acetylmannosamine-2-epimerase from cyanobacteria, more in particular from *Acaryochloris marina, Anabaena variabilis, Anabaena marina, Nostoc punctiforme, Acaryochloris species, Anabaena species, Nostoc* species and *Synechocystis* species; ii) N-acetylmannosamine-2-epimerase from *Bacteroides* species, more in particular from *Bacteroides ovatus, Bacteroides thetaiotaomicron, Capnocytophaga canimorsus* and *Mobiluncus mulieris*; iii) N-acetyl-D-glucosmine-2-epimerase from Glycin max, *Mus musculus, Homo sapiens, Rattus norvegicus, Bos Taurus, Sus scrofa* or *Canis lupus*.
7. The method according to any one of the embodiments 2, 3, 4, 5 or 6, wherein the sialic acid synthase is chosen from the group comprising: sialic acid synthase from *Streptococcus agalatiae, Bacillus subtilis, Legionella pneumophilla, Campylobacter jejuni, Idiomarina loihiensis, Moritella viscosa, Aliivibrio salmonicida, Escherichia coli, Methanocaldococcus jannaschi, Clostridium sordellii, Butyrivibrio proteoclasticus, Micromonas commoda* or *Neisseria* meningitis.
8. The method according to any one of the preceding embodiments, wherein the sialylated compound is selected from the group consisting of N-acetylneuramic acid, sialylated oligosaccharide, sialylated lipids, sialylated protein, sialylated aglycon.
9. The method according to the previous embodiment, wherein the sialylated compound is a sialylated oligosaccharide.
10. The method according to embodiment 9, wherein the sialylated oligosaccharide is sialyllactose, preferably any one of 3-SL or 6-SL.
11. The method according to embodiment 9, wherein the sialylated oligosaccharide is disialyl lacto-N-tetraose.
12. The method according to embodiment 8, wherein the sialylated compound is N-acetylneuraminic acid.
13. The method according to any one of embodiment 1 to 10 wherein the sialylated compound is a sialylated lacto-N-triose, lacto-N-tetraose or a lacto-N-neotetraose, and wherein the microorganism further comprises the activity of a galactosyltransferase (EC 2.4.1.38), preferably the galactosyltransferase originates from the group comprising *Homo sapiens, Bos taurus*, Mus mulatta, *Gallus gallus, Danio rerio, Helicobacter pylori* and *Haemophilus* ducrey; and/or the microorganism comprises the activity of a N-acetylglucosaminyltransferase (EC 2.4.1.90), preferably the N-acetylglucosaminyltransferase originates from the group comprising *Bos taurus, Homo sapiens* and *Mus musculus*.
14. The method according to embodiment 13 wherein the microorganism is unable to express the genes coding for UDP sugar hydrolase and galactose-1-phosphate uridylyltransferase.
15. The method according to any one of embodiments 1 to 14, wherein the microorganism produces less than 50%, 40%, 30%, 20%, 10%, 5%, 2% extracellular N-acetylglucosamine and/or N-acetylmannosamine than sialylated compound and/or the micro-organism produces equal or more than 50%, 60%, 70%, 80%, 90%, 95%, 98% sialylated compound on total carbohydrate.
16. A method for producing a sialylated oligosaccharide, comprising:
   a) culturing a microorganism according to the method of any one of embodiments 1 to 7, 14 and 15, and wherein the microorganism produces internally, activated N-acetylneuraminate as donor substrate for a sialyltransferase; and
   b) culturing the microorganism in a culture medium comprising an exogenous precursor selected from the group consisting of lactose, N-acetyllactosamine, lacto-N-biose, galactose, beta-galactoside, and alpha-galactoside such as but not limited to globotriose (Gal-alpha-1,4Gal-beta-1,4Glc)galactose, wherein active uptake into the microorganism of the exogenous precursor occurs and wherein the exogenous precursor is the acceptor substrate for the sialyltransferase for producing the sialylated oligosaccharide.
17. The method according to embodiment 2, wherein any one or more of the phosphatase, N-acetylmannosamine epimerase and sialic acid synthase is overexpressed in the microorganism.
18. The method according to embodiment 2, wherein any one or more of the phosphatase, N-acetylmannosamine 19. The method according to embodiment 3, wherein the microorganism lacks the genes encoding for following enzymes i) a N-acetylglycosamine-6-phosphate deacetylase, ii) a N-acetylglucosamine kinase, and iii) a N-acetylneuraminate aldolase.
20. The method according to embodiment 3, wherein in the microorganism the genes encoding for following enzymes i) a N-acetylglycosamine-6-phosphate deacetylase, ii) a N-acetylglucosamine kinase, and iii) a N-acetylneuraminate aldolase are reduced in activity, preferably the genes are deleted or knocked-out.
21. The method according to any one of the embodiments 1 to 20, wherein the microorganism further encodes a protein that facilitates uptake of lactose and lacks enzymes that metabolize lactose.
22. The method according to any one of embodiments 1 to 21, wherein the microorganism is a bacteria, preferably an *Escherichia coli* strain, more preferably an *Escherichia coli* strain, which is a K12 strain, even more preferably the *Escherichia coli* K12 strain is *Escherichia coli* MG1655.
23. The method according to any one of embodiments 1 to 21, wherein the microorganism is a yeast.
24. The method according to any one of embodiments 1 to 23, wherein the exogenous precursor is chosen from the group comprising lactose, galactose, beta-galactoside, and alpha-galactoside, such as globotriose (Gal-alpha-1,4Gal-beta-1,4Glc).
25. A microorganism for the production of sialylated compounds, the microorganism:
    intracellularly converts N-acetylglucosamine-6-phosphate to N-acetylglucosamine, the N-acetylglucosamine to N-acetylmannosamine and the N-acetylmannosamine to N-acetyl-neuraminate; and
    is unable to i) convert N-acetylglucosamine-6-P to glucosamine-6-P, ii) convert N-acetyl-glucosamine to N-acetyl-glucosamine-6-P, and iii) convert N-acetyl-neuraminate to N-acetyl-mannosamine.
26. A microorganism for the production of a sialylated compound, the microorganism being defined in any one of embodiments 2 to 24.
27. A cell culture medium comprising lactose as precursor and the microorganism of any one of embodiments 25 or 26.
28. The method according to one of embodiments 1 to 24, for the production of 3sialyllactose or 6sialyllactose, wherein the microorganism is cultivated at high cell density on a carbon substrate, such as glucose or glycerol, and fed with lactose that is internalized by the lactose permease and sialylated by the recombinant sialyltransferase using the CMP-N-acetyl-neuraminate endogenously generated from N-acetylglucosamine.
29. The method according to any one of embodiments 1 to 24, wherein the sialylated compound is isolated from the culture medium by means of a unit operation selected from the group centrifugation, filtration, microfiltration, ultrafiltration, nanofiltration, ion exchange, electrodialysis, chromatography, simulated moving bed, evaporation, precipitation, crystallization, lyophilization and/or spray drying.
30. A sialylated compound produced according to the method described in any one of embodiments 1 to 24, wherein the sialylated compound is purified by centrifugation and/or filtration, ion-exchange, concentration through evaporation or nanofiltration, formulation through crystallization or spraydrying or lyophilization.
31. A sialylated compound produced according to the method described in any one of embodiments 1 to 24, wherein the sialylated compound is added to food formulation, feed formulation, pharmaceutical formulation, cosmetic formulation, or agrochemical formulation.
32. The method according to any one of embodiments 1 to 24, wherein the culture medium comprises any one or more of the following: a monosaccharide, disaccharide, oligosaccharide, polysaccharide, polyol, a complex medium as the main carbon source.
33. The method according to embodiment 32, wherein the main carbon source provides at least 20%, 30%, 40%, 50%, 60%, 70%, 75%, 80%, 85%, 90%, 95%, 98%, 99% or 100% of all required carbon for the growth of the microorganism.
34. The method according to embodiment 32, wherein the monosaccharide is chosen from the group comprising glucose, fructose, galactose, mannose, ribose or arabinose.
35. The method according to embodiment 32, wherein the disaccharide is chosen from the group comprising maltose, sucrose, lactose, trehalose, cellobiose or chitobiose.
36. The method according to embodiment 32, wherein the oligosaccharide is chosen from the group comprising maltotriose, fructo-oligosaccharides, galacto-oligosaccharides, mannan oligosaccharides, isomaltooligosaccharide or glucooligosaccharides.
37. The method according to embodiment 32, wherein the polyol is chosen from the group comprising glycerol.
38. The method according to embodiment 32, wherein the complex medium is chosen from the group comprising molasses, corn steep liquor, peptone, tryptone or yeast extract.

In a preferred aspect, this disclosure relates to the following preferred specific embodiments:
1. A method for the production of a sialylated compound in a microorganism, the method comprising:
    culturing a microorganism in a culture medium, the culture medium optionally comprising an exogenous precursor,
    wherein the microorganism comprises at least one nucleic acid encoding a phosphatase, at least one nucleic acid encoding an N-acetyl-mannosamine epimerase; and at least one nucleic acid encoding a sialic acid synthase, and
    wherein the microorganism is unable to i) convert N-acetylglucosamine-6-P to glucosamine-6-P, ii) convert N-acetyl-glucosamine to N-acetyl-glucosamine-6-P, and iii) convert N-acetyl-neuraminate to N-acetyl-mannosamine; and
    modulating expression in the microorganism of a nucleic acid encoding a HAD-like phosphatase polypeptide, wherein the HAD-like phosphatase polypeptide comprises:
    at least one of the following motifs:
    Motif 1: hDxDx[TV] (SEQ ID NO: 73), or
    Motif 2: [GSTDE][DSEN]x(1-2)[hP] x(1-2) [DGTS] (SEQ ID NOs: 74, 75, 76, 77),
    wherein h means a hydrophobic amino acid (A, I, L, M, F, V, P, G) and x can be any distinct amino acid;
    or a homologue or derivative of any one of SEQ ID NOs: 43, 44, 45, 47, 48, 50, 51, 52, 54, 55 or 57 having at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to the polypeptide.
2. The method according to preferred embodiment 1, wherein the HAD-like polypeptide comprises any one of SEQ ID NOs: 43, 44, 45, 47, 48, 50, 51, 52, 54, 55, and 57.
3. Method according to preferred embodiment 1, wherein the modulated expression is effected by introducing and expressing in a microorganism a nucleic acid encoding a HAD-like polypeptide.
4. Method according to preferred embodiment 1, wherein the modulated expression is effected by the action of a constitutive promoter.
5. The method according to any one of the preceding preferred embodiments, wherein the sialylated compound is selected from the group consisting of N-acetylneuramic acid, sialylated oligosaccharide, sialylated lipids, sialylated protein, sialylated aglycon.
6. The method according to the previous preferred embodiment, wherein the sialylated compound is a sialylated oligosaccharide.
7. The method according to preferred embodiment 8, wherein the sialylated oligosaccharide is sialyllactose.
8. The method according to preferred embodiment 8, wherein the sialylated oligosaccharide is disialyl lacto-N-tetraose.
9. The method according to preferred embodiment 7, wherein the sialylated compound is N-acetyl-neuraminic acid.
10. The method according to any one of preferred embodiment 1 to 9 wherein the sialylated compound is a sialylated lacto-N-triose, lacto-N-tetraose or a lacto-N-neotetraose, and wherein the microorganism further comprises the activity of a galactosyltransferase (EC 2.4.1.38), preferably the galactosyltransferase originates from the group comprising *Homo sapiens, Bos taurus*, Mus mulatta, *Gallus gallus, Danio rerio, Helicobacter pylori* and *Haemophilus* ducrey; and/or the microorganism comprises the activity of a N-acetylglucosaminyltransferase (EC 2.4.1.90), preferably the N-acetylglucosaminyltransferase originates from the group comprising *Bos taurus, Homo sapiens* and *Mus musculus*.
11. The method according to preferred embodiment 12 wherein the microorganism is unable to express the genes coding for UDP sugar hydrolase and galactose-1-phosphate uridylyltransferase.
12. The method according to any one of preferred embodiments 1 to 13, wherein the microorganism produces less than 50%, 40%, 30%, 20%, 10%, 5%, 2% extracellular N-acetylglucosamine and/or N-acetylmannosamine than sialylated compound and/or the micro-organism produces equal or more than 50%, 60%, 70%, 80%, 90%, 95%, 98% sialylated compound on total carbohydrate.
13. A method for producing a sialylated oligosaccharide, comprising:
a) culturing a microorganism according to the method of any one of preferred embodiments 1 to 12, and wherein the microorganism produces internally, activated N-acetylneuraminate as donor substrate for a sialyltransferase; and
b) culturing the microorganism in a culture medium comprising an exogenous precursor selected from the group consisting of lactose, N-acetyllactosamine, lacto-N-biose, galactose, beta-galactoside, and alpha-galactoside such as but not limited to globotriose (Gal-alpha-1,4Gal-beta-1,4Glc)galactose, wherein active uptake into the microorganism of the exogenous precursor occurs and wherein the exogenous precursor is the acceptor substrate for the sialytransferase for producing the sialylated oligosaccharide.
14. The method according to preferred embodiment 1, wherein any one or more of the N-acetylmannosamine epimerase and sialic acid synthase is overexpressed in the microorganism.
15. The method according to preferred embodiment 1, wherein any one or more of the N-acetylmannosamine epimerase and sialic acid synthase is introduced and expressed in the microorganism.
16. The method according to preferred embodiment 1, wherein the microorganism lacks the genes encoding for following enzymes i) a N-acetylglycosamine-6-phosphate deacetylase, ii) a N-acetylglucosamine kinase, and iii) a N-acetylneuraminate aldolase.
17. The method according to preferred embodiment 1, wherein in the microorganism the genes encoding for following enzymes i) a N-acetylglycosamine-6-phosphate deacetylase, ii) a N-acetylglucosamine kinase, and iii) a N-acetylneuraminate aldolase are reduced in activity, preferably the genes are deleted or knocked-out.
18. The method according to any one of the preferred embodiments 1 to 17, wherein the microorganism further encodes a protein that facilitates uptake of lactose and lacks enzymes that metabolize lactose.
19. The method according to any one of preferred embodiments 1 to 18, wherein the microorganism is a bacterium, preferably an *Escherichia coli* strain, more preferably an *Escherichia coli* strain, which is a K12 strain, even more preferably the *Escherichia coli* K12 strain is *Escherichia coli* MG1655.
20. The method according to any one of preferred embodiments 1 to 18, wherein the microorganism is a yeast.
21. The method according to any one of preferred embodiments 1 to 20, wherein the exogenous precursor is chosen from the group comprising lactose, galactose, beta-galactoside, and alpha-galactoside, such as globotriose (Gal-alpha-1,4Gal-beta-1,4Glc).
22. Microorganism, obtainable by a method according to any one of preferred embodiments 1 to 21, wherein the microorganism comprises a recombinant nucleic acid encoding a HAD-like polypeptide.
23. A microorganism for the production of sialylated compounds wherein the microorganism comprises at least one nucleic acid encoding a phosphatase, at least one nucleic acid encoding an N-acetylmannosamine epimerase; and at least one nucleic acid encoding a sialic acid synthase, and wherein the microorganism is unable to i) convert N-acetylglucosamine-6-P to glucosamine-6-P, ii) convert N-acetyl-glucosamine to N-acetyl-glucosamine-6-P, and iii) convert N-acetyl-neuraminate to N-acetyl-mannosamine; characterized in that the microorganism comprises a modulated expression of a nucleic acid encoding a HAD-like phosphatase polypeptide as defined in preferred embodiment 1.
24. Construct comprising:
(i) nucleic acid encoding a HAD-like polypeptide as defined in preferred embodiment 1 or 2;

(ii) one or more control sequences capable of driving expression of the nucleic acid sequence of (i); and optionally;
(iii) a transcription termination sequence.

25. Construct according to preferred embodiment 24, wherein one of the control sequences is a constitutive promoter.

26. Use of a construct according to preferred embodiment 24 or 25 in a method for producing sialylated compounds.

27. A sialylated compound produced according to the method described in any one of preferred embodiments 1 to 21, wherein the sialylated compound is added to food formulation, feed formulation, pharmaceutical formulation, cosmetic formulation, or agrochemical formulation.

28. A microorganism for the production of a sialylated compound, the microorganism being defined in any one of embodiments 2 to 21.

29. A cell culture medium comprising lactose as precursor and the microorganism of any one of embodiments 22, 23 or 28.

30. The method according to one of embodiments 1 to 21, for the production of 3sialyllactose or 6sialyllactose, wherein the microorganism is cultivated at high cell density on a carbon substrate, such as glucose or glycerol or sucrose, and fed with lactose that is internalized by the lactose permease and sialylated by the recombinant sialyltransferase using the CMP-N-acetylneuraminate endogenously generated from N-acetylglucosamine.

31. The method according to any one of embodiments 1 to 21, wherein the sialylated compound is isolated from the culture medium by means of a unit operation selected from the group centrifugation, filtration, microfiltration, ultrafiltration, nanofiltration, ion exchange, electrodialysis, chromatography, simulated moving bed, evaporation, precipitation, crystallization, lyophilization and/or spray drying.

32. A sialylated compound produced according to the method described in any one of embodiments 1 to 21, wherein the sialylated compound is purified by centrifugation and/or filtration, ion-exchange, concentration through evaporation or nanofiltration, formulation through crystallization or spraydrying or lyophilization.

33. A sialylated compound produced according to the method described in any one of embodiments 1 to 21, wherein the sialylated compound is added to food formulation, feed formulation, pharmaceutical formulation, cosmetic formulation, or agrochemical formulation.

34. The method according to any one of embodiments 1 to 21, wherein the culture medium comprises any one or more of the following: a monosaccharide, disaccharide, oligosaccharide, polysaccharide, polyol, a complex medium as the main carbon source.

35. The method according to embodiment 34, wherein the main carbon source provides at least 20%, 30%, 40%, 50%, 60%, 70%, 75%, 80%, 85%, 90%, 95%, 98%, 99% or 100% of all required carbon for the growth of the microorganism.

36. The method according to embodiment 34, wherein the monosaccharide is chosen from the group comprising glucose, fructose, galactose, mannose, ribose or arabinose.

37. The method according to embodiment 34, wherein the disaccharide is chosen from the group comprising maltose, sucrose, lactose, trehalose, cellobiose or chitobiose.

38. The method according to embodiment 34, wherein the oligosaccharide is chosen from the group comprising maltotriose, fructo-oligosaccharides, galacto-oligosaccharides, mannan oligosaccharides, isomaltooligosaccharide or glucooligosaccharides.

39. The method according to embodiment 34, wherein the polyol is chosen from the group comprising glycerol.

40. The method according to embodiment 34, wherein the complex medium is chosen from the group comprising molasses, corn steep liquor, peptone, tryptone or yeast extract.

EXAMPLES

Example 1: Materials and Methods

Method and Materials *Escherichia coli*
Media

Three different media were used, namely a rich Luria Broth (LB), a minimal medium for shake flask (MMsf) and a minimal medium for fermentation (MMf). Both minimal media use a trace element mix.

Trace element mix consisted of 3.6 g/L $FeCl_2\cdot 4H_2O$, 5 g/L $CaCl_2\cdot 2H_2O$, 1.3 g/L $MnCl_2\cdot 2H_2O$, 0.38 g/L $CuCl_2\cdot 2H_2O$, 0.5 g/L $CoCl_2\cdot 6H_2O$, 0.94 g/L $ZnCl_2$, 0.0311 g/L $H_3BO_4$, 0.4 g/L $Na_2EDTA\cdot 2H_2O$ and 1.01 g/L thiamine.HCl. The molybdate solution contained 0.967 g/L $Na_2MoO_4\cdot 2H_2O$. The selenium solution contained 42 g/L $SeO_2$.

The Luria Broth (LB) medium consisted of 1% tryptone peptone (Difco, Erembodegem, Belgium), 0.5% yeast extract (Difco) and 0.5% sodium chloride (VWR, Leuven, Belgium).

Luria Broth agar (LBA) plates consisted of the LB media, with 12 g/L agar (Difco, Erembodegem, Belgium) added.

Minimal medium for shake flask experiments (MMsf) contained 2.00 g/L $NH_4Cl$, 5.00 g/L $(NH_4)_2SO_4$, 2.993 g/L $KH_2PO_4$, 7.315 g/L $K_2HPO_4$, 8.372 g/L MOPS, 0.5 g/L NaCl, 0.5 g/L $MgSO_4\cdot 7H_2O$. A carbon source chosen from, but not limited to glucose, fructose, maltose, glycerol and maltotriose, was used. The concentration was default 15 g/L, but this was subject to change depending on the experiment. 1 mL/L trace element mix, 100 µL/L molybdate solution, and 1 mL/L selenium solution. The medium was set to a pH of 7 with 1M KOH. Depending on the experiment lactose could be added as a precursor.

The minimal medium for fermentations contained 6.75 g/L $NH_4Cl$, 1.25 g/L $(NH_4)_2SO_4$, 1.15 g/L $KH_2PO_4$ (low phosphate medium) or 2.93 g/L $KH_2PO_4$ and 7.31 g/L $KH_2PO_4$ (high phosphate medium), 0.5 g/L NaCl, 0.5 g/L $MgSO_4\cdot 7H_2O$, a carbon source including but not limited to glucose, sucrose, fructose, maltose, glycerol and maltotriose, 1 mL/L trace element mix, 100 µL/L molybdate solution, and 1 mL/L selenium solution with the same composition as described above.

Complex medium, e.g., LB, was sterilized by autoclaving (121° C., 21) and minimal medium (MMsf and MMf) by filtration (0.22 µm Sartorius). If necessary the medium was made selective by adding an antibiotic (e.g., ampicillin (100 mg/L), chloramphenicol (20 mg/L), carbenicillin (100 mg/L), spectinomycin (40 mg/L) and/or kanamycin (50 mg/L)).

Strains

*Escherichia coli* MG1655 [lambda⁻, F⁻, rph-1] was obtained from Coli Genetic Stock Center (US), CGSC Strain #: 7740 in March 2007. Mutant strains were constructed using the homologous recombination, as described by Datsenko and Wanner (PNAS 97 (2000), 6640-6645).

Plasmids pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were obtained from Prof. R. Cunin (Vrije Universiteit Brussel, Belgium in 2007).

Plasmid pCX-CjneuB was constructed using Gibson assembly. The gene CjneuB1 was expressed using the expression vector as described by Aerts et. al (Eng. Life Sci. 2011, 11, No. 1, 10-19).

Plasmid pCX-CjneuB-NmneuA-Pdbst was constructed using Gibson assembly. The genes CjneuB1, NmneuA and Pdbst were expressed using the expression vector as described by Aerts et. al (Eng. Life Sci. 2011, 11, No. 1, 10-19).

Plasmids for phosphatase expression were constructed using Golden Gate assembly. The phosphatases (EcAphA, EcCof, EcHisB, EcOtsB, EcSurE, EcYaed, EcYcjU, EcYedP, EcYfbT, EcYidA, EcYigB, EcYihX, EcYniC, EcYqaB, EcYrbL and PsMupP) were expressed using promoters apFAB87 and apFAB346 and UTRs gene10_SD2-junction_HisHA and UTR1 AATTCGCCGGAGGGATAT-TAAAAtgaatggaaaattgAAACATCTTAATCATGCTAAG-GAGG TTTTCTAATG (SEQ ID NO: 41). All promoters and UTRs except UTR1 are described by Mutalik et. al (Nat. Methods 2013, No. 10, 354-360). Also phosphatases EcAppA, EcGph, EcSerB, EcNagD, EcYbhA, EcYbiV, EcYbjL, EcYfbR, EcYieH, EcYjgL, Ec YjjG, EcYrfG, EcYbiU, ScDOG1 and BsAraL are expressed using the same promoters and UTRs.

Plasmid pBR322-NmneuB was constructed using a pBR322 vector via Golden Gate assembly. The promoter and UTR used for the expression of NmNeuB are promoter apFAB299 and UTR galE_SD2-junction_BCD12. Plasmid pSC101-NmneuA-Pdbst was constructed using a pSC101 vector via Golden Gate assembly. The promoters and UTRs used for the expression of NmneuA are promoter apFAB37 and UTR galE_SD2-junction_BCD18. The promoters and UTRs used for the expression of Pdbst are promoter apFAB339 and UTR galE_SD2-junction_BCD12. All promoters and UTRs are described by Mutalik et. al (Nat. Methods 2013, No. 10, 354-360).

Plasmids were maintained in the host *E. coli* DH5alpha (F⁻, phi80dlacZdeltaM15, delta(lacZYA-argF) U169, deoR, recA1, endA1, hsdR17(rk⁻, mk⁺), phoA, supE44, lambda⁻, thi-1, gyrA96, relA1). Bought from Invitrogen.

Gene Disruptions

Gene disruptions as well as gene introductions were performed using the technique published by Datsenko and Wanner (PNAS 97 (2000), 6640-6645). This technique is based on antibiotic selection after homologous recombination performed by lambda Red recombinase. Subsequent catalysis of a flippase recombinase ensures removal of the antibiotic selection cassette in the final production strain.

In Table A the necessary primers for the construction of the gene disruption cassette are listed.

TABLE A

Lists of primers to construct disruption cassette for the target gene.

| Gene target | Fw primer | Rv primer |
| --- | --- | --- |
| lacZYA | GCTGAACTTGTAGGCCTGATAAGC GCAGCGTATCAGGCAATTTTTATA ATCTTCATTTAAATGGCGCGC (SEQ ID NO: 1) | GCGCAACGCAATTAATGTGAGTTAG CTCACTCATTAGGCACCCCAGGCTT CGCCTACCTGTGACGGAAG (SEQ ID NO: 2) |
| nagABCDE | CGCTTAAAGATGCCTAATCCGCCA ACGGCTTACATTTTACTTATTGAG GTGAATAGTGTAGGCTGGAGCTGC TTC (SEQ ID NO: 3) | GGCGTTTGTCATCAGAGCCAACCAC GTCCGCAGACGTGGTTGCTATCATA TGAATATCCTCCTTAG (SEQ ID NO: 4) |
| nanATEK | TAATGCGCCGCCAGTAAATCAACA TGAAATGCCGCTGGCTCCGTGTAG GCTGGAGCTGCTTC (SEQ ID NO: 5) | CCAACAACAAGCACTGGATAAAGC GAGTCTGCGTCGCCTGGTTCAGTTC ACATATGAATATCCTCCTTAG (SEQ ID NO: 6) |
| manXYZ | AAAATACATCTGGCACGTTGAGGT GTTAACGATAATAAAGGAGGTAG CAAGTGTAGGCTGGAGCTGCTTC (SEQ ID NO: 7) | CCTCCAGATAAAAAAACGGGGCCA AAAGGCCCCGGTAGTGTACAACAGT CCATATGAATATCCTCCTTAG (SEQ ID NO: 8) |

For the genomic integration of the necessary genes into the production hosts genome based on the same technique used for the gene disruption, discussed before, with specific alterations to the disruption cassette. Between a homology site and the FRT site of the disruption cassette, the to be integrated constructed is located. This allows for elegant integration of the constructed in the region dictated by the homology sites.

Using this workflow, a direct gene disruption and genomic integration is possible. Primers that were used for target integration are at specific sites are listed in Table B.

TABLE B

Primers used for genomic integration

| Integration location | Fw primer | Rv primer |
|---|---|---|
| nagABCDE | GTTTGGCGTTTGTCATCAGAGCC AACCACGTCCGCAGACGTGGTTG CTATGTGTAGGCTGGAGCTGCTT C (SEQ ID NO: 9) | TTGTCATTGTTGGATGCGACGCTC AAGCGTCGCATCAGGCATAAAGC AGACTTAAGCGACTTCATTCACC (SEQ ID NO: 10) |
| nanATEK | CATGGCGGTAATGCGCCGCCAGT AAATCAACATGAAATGCCGCTGG CTCCGTGTAGGCTGGAGCTGCTT C (SEQ ID NO: 11) | CCAACAACAAGCACTGGATAAAG CGAGTCTGCGTCGCCTGGTTCAGT TCACTTAAGCGACTTCATTCACC (SEQ ID NO: 12) |
| manXYZ | AAAATACATCTGGCACGTTGAGG TGTTAACGATAATAAAGGAGGTA GCAAGTGTAGGCTGGAGCTGCTT C (SEQ ID NO: 13) | CCTCCAGATAAAAAAACGGGGCC AAAAGGCCCCGGTAGTGTACAAC AGTCCTTAAGCGACTTCATTCACC (SEQ ID NO: 14) |
| lacZYA | GCGCAACGCAATTAATGTGAGTT AGCTCACTCATTAGGCACCCCAG GCTTGTGTAGGCTGGAGCTGCTT C (SEQ ID NO: 15) | GCTGAACTTGTAGGCCTGATAAGC GCAGCGTATCAGGCAATTTTTATA ATCTTAAGCGACTTCATTCACC (SEQ ID NO: 16) |
| atpI-gidB | CAAAAAGCGGTCAAATTATACGG TGCGCCCCGTGATTTCAAACAA TAAGGTGTAGGCTGGAGCTGCTT C (SEQ ID NO: 17) | ATAACGTGGCTTTTTTTGGTAAGC AGAAAATAAGTCATTAGTGAAAA TATCTTAAGCGACTTCATTCACC (SEQ ID NO: 18) |

Clones carrying the temperature sensitive pKD46 helper plasmid were grown in mL LB media with ampicillin (100 mg/L) and L-arabinose (10 mM) at 30° C. to an $OD_{600nm}$ of The cells were made electro competent by sequential washing, once with 50 mL, and once with 1 mL ice-cold deionized water. Next, the cells were resuspended in 50 μL of ice-cold water. Finally, 10-100 ng of disruption/integration cassette was added to 50 μL of the washed cell solution for electroporation. Electroporation was performed using a Gene Pulser (trademark of BioRad) (600 Ohm 25 μFD, and 250 V).

After electroporation, cells were resuscitated in 1 mL LB media for 1 h at 37° C., and finally plated out onto LB-agar containing 25 mg/L of chloramphenicol or 50 mg/L of kanamycin to select antibiotic resistant transformants. The selected mutants were verified by PCR with primers upstream and downstream of the modified region and were subsequently grown on LB-agar at 42° C. for the loss of the pKD46 helper plasmid. The mutants were finally tested for ampicillin sensitivity.

The selected mutants (chloramphenicol or kanamycin resistant) were transformed with pCP20 plasmid, which is an ampicillin and chloramphenicol resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistances and thus also of the FLP helper plasmid. The gene disruptions and/or gene integration are checked with control primers and sequenced. These primers are listed in Table C.

TABLE C

Primers to validate either gene disruption and/or genomic integration for specific gene targets.

| Gene targets | Fw primer | Rv primer |
|---|---|---|
| lacZYA | CAGGTTTCCCGACTGGAAAG (SEQ ID NO: 19) | TGTGCGTCGTTGGGCTGATG (SEQ ID NO: 20) |
| nagABCDE | CGCTTGTCATTGTTGGATGC (SEQ ID NO: 21) | GCTGACAAAGTGCGATTTGTTC (SEQ ID NO: 22) |
| nanATEK | GTCGCCCTGTAATTCGTAAC (SEQ ID NO: 23) | CTTTCGGTCAGACCACCAAC (SEQ ID NO: 24) |
| manXYZ | ACGCCTCTGATTTGGCAAAG (SEQ ID NO: 25) | AGCCAGTGCGCTTAATAACC (SEQ ID NO: 26) |
| atpI-gidB | GCTGAACAGCAATCCACTTG (SEQ ID NO: 27) | TGAACGATATGGTGAGCTGG (SEQ ID NO: 28) |

Heterologous and Homologous Expression

Genes that needed to be expressed, be it from a plasmid or from the genome were synthetically synthetized with one of the following companies: DNA2.0, Gen9 or IDT.

*Escherichia coli* native genes, as e.g., phosphatases, were picked from the *E. coli* K-12 MG1655 genome. The origin of other genes are indicated in the relevant table.

Expression could be further facilitated by optimizing the codon usage to the codon usage of the expression host. Gene were optimized using the tools of the supplier.

Cultivation Conditions

A preculture of 96well microtiter plate experiments was started from single colony on a LB plate, in 175 µL and was incubated for 8h at 37° C. on an orbital shaker at 800 rpm. This culture was used as inoculum for a 96well microtiter plate, with 175 µL MMsf medium by diluting 300×. These cultures in turn, were used as a preculture for the final experiment in a 96well plate, again by diluting 300×. The 96well plate can either be microtiter plate, with a culture volume of 175 µL or a 24well deepwell plate with a culture volume of 3 mL.

A preculture for shake flask experiments was started from a single colony on a LB-plate, in 5 mL LB medium and was incubated for 8 h at 37° C. on an orbital shaker at 200 rpm. From this culture, 1 mL was transferred to 100 mL minimal medium (MMsf) in a 500 mL shake flask and incubated at 37° C. on an orbital shaker at 200 rpm. This setup is used for shake flask experiments.

A shake flask experiment grown for 16h could also be used as an inoculum for a bioreactor. 4% of this cell solution was to inoculate a 2 L Biostat Dcu-B with a 4 L working volume, controlled by MFCS control software (Sartorius Stedim Biotech, Melsungen, Germany). Culturing condition were set to 37° C., 800 rpm stirring, and a gas flow rate of 1.5 L/min. The pH was controlled at 7 using 0.5 M H2S04 and 25% NH4OH. The exhaust gas was cooled. 10% solution of silicone antifoaming agent was added when foaming raised during the fermentation (approximately 10 6 L). The use of an inducer is not required as all genes are constitutively expressed.

Material and Methods *Saccharomyces cerevisae*

Media

Strains are grown on Synthetic Defined yeast medium with Complete Supplement Mixture (SD CSM) or CSM drop-out (SD CSM-Ura) containing 6.7 g/L Yeast Nitrogen Base without amino acids (YNB w/o AA, Difco), 20 g/L agar (Difco) (solid cultures), 22 g/L glucose monohydrate or 20 g/L lactose and 0.79 g/L CSM or 0.77 g/L CSM-Ura (MP Biomedicals).

Strains

*Saccharomyces cerevisiae* BY4742 created by Bachmann et al. (Yeast (1998) 14:115-32) was used available in the Euroscarf culture collection. All mutant strains were created by homologous recombination or plasmid transformation using the method of Gietz (Yeast 11:355-360, 1995). *Kluyveromyces marxianus lactis* is available at the LMG culture collection (Ghent, Belgium).

Plasmids

Yeast expression plasmid p2a_2µ_sia_GFA1 (Chan 2013 (Plasmid 70 (2013) 2-17)) was used for expression of foreign genes in *Saccharomyces cerevisae*. This plasmid contains an ampicillin resistance gene and a bacterial origin of replication to allow for selection and maintenance in *E. coli*. The plasmid further contains the 2µ yeast ori and the Ura3 selection marker for selection and maintenance in yeast. Finally, the plasmid can contain a beta-galactosidase expression cassette. Next, this plasmid also contains a N-acetylglucosamine-2-epimerase (for example from *Bacteroides ovatus* (BoAGE)) and a sialic acid synthase (for example from *Campylobacter jejuni* (CjneuB)). Finally, it also contains the fructose-6-P-aminotransferase from *Saccharomyces cerevisiae*, ScGFA1.

Yeast expression plasmid p2a_2µ_sia_glmS is based on p2a_2µ_sia but modified in a way that also glmS*54 (fructose-6-P-aminotransferase from *Escherichia coli*) is expressed.

Yeast expression plasmids p2a_2µ_sia_glmS_phospha is based on p2a_2µ_sia_glmS but modified in a way that also EcAphA (SEQ ID NO: 42), EcCof (SEQ ID NO: 43), EcHisB (SEQ ID NO: 44), EcOtsB (SEQ ID NO: 45), EcSurE (SEQ ID NO: 46), EcYaed (SEQ ID NO: 47), EcYcjU (SEQ ID NO: 48), EcYedP (SEQ ID NO: 49), EcYfbT (SEQ ID NO: 50), EcYidA (SEQ ID NO: 51), EcYigB (SEQ ID NO: 52), EcYihX (SEQ ID NO: 53), EcYniC (SEQ ID NO: 54), EcYqaB (SEQ ID NO: 55), EcYrbL (SEQ ID NO: 56), PsMupP (SEQ ID NO: 57), EcAppA (SEQ ID NO: 58), EcGph (SEQ ID NO: 59), EcSerB (SEQ ID NO: 60), EcNagD (SEQ ID NO: 61), EcYbhA (SEQ ID NO: 62), EcYbiV (SEQ ID NO: 63), EcYbjL (SEQ ID NO: 64), EcYfbR (SEQ ID NO: 65), EcYieH (SEQ ID NO: 66), EcYjgL (SEQ ID NO: 67), Ec YjjG (SEQ ID NO: 68), EcYrfG (SEQ ID NO: 69), EcYbiU (SEQ ID NO: 70), ScDOG1 (SEQ ID NO: 71) and BsAraL (SEQ ID NO: 72) are expressed.

Yeast expression plasmid p2a_2µ_SL-glmS is based on p2a_2µ_sia but modified in a way that also K1LAC 12 (lactose permease from *Kluyveromyces lactis*), NmneuA (CMP-sialic acid synthase from *Neisseria meningitides*) and Pdbst (sialyltransferase *Photobacterium damselae*) are expressed.

Plasmids were maintained in the host *E. coli* DH5alpha (F⁻, phi80dlacZdeltaM15, delta(lacZYA-argF)U169, deoR, recA1, endA1, hsdR17(rk⁻, mk⁺), phoA, supE44, lambda⁻, thi-1, gyrA96, relA1). Bought from Invitrogen.

Gene Expression Promoters

Genes are expressed using synthetic constitutive promoters, as described in by Blazeck (Biotechnology and Bioengineering, Vol. 109, No. 11, 2012).

Heterologous and Homologous Expression

Genes that needed to be expressed, be it from a plasmid or from the genome were synthetically synthetized with one of the following companies: DNA2.0, Gen9 or IDT.

Expression could be further facilitated by optimizing the codon usage to the codon usage of the expression host. Gene were optimized using the tools of the supplier.

Cultivations Conditions

In general, yeast strains were initially grown on SD CSM plates to obtain single colonies. These plates were grown for 2-3 days at 30° C.

Starting from a single colony, a preculture was grown over night in 5 mL at 30° C., shaking at 200 rpm. Subsequent 500 mL shake flask experiments were inoculated with 2% of this preculture, in 100 mL media. These shake flasks were incubated at 30° C. with an orbital shaking of 200 rpm. The use of an inducer is not required as all genes are constitutively expressed.

Material and Methods *Bacillus subtilis*

Media

Two different media are used, namely a rich Luria Broth (LB), a minimal medium for shake flask (MMsf). The minimal medium uses a trace element mix.

Trace element mix consisted of 0.735 g/L CaCl2·2H20, 0.1 g/L MnCl2·2H20, g/L CuCl2·2H20, 0.06 g/L CoCl2·6H20, 0.17 g/L ZnCl2, XX g/L H3B04, XX g/L Na2EDTA·2H20 and 0.06 g/L Na2Mo04. The Fe-citrate solution contained 0.135 g/L FeCl3·6H20, 1 g/L Na-Citrate (Hoch 1973 PMC1212887).

The Luria Broth (LB) medium consisted of 1% tryptone peptone (Difco, Erembodegem, Belgium), 0.5% yeast extract (Difco) and 0.5% sodium chloride (VWR, Leuven, Belgium).

Luria Broth agar (LBA) plates consisted of the LB media, with 12 g/L agar (Difco, Erembodegem, Belgium) added.

Minimal medium for shake flask experiments (MMsf) contains 2 g/L (NH4)2S04, 7.5 g/L KH2P04, 17.5 g/L K2HP04, 1.25 g/L Na-Citrate, 0.25 g/L MgS04·7H20, tryptophan, from 10 up to 30 g/L glucose or another carbon source including but not limited to glucose, fructose, maltose, glycerol and maltotriose, 10 mL/L trace element mix, and mL/L Fe-citrate solution. The medium was set to a pH of 7 with 1M KOH.

Complex medium, e.g., LB, was sterilized by autoclaving (121° C., 21) and minimal medium (MMsf) by filtration (0.22 μm Sartorius). If necessary, the medium was made selective by adding an antibiotic (e.g., ZEOCIN™ (20 mg/L)).

Strains

*Bacillus subtilis* 168, available at *Bacillus* Genetic Stock Center (Ohio, USA).

Plasmids and Gene Overexpression

Plasmids for gene deletion via Cre/lox are constructed as described by Yan et al. (Appl & environm microbial, sept 2008, p5556-5562).

Expression vectors can be found at Mobitec (Germany), or at ATCC (ATCC® number 87056). The genes BsglmS, ScGNA1 and CjneuB are cloned in these expression vectors. A suitable promoter for expression can be derived from the part repository (iGem): sequence id: BBa_K143012, BBa_K823000, BBa_K823002 or BBa_K823003. Cloning can be performed using Gibson Assembly, Golden Gate assembly, Cliva assembly, LCR or restriction ligation.

Plasmids are maintained in the host *E. coli* DH5alpha (F⁻, phi 80dlacZdeltaM15, delta(lacZYA-argF)U169, deoR, recA 1, endA1, hsdR17(rk⁻, mk⁺), phoA, supE44, lambda⁻, thi-1, gyrA96, relA1). Bought from Invitrogen.

Gene Disruptions

Disrupting of genes is done via homologous recombination with linear DNA and transformation via the electroporation as described by Xue et al. (*J. microb. Meth.* 34 (1999) 183-191). The method of gene knock-outs is described by Liu et al. (*Metab. Engine.* 24 (2014) 61-69). This method uses 1000 bp homologies up- and downstream of the target gene. The homologies to be used in this disclosure, are listed in table D. After the modification, the mutants are verified using primers upstream and downstream of the modified region. These primers are given in table E. Next, the modification is confirmed by sequencing (performed at LGC Genomics (LGC group, Germany)).

TABLE D

| Gene to be disrupted | Upstream homology | Downstream homology |
|---|---|---|
| nagA-nagB | Gactgcaagatttcggcctgggcggacggg aatcgtcagttttgtaatttctgtatcaat gattttcatggtctcttcctcaagtccgag ccggtcgtattgcttgcctgctcccagag ttcaagattcatgacaatcgtgattcgttt attgcttctgaccgcgccagcgccaaatag cgtcatcacattgataatgccaaggcccct gatctcaagaaggtgctcaattaattccgg agcgtttcccacaagagtatcctgatcctc ctgccgtatttcaacgcaatcatcggcaac aaggcgatgccctcttttcacaagctctag cgctgtttcgcttttccgacgccgctttt tcctgtgatcagcacgccgacaccatatat atcgacaagaacgccatgaattgctgtggt aggcgcagcctgctctcaaggaagttggt taaacggcttgacagtcttgtcgttttcag cggcgatctgaggacaggcaccccatttt ctcggaggcgtcaatcagctcctgcgggat gggcatatctctagaaagaataatagctgg tgttacatcagtgcacagagaatccattcg ctgcttttctcctcttcaggaagctgttc aaagaaagaaagctctgtttttccgagaag ctgcacgcgctccctcgggtaatatgtaaa atatccggcaatttcaatacctggtcttga taggtcactcattgtaatcgggcggttaat tccttcttctccgctgattaattccaaatt gaactgttccattacgtcttttgtgcgaac ctttgccacgatatgttcctcctgttccgg gctgccccgagcttgctcacaatactttca ttttatcacttcgggcttgaacctaaaac agatttataaaaggggggaaaacacctca gctggtctagatcactagtctgaaaaagag taaaataaaggtattcaaattccagaaagg cggatcatct (SEQ ID NO: 33) | Aaggaacatgctgacttatgaatatcaata aacaatcgcctattccgatttactatcaga ttatggagcaattaaaaacccaaattaaga acggagagctgcagccggatatgcctcttc cttctgagcgcgaatatgccgaacaattcg ggatcagccggatgacagttcgccaggcgc tttctaatttagttaatgaaggcttgctct atcgcctgaaagggcggggcacctttgtca gcaagccaaaaatggaacaagcacttcaag ggctgacaagctttaccgaggatatgaaaa gccgcgggatgacaccgggcagcaggctca ttgattatcagcttattgattcaactgagg agctcgcggctatattaggctgcgggcacc cctcctctatccataaaatcactcgggtgc ggctggcaaatgatattccgatggcgattg agtcctcacatattccgtttgagcttgcgg gtgaattgaacgaatcgcattttcagtcgt cgatctatgatcatattgaaaggtacaaca gcataccgatttcccgtgcaaaacaggagc ttgagccaagcgctgccaccacggaagaag cgaatattcttggtattcaaaagggagcgc ctgtcctattaattaaacgaacaacatatc tgcagaacggaactgcttttgagcatgcaa aatccgtatacagaggcgaccgttatacat ttgtccactatatggatcgtctttcataaa aaaagcctccaacccttttttaaggattgga gacatggcgaaaatcaaactggtctggtgc cggacgatatgtttctttttttcgtcttgaa cttccagatcggtgatttcgttttgccgtt aaaactgtcttccactataatgtaccaata ataaacagactgcggttcaagatgatccca gcggaattcagctgtgtccccgctcttcac ttgctcccgttttccgagctcttcattggt atatacgtta (SEQ ID NO: 34) |
| gamA | Tggcggacatggaataaatcacaaacgaca aagatgacgccggcaagaatagagttaatc aaatagagcacgggcgcaacgaacaagaaa gaaaactcaaccggttctgtaattccggtc agcatagatgtgagcgccgcagaaatcatc acgccggagatcatttttttcttttccgga cgcgcggtatggataatggcaagagcaacg | Gtgacaccccctcaaagagatagacaagca ccatatttgttatgaccaatttatgatact tgtcattacgaatttagcaccgcccttatc aaactgtcaatattaatttctgaaaatttg ttataaaagaaggatacaaatctttcatat tgggagggcaaatggtattatggtctcaat gaaaaagaacggattgcatacagaatgggg |

TABLE D-continued

| Gene to be disrupted | Upstream homology | Downstream homology |
|---|---|---|
| | gccggcagacagaaaatcatgtaagggaaa<br>tcccccatcataaagcgcccggctgtcggg<br>tctcccgcgaaaaaccttgtcaggtcgccg<br>gttacggtgttgcctgttgatgggtctgtg<br>tattctcccatcataaaatagaaaggcgta<br>taaaaaatatgatgcaggccaaaaggaatc<br>agcaaacgatagatcgttgcataaaagaac<br>aggccgactgttgaatcggcaattaaactg<br>ctggctgcgttaattccgttttggatcagc<br>ggccaaacgaatgagaaaatgacgccgatc<br>accaatgaactgacggaagtaatgatcggg<br>acaaagcgttttccagagaaaaatccaagg<br>accggatgcagctcgattgatgaaaatcgc<br>ttatataaataggcggcgagaagcccgata<br>atgattcctccgaaaaccccccatatcaatc<br>aggtgctcggctccttcatacggaggctga<br>aggccgagtaattttcccatattgtcgagg<br>gtgacggttaaaattaagtatccgatgaca<br>gcggcaagtccggctacaccttctccgccg<br>gctaatccgatcgcgaccccacggcgaaa<br>atcagcggaaggttatcgaatacaacgccg<br>cccgcatcctttataatagggatgttcagt<br>aaatccttgtctccgaaacgggagcaaaaga<br>cctgctgccggcaggacggcaaccggagtc<br>atcaacgcgcggccaagctgctgcagaatt<br>tgaaatgccttttttaaacatgacagtctcc<br>ttttattgtg (SEQ ID NO: 35) | agaatgaaatgacagctttatattctgtta<br>tcaagtttaaaatcattgagttaattaaat<br>cgggcaaatatcaggcgaatgatcagctgc<br>cgacggagagtgagttttgcgaacaatatg<br>atgtcagcagaacaactgtgagactggctc<br>tgcagcagctagagcttgagggatatatta<br>aaagaattcaaggaaaagggacatttgtat<br>cggcggccaaaatacaaacgccgattccgc<br>ataagattacgagctttgcagaacaaatga<br>gaggacttcgttctgaatcaaaagtgcttg<br>agcttgtggtgattcctgccgatcattcca<br>tcgccgagcttttgaaaatgaaagagaatg<br>aacctgtcaacaagcttgtcagagtcagat<br>acgccgagggggaaccttttgcagtatcata<br>cctcatatattccctggaaggcggcaccgg<br>ggctggcgcaggaggaatgcaccggctcgc<br>tgtttgaattgttaaggacaaaatacaata<br>ttgaaatcgacaggggcacggaatcgatcg<br>aaccgattttaacggatgaaacgatcagcg<br>gacacttattaaccaatgtcggagcgcctg<br>cgttttttatcagaatcccttacctatgata<br>aaaatgaagaagtggtggaatatgcgcaaa<br>ttattacacggggagaccgaacgaaattca<br>ccgtagaacagtcatatcattcataaagca<br>atgtgttttaagaagggaatggtggttcta<br>tgttttttatttacgaatggaaaagtgctgt<br>ggggagcagt (SEQ ID NO: 36) |

TABLE E

| Target gene | Fw primer | Rv primer |
|---|---|---|
| nagA-nagB | Tgtaatcgggcggttaattc (SEQ ID NO: 37) | Gcccttttcaggcgatagag (SEQ ID NO: 38) |
| gamA | Acggcgaaaatcagcggaag (SEQ ID NO: 39) | Tcactctccgtcggcagctg (SEQ ID NO: 40) |

Heterologous and Homologous Expression

Genes that needed to be expressed, be it from a plasmid or from the genome were synthetically synthetized with one of the following companies: DNA2.0, Gen9 or IDT.

Expression could be further facilitated by optimizing the codon usage to the codon usage of the expression host. Gene were optimized using the tools of the supplier.

Cultivations Conditions

A preculture, from a single colony on a LB-plate, in 5 mL LB medium was incubated for 8 h at 37° C. on an orbital shaker at 200 rpm. From this culture, 1 mL was transferred to 100 mL minimal medium (MMsf) in a 500 mL shake flask and incubated at 37° C. on an orbital shaker at 200 rpm. This setup is used for shake flask experiments. The use of an inducer is not required as all genes are constitutively expressed.

Analytical Methods

Optical Density

Cell density of the culture was frequently monitored by measuring optical density at 600 nm (Implen Nanophotometer NP80, Westburg, Belgium). Cell dry weight was obtained by centrifugation (10 min, 5000 g, Legend X1R Thermo Scientific, Belgium) of 20 g reactor broth in pre-dried and weighted falcons. The pellets were subsequently washed once with 20 mL physiological solution (9 g/L NaCl) and dried at 70° C. to a constant weight. To be able to convert $OD_{600\ nm}$ measurements to biomass concentrations, a correlation curve of the $OD_{600nm}$ to the biomass concentration was made.

Measurement of Cell Dry Weight

From a broth sample, 4×10 g was transferred to centrifuge tubes, the cells were spun down (5000 g, 4° C., 5 min), and the cells were washed twice with 0.9% NaCl solution. The centrifuge tubes containing the cell pellets were dried in an oven at 70° C. for 48 h until constant weight. The cell dry weight was obtained gravimetrically; the tubes were cooled in a desiccator prior to weighing.

Liquid Chromatography

The concentration of carbohydrates like, but not limited to, glucose, fructose and lactose were determined with a Waters Acquity UPLC H-class system with an ELSD detector, using a Acquity UPLC BEH amide, 130 Å, 1.7 µm, 2.1 mm×50 mm heated at 35° C., using a 75/25 acetonitrile/water solution with 0.2% triethylamine (0.130 mL/min) as mobile phase.

Sialyllactose was quantified on the same machine, with the same column. The eluent however was modified to 75/25 acetonitrile/water solution with 1% formic acid. The flow rate was set to 0.130 mL/min and the column temperature to 35° C.

Sialic acid was quantified on the same machine, using the REZEX ROA column (300×7.8 mm ID). The eluent is 0.08% acetic acid in water. The flow rate was set to 0.5 mL/min and the column temperature to 65° C. GlcNAc and ManNAc were also measured using this method.

Growth Rate Measurement

The maximal growth rate (µMax) was calculated based on the observed optical densities at 600 nm using the R package grofit.

Example 2: Production of Sialic Acid in *Escherichia coli*

Figure 1B:
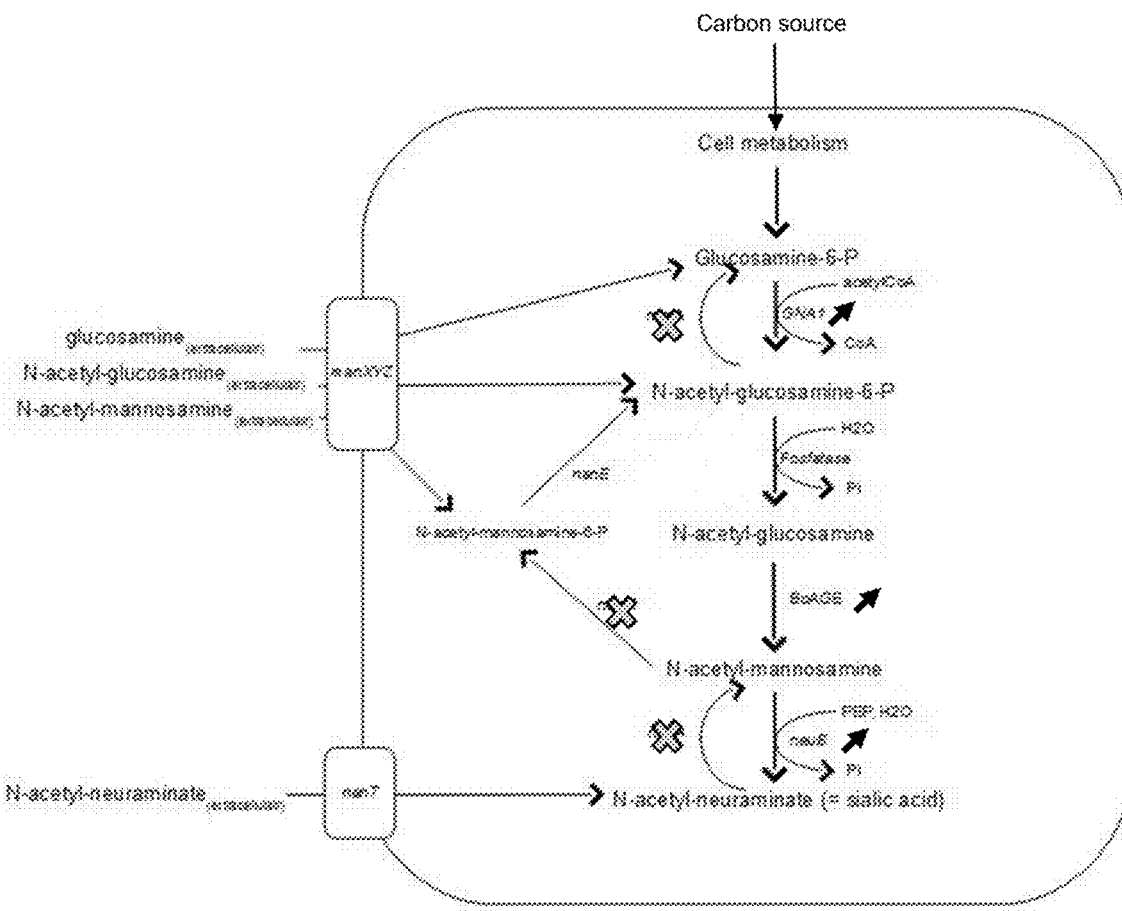
FIG. 1B shows the pathway as used in example 2 with the knock-out indicated with a cross and overexpression with an upgoing arrow next to the indicated enzyme.

A first example provides an *Escherichia coli* strain capable of producing N-acetyl-neuraminate (sialic acid) (see FIG. 1B).

A strain capable of accumulating glucosamine-6-phosphate using sucrose as a carbon source was further engineered to allow for N-acetylneuraminate production. The base strain overexpresses a sucrose phosphorylase from *Bifidobacterium adolescentis* (BaSP), a fructokinase from *Zymomonas mobilis* (Zmfrk), a mutant fructose-6-P-aminotransferase (EcglmS*54, as described by Deng et al. (Biochimie 88, 419-429 (2006))). To allow for gene sialic acid production the operons nagABCDE, nanATEK and manXYZ were disrupted. BaSP and Zmfrk were introduced at the location of nagABCDE and EcglmS*54 was introduced at the location of nanATEK. These modifications were done as described in example 1 and are based on the principle of Datsenko & Wanner (PNAS USA 97, 6640-6645 (2000)).

In this strain, the biosynthetic pathway for producing sialic acid as described in this disclosure, was implemented by overexpressing a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Campylobacter jejuni* (CjneuB). ScGNA1 and BoAGE were expressed on locations nagABCDE and manXYZ, respectively. CjneuB was expressed using the high copy plasmid pCX-CjneuB.

Figure 2:
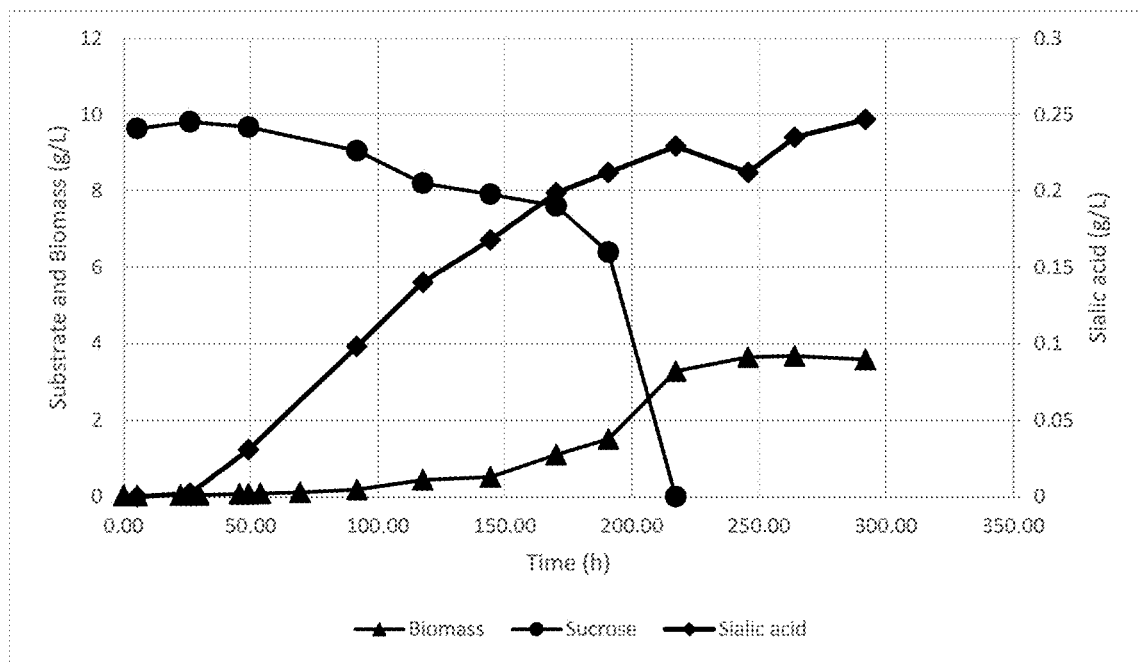
FIG. 2 shows the production results of the *Escherichia coli* strain capable of producing sialic acid as described in example 2.
Figure 3:
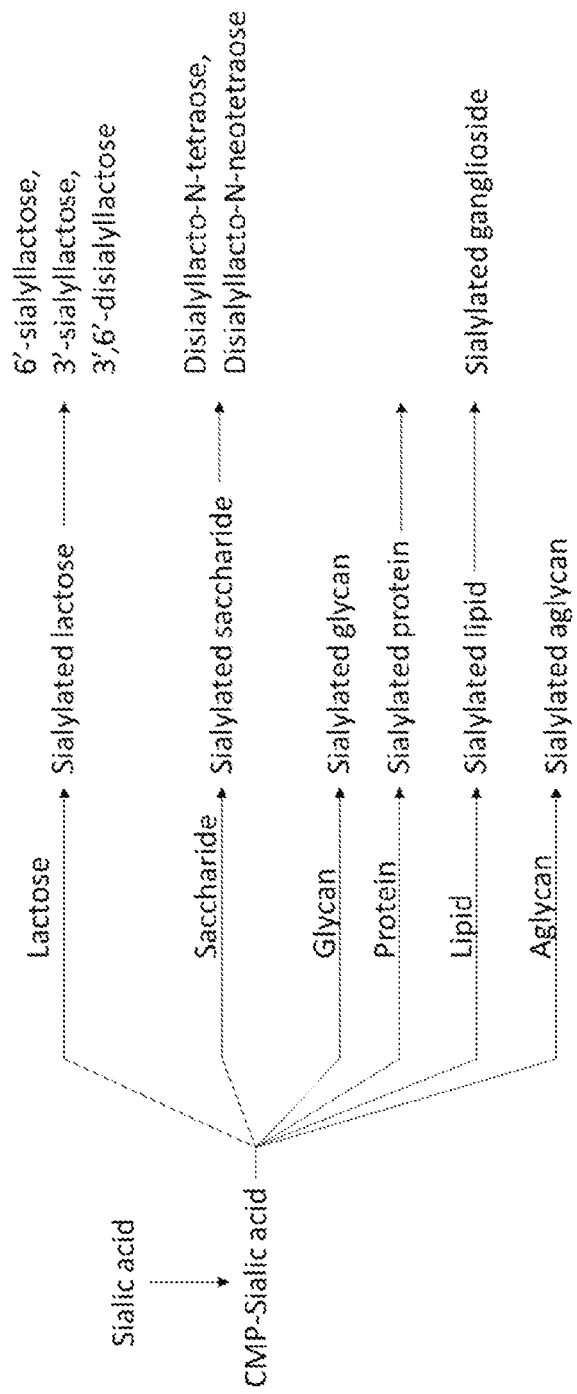
FIG. 3 shows examples of different sialylated compounds, which can be produced in the method of this disclosure.

The strain was cultured as described in example 1 (materials and methods). Briefly, a 5 mL LB preculture was inoculated and grown overnight at 37° C. This culture was used as inoculum in a shake flask experiment with 100 mL medium that contains 10 g/L sucrose and was made as described in example 1. Regular samples were taken and analyzed as described in example 1. The evolutions of the concentrations of biomass, sucrose and sialic acid are easily followed and an end concentration of 0.22 g/L N-acetylneuraminate was produced extracellularly, as can be seen in FIG. 2.

The same organism also produces N-acetylneuraminate based on glucose, maltose or glycerol as carbon source.

Example 3: Production of 6-Sialyllactose in *Escherichia coli*

Another example according to this disclosure is the use of the method and strains for the production of 6-sialyllactose.

The strain of example 3 is a daughter strain of the strain used in example 2. The strain is further modified by overexpressing a lactose permease EclacY from *Escherichia coli* (as described and demonstrated in example 1 of WO 2016/075243, which is here also incorporated by reference), a CMP-sialic acid synthethase from *Neisseria meningitides* (NmneuA) and a sialyltransferase from *Photobacterium damselae* (Pdbst). On top of that lacZ is disrupted.

The genes NmneuA and Pdbst are expressed from a plasmid, together with CjneuB. This plasmid is pCX-CjneuB-NmneuA-Pdbst, and is made as described in example 1.

The strain is inoculated as a preculture consisting of 5ml LB medium as described in example 1. After growing overnight at 37° C. in an incubator. 1% of this preculture is inoculated in a shake flask containing 100ml medium (MMsf) containing 10 g/l sucrose as carbon source and 10 g/l lactose as precursor. The strain is grown for 300h at 37° C.

This strain produces quantities of 6-sialyllactose.

Example 4: Production of Sialic Acid in *Saccharomyces cerevisiae* Using Heterologous Fructose-6-P-Aminotransferase Another example provides use of a eukaryotic organism, in the form of *Saccharomyces cerevisae*, for this disclosure. This method utilizing the pathway of this disclosure shall be obtained in *Saccharomyces cerevisiae* by introducing and expressing a N-acetylglucosamine-2-epimerase (for example from *Bacteroides ovatus* (BoAGE)) and a sialic acid synthase (for example from *Campylobacter jejuni* (CjneuB)).

As starting point, a strain with increased metabolic flux toward N-acetylglucosamine-6-phosphate is needed. This is achieved by overexpressing the fructose-6-P-aminotransferase mutant from *Escherichia coli* (EcglmS*54).

To create a N-acetylneuraminate producing *Saccharomyces cerevisiae* according to this disclosure, the genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmid used in this embodiment is p2a_2µ_sia_glmS. This plasmid is introduced into *Saccharomyces cerevisae* using the transformation technique described by Gietz and Woods (2002, PMID 12073338) and a mutant strain is obtained.

The strain is capable of converting fructose-6-phosphate into glucosamine-6-phosphate, followed by glucosamine-6-phosphate conversion in N-acetylglucosamine-6-phosphate. This N-acetylglucosamine-6-phosphate moiety is further converted to N-acetylglucosamine, the N-acetylglucosamine into N-acetylmannosamine and finally this N-acetyl-mannosamine is converted into N-acetyl-neuraminate.

A preculture of the strain is made in 5 mL of the synthetic defined medium SD-CSM containing 22 g/L glucose and grown at 30° C. as described in example 1. This preculture is inoculated in 100 mL medium in a shakeflask with 10 g/L sucrose as sole carbon source and grown at 30° C. Regular samples are taken and the production of N-acetylneuraminate is measured as described in example 1. This strain and method produces quantities of N-acetyl-neuraminate.

The same organism also produces N-acetylneuraminate based on glucose, maltose or glycerol as carbon source.

Example 5: Production of 6-Sialyllactose in *Saccharomyces cerevisiae*

Another example provides use of a eukaryotic organism, in the form of *Saccharomyces cerevisae*, for this disclosure. This method utilizing the pathway of this disclosure shall be obtained in *Saccharomyces cerevisiae* by introducing and expressing a N-acetylglucosamine-2-epimerase (for example from *Bacteroides ovatus* (BoAGE)) and a sialic acid synthase (for example from *Campylobacter jejuni* (CjneuB)).

On top of that, further modifications are made in order to produce 6sialyllactose. These modifications comprise the addition of a lactose permease, a CMP-sialic acid synthase and a sialyltransferase. The preferred lactose permease is the KILAC12 gene from *Kluyveromyces lactis* (WO 2016/075243). The preferred CMP-sialic acid synthase and the sialyltransferase are respectively NmneuA from *Neisseria meningitides* and Pdbst from *Photobacterium damselae*, as also described in example 3.

As starting point, a strain with increased metabolic flux toward N-acetylglucosamine-6-phosphate is needed. This is achieved by overexpressing the fructose-6-P-aminotransferase mutant from *Escherichia coli* (EcglmS*54).

To create a N-acetylneuraminate producing *Saccharomyces cerevisiae* according to this disclosure, the genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmid used in this embodiment is p2a_2μ_sia_glmS. This plasmid is introduced into *Saccharomyces cerevisae* using the transformation technique described by Gietz and Woods (2002) and a mutant strain is obtained.

The strain is capable of converting fructose-6-phosphate into glucosamine-6-phosphate, the glucosamine-6-phosphate into N-acetylglucosamine-6-phosphate, the N-acetylglucosamine-6-phosphate into N-acetylglucosamine, the N-acetylglucosamine into N-acetyl-mannosamine and finally the N-acetylmannosamine into N-acetylneuraminate. The N-acetyl-mannosamine is then converted to CMP-sialic acid and transferred to lactose to obtain 6sialyllactose.

A preculture of the strain is made in 5 mL of the synthetic defined medium SD-CSM containing 22 g/L glucose and grown at 30° C. as described in example 1. This preculture is inoculated in 100 mL medium in a shakeflask with 10 g/L sucrose as sole carbon source and grown at 30° C. Regular samples are taken and the production of N-acetylneuraminate is measured as described in example 1. This strain and method produces quantities of 6sialyllactose.

The same organism also produces N-acetylneuraminate based on glucose, maltose or glycerol as carbon source.

Example 6: Production of Sialic Acid in *Saccharomyces cerevisiae* Using Autologous Fructose-6-P-Aminotransferase Another example provides use of a eukaryotic organism, in the form of *Saccharomyces cerevisae*, for this disclosure. This method utilizing the pathway of this disclosure shall be obtained in *Saccharomyces cerevisiae* by introducing and expressing a N-acetylglucosamine-2-epimerase (for example from *Bacteroides ovatus* (BoAGE)) and a sialic acid synthase (for example from *Campylobacter jejuni* (CjneuB)).

As a starting point, a strain with increased metabolic flux toward N-acetylglucosamine-6-phosphate is needed. This is achieved by overexpressing the native fructose-6-P-aminotransferase ScGFA1.

To create a N-acetylneuraminate producing *Saccharomyces cerevisiae* according to this disclosure, the genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmid used in this embodiment is p2a_2μ_sia_GFA1. This plasmid is introduced into *Saccharomyces cerevisae* using the transformation technique described by Gietz and Woods (2002) and a mutant strain is obtained.

The strain is capable of converting fructose-6-phosphate into glucosamine-6-phosphate, the glucosamine-6-phosphate into N-acetylglucosamine-6-phosphate, the N-acetylglucosamine-6-phosphate into N-acetylglucosamine, the N-acetylglucosamine into N-acetyl-mannosamine and finally the N-acetylmannosamine into N-acetyl-neuraminate.

A preculture of the strain is made in 5 mL of the synthetic defined medium SD-CSM containing 22 g/L glucose and grown at 30° C. as described in example 1. This preculture is inoculated in 100 mL medium in a shakeflask with 10 g/L sucrose as sole carbon source and grown at 30° C. Regular samples are taken and the production of N-acetylneuraminate is measured as described in example 1. This strain and method produces quantities of N-acetyl-neuraminate.

The same organism also produces N-acetylneuraminate based on glucose, maltose or glycerol as carbon source.

Example 7: Production of Sialyllactoses and Other Sialylated Compounds

In an alternative embodiment of example 3, the sialyltransferase is changed to another sialyltransferase with different activity. This can be an alpha-2,3-sialyltransferase alpha-2,6-sialyltransferase, an alpha-2,8-sialyltransferase or a combination thereof. These sialyltransferases are widely available in nature and well annotated.

In this way, production of different sialyllactoses like for example 6-sialyllactose, 3-sialyllactose or a mixture thereof can be obtained.

The strains are cultivated as stated in example 1 and example 3.

The pathways created in examples 2 to 7 can also be combined with other pathways for the synthesis of larger oligosaccharides, e.g., sialyl-lacto-N-triose, sialyllacto-N-tetraose, disialyllactose-N-tetraose, sialyllacto-N-neotetraose, and di sialyllactose-N-neotetraose. To this end, the transferases to synthetize these glycosidic bonds are co-expressed with the pathway genes to form CMP-sialic acid and the transferase (as described above) to sialylate the oligosaccharide.

Examples of such sialyltransferases are ST6GalI, ST6GalII, ST3GalI until VI, ST6GalNAc I until VI and ST8Sia I until VI, as described by Datta (Current Drug Targets, 2009, 483-498) and Harduin-Lepers (Biochimie 83 (2001) 727-737). Further examples originating from marine organisms are described by Yamamoto (March Drugs 2010, 8, 2781-2794).

Example 8: Production of Sialylated Lacto-N-Neotetraose

The aim of this experiment was to demonstrate the functionality of this disclosure of the production of other sialylated oligosaccharides, in this case sialyltated lacto-N-neotetraose.

A lacto-N-neotetraose producing strain was developed following the protocol described in example 1. For production, the expression of a N-acetylglucosaminyltransferase and a galactosyltransferase are needed, this is achieved by introduction of the genes NmlgtA and NmlgtB respectively, both from *Neisseria meningitides*. Next, the lactose importer EclacY from *Escherichia coli* is (as described and demonstrated in example 1 of WO 2016/075243, which is here also incorporated by reference). Finally, the genes ushA and galT are knocked out. In this way, a lacto-N-neotetraose producing strain is obtained.

To be able to grow on lactose and produce N-acetylglucosamine-6-phosphate, a sucrose phosphorylase from *Bifidobacterium adolescentis* (BaSP), a fructokinase from *Zymomonas mobilis* (frk) and a mutant fructose-6-P-aminotransferase (EcglmS*54, as described by Deng et al (Biochimie 88, 419-429 (2006))) were overexpressed as described in example 1.

In this strain, the method for producing sialic acid as described in this disclosure, was implemented by overexpressing a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Campylobacter jejuni* (CjneuB). ScGNA1 and BoAGE are expressed on locations nagABCDE and manXYZ, respectively. CjneuB is expressed from plasmid pCX-CjneuB-NmneuA-Pdbst.

Sialylation of the lacto-N-neotetraose moiety is performed by the conversion of sialic acid to CMP-sialic acid by a CMP sialic acid synthethase, e.g., NmneuA from *Neisseria meningtides*, subsequently followed by a sialyl transferase, e.g., Pdbst, from *Photobacterium damselae*. These genes (NmneuA and Pdbst) are expressed from the high copy plasmid pCX-CjneuB-NmneuA-Pdbst.

The strain is cultured as described in example 1 (materials and methods). Briefly, a 5 mL LB preculture is inoculated and grown overnight at 37° C. This culture was used as inoculum in a shake flask experiment with 100 mL medium that contains 10 g/L sucrose as carbon and energy source, 10 g/L lactose as precursor and was made according to the description in example 1. Regular samples are taken and analyzed. This strain produces quantities of sialylated lacto-N-neotetraose.

Alternative glycosyltransferases are possible. If EcWgbO (from *Escherichia coli* O55:H7) is expressed instead of NmlgtB for example, production of sialylated lacto-N-tetraose is obtained.

Example 9: Production of Sialic Acid with *Bacillus subtilis*

In another embodiment, this disclosure can be used for production of N-acetyl-neuraminate in *Bacillus subtilis*, yet another bacterial production host.

A N-acetylneuraminate producing strain is obtained through this disclosure by starting with a strain, capable of overproducing glucosamine-6-phosphate intracellularly. For this, the native fructose-6-P-aminotransferase (BsglmS) is overexpressed. The following enzymatic activities are disrupted by knocking out the genes nagA, nagB and gamA: N-acetylglucosamine-6-phosphate deacetylase and glucosamine-6-phosphate isomerase.

In this strain, the method for producing sialic acid as described in this disclosure, is implemented by overexpressing a glucosamine-6-P-aminotransferase from *Saccharomyces cerevisiae* (ScGNA1), a N-acetylglucosamine-2-epimerase from *Bacteroides ovatus* (BoAGE) and a sialic acid synthase from *Campylobacter jejuni* (CjneuB). These genes are introduced via a plasmid, as described in example 1.

The strain is cultured as described in example 1 (materials and methods). Briefly, a 5 mL LB preculture is inoculated and grown overnight at 30° C. This culture is used as inoculum in a shake flask experiment with 100 mL medium that contains 10 g/L sucrose and is made according to the description in example 1. This strain produces quantities of N-acetylneuraminic acid.

Example 10: Fermentations of 6-Sialyllactose Producing Strain with No Excretion of GlcNAc, ManNAc or Sialic Acid Another example according to this disclosure provides use of the method and strains for the production of 6-sialyllactose.

An *Escherichia coli* strain capable of accumulating glucosamine-6-phosphate using sucrose as a carbon source was further engineered to allow for N-acetyl-neuraminate production. This base strain overexpresses a sucrose phosphorylase from *Bifidobacterium adolescentis* (BaSP), a fructokinase from *Zymomonas mobilis* (Zmfrk), a mutant fructose-6-P-aminotransferase (EcglmS*54, as described by Deng et al. (Biochimie 88, 419-429 (2006)). To allow for 6-sialyllactose production the operons nagABCDE, nanATEK and manXYZ were disrupted. BaSP and Zmfrk were introduced at the location of nagABCDE, EcglmS*54 was introduced at the location of nanATEK. These modifications were done as described in example 1 and are based on the principle of Datsenko & Wanner (PNAS USA 97, 6640-6645 (2000)).

In this strain, the biosynthetic pathway for producing 6-sialyllactose as described in this disclosure, was implemented by overexpressing a glucosamine-6-P-aminotransferase from *Saccharomyces cerevisiae* (ScGNA1), a N-acetylglucosamine-2-epimerase from *Bacteroides ovatus* (BoA GE) and a sialic acid synthase from *Neisseria meningitides* (NmneuB). ScGNA1 and BoAGE were expressed on locations nagABCDE and manXYZ, respectively. NmNeuB was expressed using the high copy plasmid pBR322-NmNeuB. The strain is further modified by overexpressing a lactose permease EclacY from *Escherichia coli* (as described and demonstrated in example 1 of WO 2016/075243, which is here also incorporated by reference), a CMP-sialic acid synthethase from *Neisseria meningitides* (NmNeuA) and a sialyltransferase from *Photobacterium damselae* (Pdbst). On top of that, lacZ is disrupted. NmNeuA and Pdbst were expressed using the low copy plasmid pSC101-NmneuA-Pdbst.

The strain was cultured in a bioreactor as described in example 1 (materials and methods). Briefly, a 5 mL LB preculture was inoculated and grown overnight at 37° C. This culture was used as inoculum in a shake flask experiment with 500 mL medium that contains sucrose and was made as described in example 1. This culture was used as inoculum in a 2 L bioreactor experiment. Regular samples were taken and analyzed as described in example 1. The final concentration of 6-sialyllactose was 30.5 g/L. No extracellular GlcNAc, ManNAc and sialic acid was detected during the fermentation and in the final broth.

The same organism also produces 6-sialyllactose based on glucose, maltose or glycerol as carbon source.

Example 11: Effect of Phosphatase on Growth and Production of Sialic Acid

A further example provides growth results and sialic acid production of several *Escherichia coli* strains capable of producing N-acetylneuraminate (sialic acid) wherein the strains are expressing an extra phosphatase as indicated hereunder.

The base strain overexpresses a mutant fructose-6-P-aminotransferase (EcglmS*54, as described by Deng et al. (Biochimie 88, 419-429 (2006)), a glucosamine-6-P-aminotransferase from *Saccharomyces cerevisiae* (ScGNA1), a N-acetylglucosamine-2-epimerase from *Bacteroides ovatus* (BoA GE) and a sialic acid synthase from *Campylobacter jejuni* (CjneuB). To allow for gene sialic acid production the operons nagABCDE and nanATEK. The lacYZA operon was replaced by only a single gene operon, the native lacY, which is required for the production of sialyllactose as described in example 10. These modifications were done as described in example 1 and are based on the principle of Datsenko & Wanner (PNAS USA 97, 6640-6645 (2000)).

This base strain was then supplemented with different phosphatase bearing plasmids for comparing the effect of the phosphatase on growth and sialic acid production. The base strain was used as blank in the comparison. These plasmids consisted of, besides the phosphatase and a promoter driving expression of the phosphatase, a pSC101 ori and a spectomycin resistance marker. The following phosphatases were expressed: EcAphA (SEQ ID NO: 42), EcCof (SEQ ID NO: 43), EcHisB (SEQ ID NO: 44), EcOtsB (SEQ ID NO: 45), EcSurE (SEQ ID NO: 46), EcYaed (SEQ ID NO: 47), EcYcjU (SEQ ID NO: 48), EcYedP (SEQ ID NO: 49), EcYfbT (SEQ ID NO: 50), EcYidA (SEQ ID NO: 51), EcYigB (SEQ ID NO: 52), EcYihX (SEQ ID NO: 53), EcYniC (SEQ ID NO: 54), EcYqaB (SEQ ID NO: 55), EcYrbL (SEQ ID NO: 56) and PsMupP (SEQ ID NO: 57). Other phosphatases that are expressed are EcAppA (SEQ ID NO: 58), EcGph (SEQ ID NO: 59), EcSerB (SEQ ID NO: 60), EcNagD (SEQ ID NO: 61), EcYbhA (SEQ ID NO: 62), EcYbiV (SEQ ID NO: 63), EcYbjL (SEQ ID NO: 64), EcYfbR (SEQ ID NO: 65), EcYieH (SEQ ID NO: 66), EcYjgL (SEQ ID NO: 67), Ec YjjG (SEQ ID NO: 68), EcYrfG (SEQ ID NO: 69), EcYbiU (SEQ ID NO: 70), ScDOG1 (SEQ ID NO: 71) and BsAraL (SEQ ID NO: 72).

In a first experiment a subset of the above described strains was used. In a second experiment a second subset of the above described strains were tested.

Each strain was cultured as described in example 1 (materials and methods). Briefly, the workflow consists of 3 growth steps: first growth on LB, followed by growth on MMsf with 15 g/L glycerol, and finally a growth stage using 15 g/L glycerol MMsf. The first step is performed in a 96well plate, using 175 µL LB per well, and incubated overnight at 37° C. The second step is performed in a 96well plate using 175 µL medium, incubated for 24 h at 37° C. The final growth step was performed in: i) in a 96well plate using 175 µL medium, incubated at 37° C. to determine the µMax for the first experiment (see FIG. 5) and ii) in a 24well deepwell plates using 3 mL do determine sialic acid production and optical densities for the second experiment (see FIG. 4).

Figure 4:
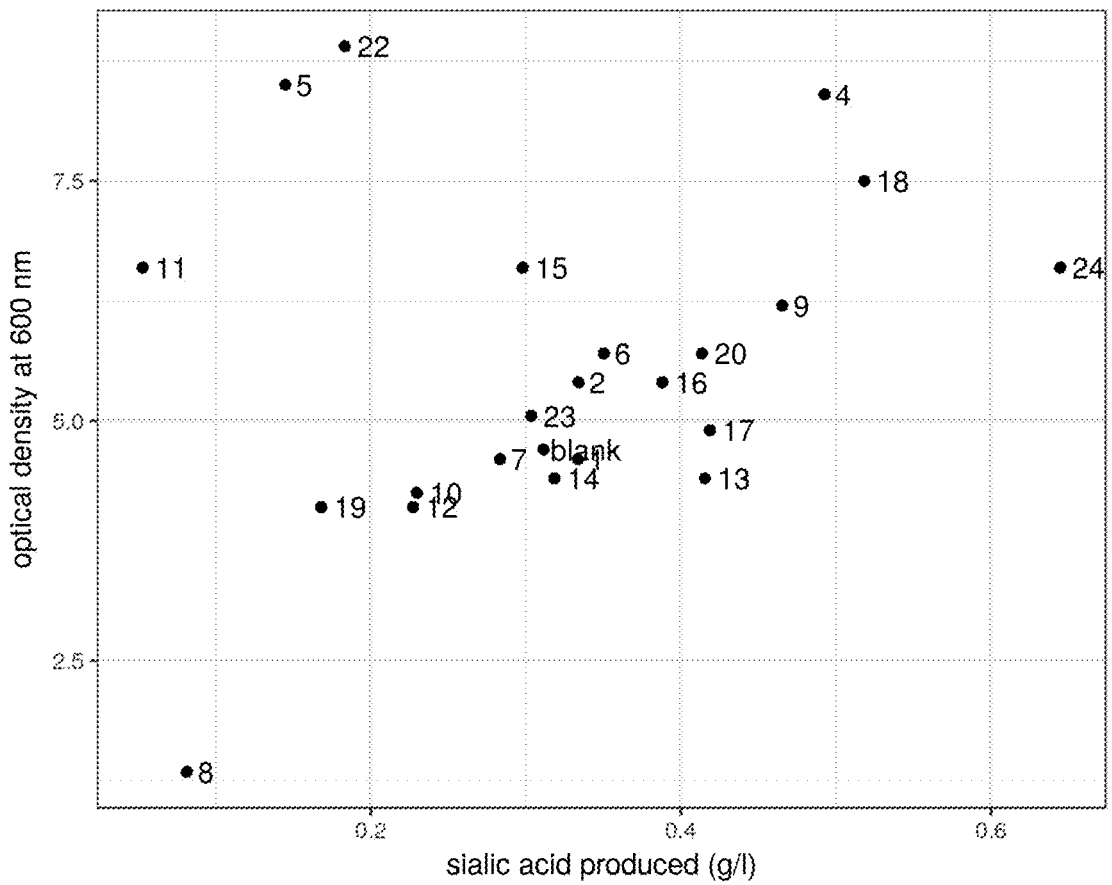
FIG. 4 shows the optical density and sialic acid production of strains supplemented with the indicated phosphatases.
Figure 5:
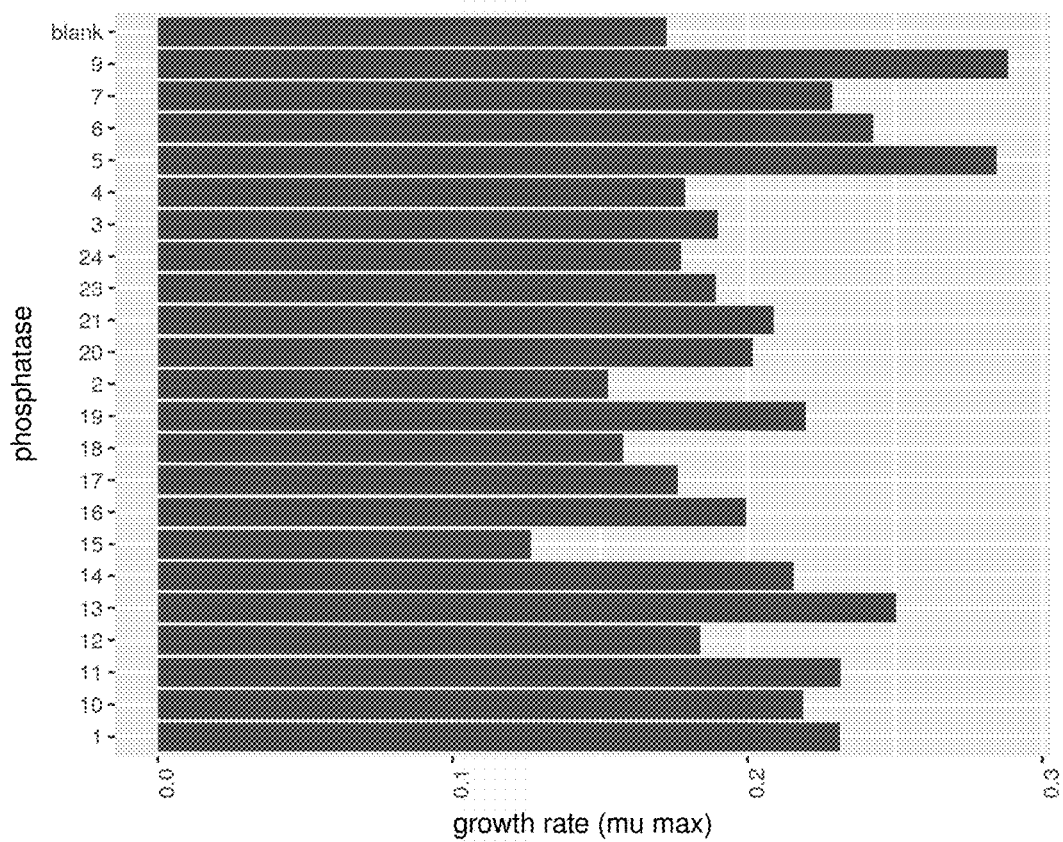
FIG. 5 shows the growth rates of strains supplemented with the indicated phosphatases.

Reference table for FIGS. 4 and 5:

| label | phosphatase | SEQ ID NO | Promotor |
|---|---|---|---|
| blank | NA | NA | NA |
| 1 | EcAphA | 42 | apFAB346 |
| 2 | EcAphA | 42 | apFAB87 |
| 3 | EcCof | 43 | apFAB87 |
| 4 | EcCof | 43 | apFAB346 |
| 5 | EcHisB | 44 | apFAB346 |
| 6 | EcOtsB | 45 | apFAB346 |
| 7 | EcSurE | 46 | apFAB346 |
| 8 | EcSurE | 46 | apFAB87 |
| 9 | EcYaed | 47 | apFAB346 |
| 10 | EcYaed | 47 | apFAB87 |
| 11 | EcYcjU | 48 | apFAB87 |
| 12 | EcYedP | 49 | apFAB87 |
| 13 | EcYfbT | 50 | apFAB87 |
| 14 | EcYidA | 51 | apFAB346 |
| 15 | EcYidA | 51 | apFAB87 |
| 16 | EcYigB | 52 | apFAB346 |
| 17 | EcYihX | 53 | apFAB346 |
| 18 | EcYihX | 53 | apFAB87 |
| 19 | EcYniC | 54 | apFAB346 |
| 20 | EcYniC | 54 | apFAB87 |
| 21 | EcYqaB | 55 | apFAB87 |
| 22 | EcYqaB | 55 | apFAB346 |
| 23 | EcYrbL | 56 | apFAB87 |
| 24 | PsMupP | 57 | apFAB87 |

Based on FIGS. 4 and 5 phosphatases enabling strains to grow better than the blank strain (no crippled growth) and producing more sialic acid than the blank strain, can be chosen.

Based on the above, it was found that phosphatases comprising at least Motif 1 and Motif 2 provide a strain that is not crippled and produces more sialic acid than the blank strain.

Example 12: Identification of Further Sequences Related to the Phosphatases Used in the Methods of this Disclosure Sequences (polypeptides) related to SEQ ID NOs: 43, 44, 45, 47, 48, 49, 50, 51, 52, 54, 55 and 57 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical amino acids between the two compared polypeptide sequences over a particular length. In some instances, the default parameters may be adjusted to modify the stringency of the search. For example, the E-value may be increased to show less stringent matches. This way, short nearly exact matches may be identified.

Table 1A to 1K provides a list of homologue polypeptide sequences related to SEQ ID NO: 43, 44, 45, 47, 48, 50, 51, 52, 54, 55 and 57, respectively.

TABLE 1A

Examples of polypeptides related to Ec Cof (SEQ ID NO: 43), showing sequence identity to SEQ ID 43:

| % identity (matgat) | short genbank identifier | SEQ ID NO |
|---|---|---|
| 99.6 | Shigella flexneri WP_095762248.1 | 78 |
| 99.3 | Shigella boydii WP_095785299.1 | 79 |
| 98.2 | Escherichia fergusonii WP_024256925.1 | 80 |
| 89.3 | Staphylococcus aureus WP_094409981.1 | 81 |
| 89 | Escherichia albertii WP_000113024.1 | 82 |
| 81.6 | Citrobacter amalonaticus WP_046476411.1 | 83 |
| 81.6 | Salmonella enterica WP_023234244.1 | 84 |
| 80.5 | Escherichia coli WP_088543831.1 | 85 |

TABLE 1B

Examples of polypeptides related to Ec HisB (SEQ ID NO: 44), showing sequence identity to SEQ ID 44:

| % identity (matgat) | short genbank identifier | SEQ ID NO |
|---|---|---|
| 99.4 | Shigella flexneri K-315 EIQ21345.1 | 86 |
| 99.2 | Escherichia albertii WP_059217413.1 | 87 |
| 98.9 | Shigella flexneri WP_094085559.1 | 88 |
| 98.6 | Shigella sonnei WP_077125326.1 | 89 |
| 98.6 | Escherichia coli WP_088129012.1 | 90 |
| 98 | Shigella dysenteriae WP_000080078.1 | 91 |
| 98 | Escherichia marmotae WP_038355110.1 | 92 |
| 94.6 | Salmonella bongori WP_000080052.1 | 93 |

TABLE 1C

Examples of polypeptides related to Ec OtsB (SEQ ID NO: 45), showing sequence identity to SEQ ID 45:

| % identity (matgat) | short genbank identifier | SEQ ID NO |
|---|---|---|
| 99.6 | Shigella sonnei WP_077124555.1 | 94 |
| 99.6 | Escherichia coli WP_032172688.1 | 95 |
| 99.2 | Shigella flexneri WP_064198868.1 | 96 |
| 85.7 | Escherichia albertii WP_059227241.1 | 97 |
| 83.1 | Escherichia fergusonii WP_000165652.1 | 98 |

TABLE 1D

Examples of polypeptides related to Ec Yaed (SEQ ID NO: 47), showing sequence identity to SEQ ID 47:

| % identity (matgat) | short genbank identifier | SEQ ID NO |
|---|---|---|
| 99.5 | Escherichia fergusonii WP_001140180.1 | 99 |
| 99.5 | Shigella sonnei WP_047565591.1 | 100 |
| 99 | Escherichia coli WP_061103769.1 | 101 |
| 95.8 | Escherichia albertii WP_001140171.1 | 102 |
| 93.2 | Kluyvera intermedia WP_047371746.1 | 103 |
| 93.2 | Citrobacter koseri WP_047458784.1 | 104 |
| 89 | Kosakonia arachidis WP_090122712.1 | 105 |
| 85.9 | Kluyvera cryocrescens WP_061282459.1 | 106 |
| 85.9 | Leclercia adecarboxylata WP_039030283.1 | 107 |

TABLE 1E

Examples of polypeptides related to Ec YcjUB (SEQ ID NO: 48), showing sequence identity to SEQ ID NO: 48:

| % identity (matgat) | short genbank identifier | SEQ ID NO |
|---|---|---|
| 99.5 | Shigella sonnei WP_094313132.1 | 108 |
| 97.7 | Escherichia coli WP_000775764.1 | 109 |
| 95.4 | Escherichia coli WP_032302947.1 | 110 |
| 92.7 | Shigella flexneri OUZ88260.1 | 111 |

TABLE 1F

Examples of polypeptides related to Ec YfbT (SEQ ID NO: 50), showing sequence identity to SEQ ID NO: 50:

| % identity (matgat) | short genbank identifier | SEQ ID NO |
|---|---|---|
| 99.1 | Shigella sonnei WP_094323443.1 | 112 |
| 87.5 | Citrobacter werkmanii NBRC 105721 GAL43238.1 | 113 |
| 86.6 | Citrobacter freundii KGZ33467.1 | 114 |
| 86.6 | Citrobacter amalonaticus Y19 AKE59306.1 | 115 |
| 85.6 | Salmonella enterica WP_080095242.1 | 116 |
| 85.6 | Escherichia fergusonii WP_001203376.1 | 117 |
| 85.6 | Salmonella enterica subsp. enterica serovar Hadar KKD79316.1 | 118 |

TABLE 1G

Examples of polypeptides related to Ec YidA (SEQ ID NO: 51), showing sequence identity to SEQ ID NO: 51:

| % identity (matgat) | short genbank identifier | SEQ ID NO |
|---|---|---|
| 99.6 | Escherichia coli WP_053263719.1 | 119 |
| 99.3 | Escherichia fergusonii WP_000985562.1 | 120 |
| 99.3 | Shigella sonnei WP_094337696.1 | 121 |
| 94.4 | Trabulsiella guamensis WP_038161262.1 | 122 |
| 94.1 | Citrobacter amalonaticus WP_061075826.1 | 123 |
| 93.7 | Klebsiella pneumoniae WP_048288968.1 | 124 |
| 93.3 | Trabulsiella odontotermitis WP_054178096.1 | 125 |
| 90 | Enterobacter kobei WP_088221256.1 | 126 |

TABLE 1H

Examples of polypeptides related to Ec YigB (SEQ ID NO: 52), showing sequence identity to SEQ ID NO: 52:

| % identity (matgat) | short genbank identifier | SEQ ID NO |
|---|---|---|
| 99.6 | Shigella sonnei WP_094322240.1 | 127 |
| 93.7 | Shigella sonnei WP_052962467.1 | 128 |
| 87 | Salmonella enterica WP_079797638.1 | 129 |
| 85.7 | Citrobacter braakii WP_080625916.1 | 130 |
| 81.9 | Enterobacter hormaechei WP_047737367.1 | 131 |

TABLE 1H-continued

Examples of polypeptides related to Ec YigB (SEQ ID NO: 52),
showing sequence identity to SEQ ID NO: 52:

| % identity (matgat) | short genbank identifier | SEQ ID NO |
|---|---|---|
| 81.1 | Lelliottia amnigena WP_059180726.1 | 132 |
| 80.3 | Leclercia adecarboxylata WP_039031210.1 | 133 |

TABLE 1I

Examples of polypeptides related to Ec YniC (SEQ ID NO: 54),
showing sequence identity to SEQ ID NO: 54:

| % identity (matgat) | short genbank identifier | SEQ ID NO |
|---|---|---|
| 85.6 | Shigella flexneri 1235-66 EIQ75633.1 | 134 |
| 85.1 | Kosakonia sacchari WP_074780431.1 | 135 |
| 85.1 | Enterobacter mori WP_089599104.1 | 136 |
| 84.7 | Lelliottia amnigena WP_064325804.1 | 137 |
| 84.7 | Enterobacter sp. 638 WP_012017112.1 | 138 |
| 84.2 | Kosakonia radicincitans WP_071920671.1 | 139 |
| 84.2 | Salmonella enterica subsp. enterica serovar Newport str. CDC 2010K-2159 AKD18194.1 | 140 |

TABLE 1J

Examples of polypeptides related to Ec YqaB (SEQ ID NO: 55),
showing sequence identity to SEQ ID NO: 55:

| % identity (matgat) | short genbank identifier | SEQ ID NO |
|---|---|---|
| 97.9 | Shigella flexneri K-315 EIQ18779.1 | 141 |
| 93.6 | Escherichia albertii WP_059215906.1 | 142 |
| 88.3 | Salmonella enterica WP_079949947.1 | 143 |
| 85.6 | Kluyvera intermedia WP_085006827.1 | 144 |
| 85.1 | Trabulsiella odontotermitis WP_054177678.1 | 145 |
| 84.6 | Yokenella regensburgei WP_006817298.1 | 146 |
| 84.6 | Raoultella terrigena WP_045857711.1 | 147 |
| 83.5 | Klebsiella pneumoniae WP_064190334.1 | 148 |

TABLE 1K

Examples of polypeptides related to Ps MupP (SEQ ID NO: 57),
showing sequence identity to SEQ ID NO: 57:

| % identity (matgat) | short genbank identifier | SEQ ID NO |
|---|---|---|
| 94.6 | Pseudomonas putida group WP_062573193.1 | 149 |
| 94.6 | Pseudomonas sp. GM84 WP_008090372.1 | 150 |
| 93.3 | Pseudomonas entomophila | 151 |
| 92.4 | Pseudomonas vranovensis WP_028943668.1 | 152 |
| 83.9 | Pseudomonas cannabina WP_055000929.1 | 153 |
| 93.3 | Pseudomonas monteilii WP_060480519.1 | 154 |

Sequences have been tentatively assembled and publicly disclosed by research institutions, such as The Institute for Genomic Research (TIGR; beginning with TA). The Eukaryotic Gene Orthologs (EGO) database may be used to identify such related sequences, either by keyword search or by using the BLAST algorithm with the nucleic acid sequence or polypeptide sequence of interest. Special nucleic acid sequence databases have been created for particular organisms, such as by the Joint Genome Institute.

Example 13: Identification of Domains and Motifs Comprised in Polypeptide Sequences Useful in Performing the Methods of this Disclosure The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The results of the InterPro scan of the polypeptide sequences as represented by SEQ ID NOs: 43, 44, 45, 47, 48, 49, 50, 51, 52, 54 and 55 are presented in Table 2.

TABLE 2

InterPro scan results (major accession numbers) of the polypeptide sequence as represented by SEQ ID NOs: 43, 44, 45, 47, 48, 49, 50, 51, 52, 54 and 55.

| Database | Accession number | Accession name |
|---|---|---|
| Interpro | IPR023214 | HAD superfamily |

Figure 6:
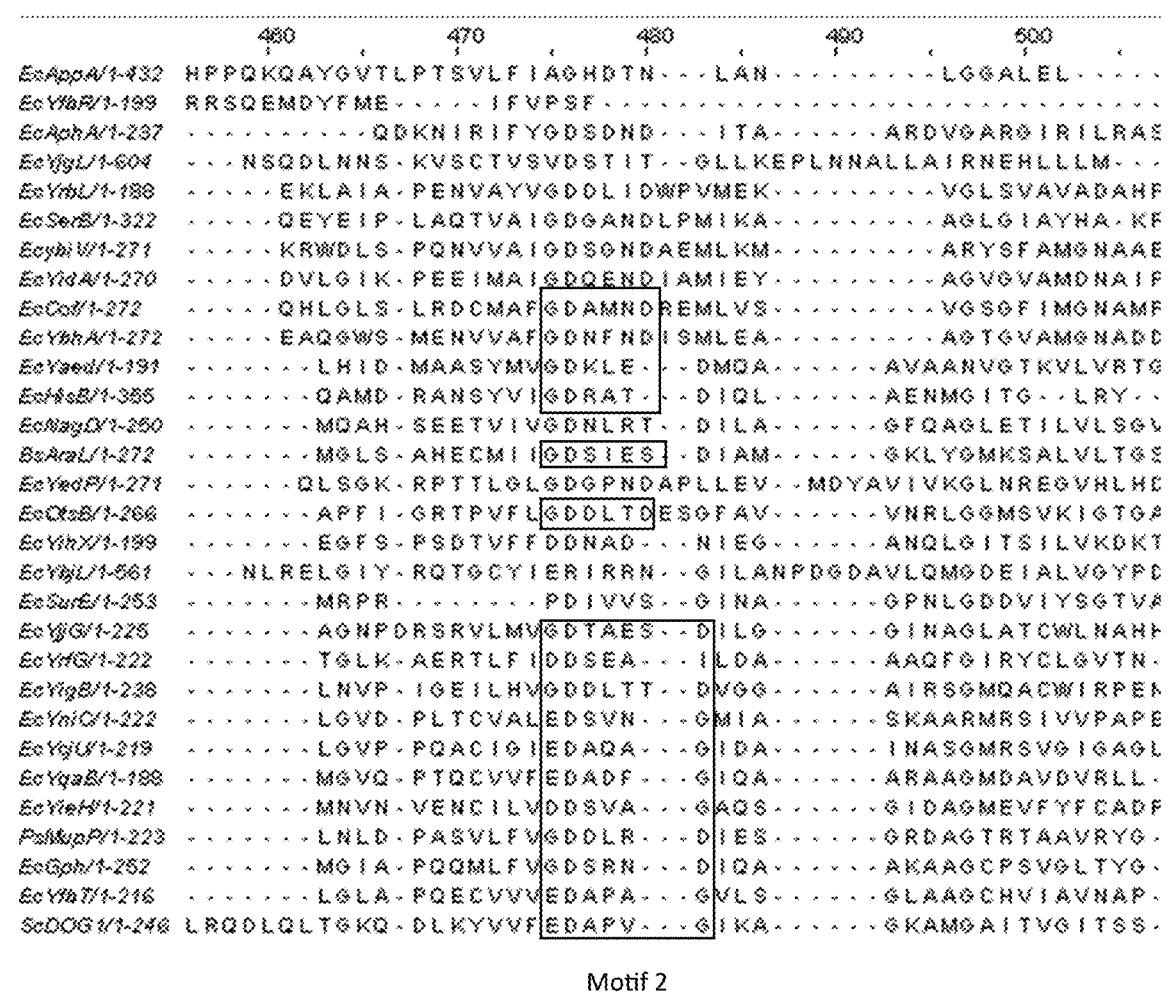

Alignment of the tested phosphatase polypeptides was done and FIG. 6 shows part of the alignment. Motif 1 and motif 2 are indicated with boxes. Alignment was made using clustalomega.

Example 14: Effect of Phosphatase on Growth and Production of Sialic Acid in Saccharomyces cerevisiae A further example of sialic acid production of several Saccharomyces cerevisiae strains capable of producing N-acetylneuraminate (sialic acid) wherein the strains are expressing an extra phosphatase as indicated hereunder.

The strain used here is derived from the strain described in example 4. To enhance growth and production of sialic acid in Saccharomyces cerevisiae according to this disclosure, the phosphatase genes are introduced via a 2-micron plasmid (Chan 2013 (Plasmid 70 (2013) 2-17)) and the genes are expressed using synthetic constitutive promoters (Blazeck 2012 (Biotechnology and Bioengineering, Vol. 109, No. 11)) as also described in example 1. The specific plasmids used in this embodiment is p2a_2μ_sia_glmS-phospha. This plasmid based on the plasmid p2a_2μ_sia_glmS plasmid is described in example 1. It is introduced into Saccharomyces cerevisae using the transformation technique described by Gietz and Woods (2002, PMID 12073338) and a mutant strain is obtained. The effect of phosphatase expression on growth and production of sialic acid of these mutants are evaluated as described in example 11.

Example 15: Effect of Phosphatase on Growth and Production of Sialic Acid in Bacillus subtilis In another embodiment, this disclosure can be used to enhance growth and production of sialic acid in Bacillus subtilis, yet another bacterial production host.

The strain used here is derived from the strain described in example 9. Additionally to the alterations described in example 9, phosphatase genes EcAphA (SEQ ID NO: 42), EcCof (SEQ ID NO: 43), EcHisB (SEQ ID NO: 44), EcOtsB (SEQ ID NO: 45), EcSurE (SEQ ID NO: 46), EcYaed (SEQ ID NO: 47), EcYcjU (SEQ ID NO: 48), EcYedP (SEQ ID NO: 49), EcYfbT (SEQ ID NO: 50), EcYidA (SEQ ID NO: 51), EcYigB (SEQ ID NO: 52), EcYihX (SEQ ID NO: 53), EcYniC (SEQ ID NO: 54), EcYqaB (SEQ ID NO: 55), EcYrbL (SEQ ID NO: 56), PsMupP (SEQ ID NO: 57), EcAppA (SEQ ID NO: 58), EcGph (SEQ ID NO: 59), EcSerB (SEQ ID NO: 60), EcNagD (SEQ ID NO: 61), EcYbhA (SEQ ID NO: 62), EcYbiV (SEQ ID NO: 63), EcYbjL (SEQ ID NO: 64), EcYfbR (SEQ ID NO: 65), EcYieH (SEQ ID NO: 66), EcYjgL (SEQ ID NO: 67), EcYjjG (SEQ ID NO: 68), EcYrfG (SEQ ID NO: 69), EcYbiU (SEQ ID NO: 70), ScDOG1 (SEQ ID NO: 71) and BsAraL (SEQ ID NO: 72) are overexpressed on a plasmid, as described in example 1. Subsequently, this plasmid is introduced in *Bacillus subtilis*. The effect of phosphatase expression on growth and production of sialic acid of the created mutants are evaluated as described in example 11.

The invention claimed is:

1. A method for fermentative production of a sialylated oligosaccharide, the method comprising cultivating a metabolically engineered microorganism, wherein the metabolically engineered microorganism:
   i) comprises a sialic acid biosynthesis pathway that converts:
      glucosamine-6-phosphate to N-acetylglucosamine-6-phosphate,
      N-acetylglucosamine-6-phosphate to N-acetylglucosamine,
      N-acetylglucosamine to N-acetylmannosamine, and
      N-acetylmannosamine to N-acetyl-neuraminate,
   ii) converts N-acetylneuraminate to cytidine monophosphate (CMP)-N-acetylneuraminate (also known as CMP-sialic acid), and
   iii) comprises a heterologous sialyltransferase.

2. The method according to claim 1, wherein the microorganism comprises:
   i) a sialic acid biosynthesis pathway comprising glucosamine 6-phosphate N-acetyltransferase, N-acylglucosamine 2-epimerase, and N-acetylneuraminic acid synthetase, and
   ii) a cytidine 5'-monophospho-N-acetylneuraminic acid synthetase (CMP-N-acetylneuraminic acid synthetase or CMP-sialic acid synthetase).

3. The method according to claim 1, wherein the sialyltransferase originates from *Photobacterium damselae*.

4. The method according to claim 1, wherein the metabolically engineered microorganism
   a) has a reduced or abolished expression of at least one polynucleotide encoding or driving expression of a polypeptide that converts i)N-acetylglucosamine-6-P to glucosamine-6-P, ii)N-acetyl-glucosamine to N-acetyl-glucosamine-6-P, or iii)N-acetyl-neuraminate to N-acetyl-mannosamine, or
   b) is unable to convert at least one of
      i)N-acetylglucosamine-6-P to glucosamine-6-P,
      ii)N-acetyl-glucosamine to N-acetyl-glucosamine-6-P, and
      iii)N-acetyl-neuraminate to N-acetyl-mannosamine.

5. The method according to claim 1, wherein the metabolically engineered microorganism has a reduced or abolished activity of at least one enzyme selected from the group consisting of i) a N-acetylglycosamine-6-phosphate deacetylase, ii) a N-acetylglucosamine kinase, and iii) a N-acetylneuraminate aldolase.

6. The method according to claim 1, wherein the microorganism comprises:
   at least one polynucleotide encoding a phosphatase that comprises at least one of:
      Motif 1: hDxDx[TV] (SEQ ID NO: 73), or
      Motif 2: [GSTDE][DSEN]x(1-2)[hP]x(1-2)[DGTS] (SEQ ID NOs: 74, 75, 76, 77),
      wherein h is a hydrophobic amino acid (A, I, L, M, F, V, P, or G) and x can be any distinct amino acid,
   at least one polynucleotide encoding an N-acetylmannosamine epimerase,
   at least one polynucleotide encoding a sialyltransferase,
   at least one polynucleotide encoding a CMP-sialic acid synthetase, and
   at least one polynucleotide encoding a sialic acid synthase.

7. The method according to claim 1, wherein the microorganism comprises a polynucleotide encoding a sialic acid synthase polypeptide originating from *Campylobacter jejuni* or *Neisseria meningitides*.

8. The method according to claim 1, wherein the microorganism further exhibits an increased expression of a phosphatase comprising:
   any one of SEQ ID NOs: 58-60, 65, 67, 69, and 70, or
   a homologue of the polypeptide of any one of SEQ ID NOs: 42-48, 50-52, 54, 55, 57-60, 65, 67, 69, and 70, having at least 80% overall sequence identity to the polypeptide, which homologue has phosphatase activity,
   wherein the homologue increases one or more of sialic acid, biomass production and maximal growth rate in the microorganism as compared to a reference strain of the microorganism having the same genetic make-up, but lacking increased expression of the phosphatase.

9. The method according to claim 1, wherein the sialylated oligosaccharide is selected from the group consisting of sialyllactose, disialyl lacto-N-tetraose, sialylated lacto-N-triose, sialylated lacto-N-tetraose, and sialylated lacto-N-neotetraose.

10. The method according to claim 1, wherein the sialylated oligosaccharide is sialyllactose.

11. The method according to claim 1, wherein the sialylated oligosaccharide is 3'sialyllactose.

12. The method according to claim 1, wherein the sialylated oligosaccharide is 6'sialyllactose.

13. The method according to claim 1, wherein the sialylated oligosaccharide is a sialylated lacto-N-triose, sialylated lacto-N-tetraose or sialylated lacto-N-neotetraose, and
   wherein the microorganism further has galactosyltransferase (EC 2.4.1.38) activity, and/or N-acetylglucosaminyltransferase (EC 2.4.1.90) activity.

14. The method according to claim 13, wherein the microorganism is unable to express genes coding for UDP sugar hydrolase and galactose-1-phosphate uridylyltransferase.

15. The method according to claim 6, wherein the N-acetyl-mannosamine epimerase and/or sialic acid synthase is/are overexpressed in the microorganism or is introduced and expressed in the microorganism.

16. The method according to claim 1, wherein the microorganism further:
   encodes a protein that facilitates uptake of lactose and lacks enzymes that metabolize lactose.

17. The method according to claim 1, wherein the microorganism is a bacterium or a yeast.

18. The method according to claim 1, wherein the metabolically engineered microorganism has at least one disabled polypeptide of the phosphoenolpyruvate: sugar phosphotransferase system for the import of a saccharide that is not used as a carbon source during fermentative production of the sialylated oligosaccharide.

19. The method according to claim 18, wherein the at least one polypeptide of the phosphoenolpyruvate: sugar phosphotransferase system is encoded by at least one of the genes selected from the group of genes encoding manX, manY, manZ, or nagE.

20. The method according to claim 1, wherein the microorganism can utilize an exogenous carbon source present in fermentation broth as sole carbon source without using a phosphoenolpyruvate: sugar phosphotranferase system for the acquisition of the exogenous carbon source.

* * * * *